United States Patent [19]
Jeffreys

[11] Patent Number: 5,413,908
[45] Date of Patent: May 9, 1995

[54] METHOD OF CHARACTERIZING GENOMIC DNA BY REFERENCE TO A GENETIC VARIABLE

[75] Inventor: Alec J. Jeffreys, Leicester, England

[73] Assignee: Lister Institute of Preventive Medicine, Middlesex, England

[21] Appl. No.: 921,375

[22] Filed: Jul. 29, 1992

Related U.S. Application Data

[60] Continuation of Ser. No. 228,523, Aug. 4, 1988, abandoned, which is a division of Ser. No. 783,790, Oct. 3, 1985, abandoned.

[30] Foreign Application Priority Data

Nov. 12, 1984 [GB] United Kingdom ............... 8428491
Mar. 6, 1985 [GB] United Kingdom ............... 8505744
Jul. 24, 1985 [GB] United Kingdom ............... 8518755
Sep. 6, 1985 [GB] United Kingdom ............... 8522135

[51] Int. Cl.⁶ ............................................. C12Q 1/68
[52] U.S. Cl. .................................. 435/6; 536/23.1; 536/24.2; 536/24.31; 935/78
[58] Field of Search ............... 536/24.3, 24.31, 23.1, 536/24.2; 435/6; 935/78

[56] References Cited

U.S. PATENT DOCUMENTS

| | | | |
|---|---|---|---|
| 4,963,663 | 10/1990 | White et al. ................. | 536/24.30 |
| 5,175,082 | 12/1992 | Jeffreys ........................ | 435/6 |

FOREIGN PATENT DOCUMENTS

| | | | |
|---|---|---|---|
| 0084796 | 8/1983 | European Pat. Off. .......... | 435/6 |
| 0135108 | 3/1985 | European Pat. Off. .......... | 435/6 |
| 57-182650 | 11/1982 | Japan ................................ | 435/6 |
| 2135774 | 9/1984 | United Kingdom ............... | 435/6 |
| 8303260 | 9/1983 | WIPO ............................... | 435/6 |
| 8502862 | 7/1985 | WIPO ............................... | 536/23.52 |

OTHER PUBLICATIONS

Smith, "Chi Hotspots of Generalized Recombination," *Cell*, 34, 709–710 (1983).
Smith et al., "Structure of Chi Hotspots of Generalized Recombination," *Cell*, 24, 429–436 (1981).
Capon et al., "Complete Nucleotide Sequences of the T24 Human Bladder Carcinoma Oncogene and Its Normal Homologue," *Nature*, 302, 33–37 (1983).

(List continued on next page.)

Primary Examiner—John W. Rollins
Assistant Examiner—L. Eric Crane
Attorney, Agent, or Firm—Nixon & Vanderhye

[57] ABSTRACT

It has been a problem that the identification of genomic DNA by restriction fragment length polymorphisms is limited, owing to the low level of genetic variation ordinarily detectable by cloned DNA in this method. The invention provides for improved identification by making use of the existence of DNA regions of hypervariability, otherwise called minisatellite regions in which the DNA contains tandem repeats or quasi-block copolymer sequences and the number of repeats or copolymer units varies considerably from one individual to another. It has now been found that many such regions can be probed simultaneously in such a way as to display this variability using a DNA or other polynucleotide probe of which the essential constituent is a short core sequence tandemly repeated at least 3 and preferably at least 10 times. The probing reveals differences in genomic DNA at multiple highly-polymorphic minisatellite regions to produce an individual-specific DNA "fingerprint" of general use for genetic identification purposes. The "core" used is typically a sequence of 6 to 16 nucleotides contained in or having a high degree of homology with a nucleotide sequence of formula GGAGGTGGGCAGGAXG (2) in which X is A or G, or AGAGGTGGGCAGGTGG (3) or GGAGGYGGGCAGCAGG (4) in which Y is C or T, or with a 12–15 nucleotide sequence of formula $T(C)_m GGAGGAXGG(G)_p C$ (5A) or $T(C)_m GGAGGA(A)_q GGGC$ (5B) in which X is A or G, M is 0, 1 or 2, p is 0 or 1, and q is 0 or 1, or GPGGGCWGGWXG (6) in which X is as above, P is not G, and W=A or G. The invention is particularly useful in paternity and maternity testing, forensic medicine and the diagnosis of genetic diseases and cancer.

6 Claims, 21 Drawing Sheets

OTHER PUBLICATIONS

Weller et al., "Organization of the Human Myoglobin Gene," *The EMBO J.*, 3(2), 439–446 (1984).

Proudfoot et al., "The Structure of the Human Zeta–Globin Gene and a Closely Linked, Nearly Pseudogene," *Cell*, 31, 553–563 (1982).

Wyman et al., "A Highly Polymorphic Locus in Human DNA," *Proc. Nat. Acad. Sci USA*, 77(11), 6754–6758 (1980).

Bell et al., "The Highly Polymorphic Region Near the Human Insulin Gene Is Composed of Simple Tandemly Repeating Sequences," *Nature*, 295, 31–35 (1982).

Goodbourn et al., "Molecular Basis of Length Polymorphism in the Human $\zeta$-Globin Gene Complex," *Proc. Nat. Acad. Sci USA*, 80, 5022–5026 (1983).

White et al., "Construction of Linkage Maps with DNA Markers of Human Chromosomes," *Nature*, 313, 101–105 (1985).

Jeffreys et al., "Hypervariable 'Minisatellite' Regions in Human DNA," *Nature*, 314, 67–73 (1985).

Jeffreys, "DNA Sequence Variants in the $G_\gamma$—, $A_\gamma$—, $\delta$—and $\beta$—Globin Genes in Man," *Cell*, 18, 1–10 (1979).

Corneo et al., "Restriction Enzyme Studies on Highly Repeated DNAs of Human Leukemic Leucocytes," *Haematoligica*, 67(5), 655–670 (1982).

Neve et al., "Comparison of Sequence Repetitiveness of Human cDNA and Genomic DNA Using the Miniplasmid Vector, piVX," *Gene*, 23(3), 355–367 (1983).

Frommer et al., "Human Satellite I Sequences Include a Male Specific 2.47 kb Tandemly Repeated Unit Containing One Alu Family Member per Repeat," *Nucleic Acids Research*, 12(6), 2887–2900 (1984).

Jeffreys et al., "Individual-Specific 'Fingerprints' of Human DNA," *Nature*, 316, 76–79 (1985).

Jabs et al., "Characterization of a Cloned DNA Sequence That Is Present at Centromeres of All Human Autosomes and the X Chromosome and Shows Polymorphic Variation," *Proc. Nat. Acad. Sci. USA*, 81(15), 4884–4888 (1984).

Yang et al., "Characterization of a Cloned Repetitive DNA Sequence Concentrated on the Human X Chromosome," *Proc. Nat. Acad. Sci. USA*, 79(21), 6593–6597 (1982).

Zaitsev et al., "Structural Analysis of the DNA Fragment with Dispersed Distribution Along Human Chromosomes Containing Alu Family Sequences," *Genetika*, 20(5), 738–745 (1984); Russian with English Abstract.

Singh et al., "The Conserved Nucleotide Sequences of Bkm, Which Define S xr in the Mouse, Are Transcribed," *Cell*, 36(1), 111–120 (1984).

Ali et al., "DNA Finger Printing by Oligonucleotide Probes Specific for Simple Repeats," *Human Genetics*, 74(3), 239–243 (1986).

Blanchetot et al., "The Seal Myoglobin Gene: An Unusually Long Globin Gene," *Nature*, 301, 732–734 (1983).

Akaboshi, "Cloning of the Human Myoglobin Gene," *Gene*, 33(3), 241–249 (1985).

Helentjaris et al., "Evaluation of Random cDNA Clones as Probes for Human Restriction Fragment Polymorphism," *J. Mol. Appl. Genet.*, 2(3), 237–247 (1983); *Chem. Abstr.*, 100(9), p. 147, Abstr. No. 62783z (1984); only Abstract supplied.

Lewin, "Sequences of Eucaryotic DNA," Ch. 4 in *Gene Expression, vol. 2, Eucaryotic Chromosomes*, John Wiley & Sons, New York, 1974, pp. 148–227, see particularly pp. 176–199.

Southern, "New Methods for Analysing DNA Make Genetics Simpler," *Biochem. Soc. Transactions*, 10(Pt. 1), 1–4, (1982).

Spielman et al., "The Genetics of Susceptibility to Multiple Sclerosis," *Epidemiologic Reviews*, 4, 45–65 (1982).

Balzacs et al., "Highly Polymorphic DNA Site D14S1 Maps to the Region of Burkitt Lymphoma Translocation and is Closely Linked to the Heavy Chain $\gamma$1 Immunoglobin Locus," *Proc. Nat. Acad. Sci. USA*, 79(23), 7395–7399 (1982).

Antonarakis et al., "Genetic Diseases: Diagnosis by Restriction Endonuclease Analysis," *J. Pediatrics*, 100(6), 845–856 (1982).

Kan, "Hemoglobin Abnormalities: Molecular and Evolutionary Studies," *The Harvey Lectures*, Series 76, 75–95 (1982).

Shows et al., "Mapping the Human Genome, Cloning Genes, DNA Polymorphisms, and Inherited Disease," Ch. 5 in *Adv. In Human Genetics*, 12, Plenum Press, New York, 1982, pp. 341–452.

Botstein et al., "Construction of a Genetic Linkage Map in Man Using Restriction Fragment Length Polymorphisms," *Am. J. Hum. Genet.*, 32, 314–331 (1980).

(List continued on next page.)

OTHER PUBLICATIONS

DeMartinville et al., "Assignment of the First Random Restriction Fragment Length Polymorphism (RFLP) Locus (D14S1) to a Region of Human Chromosome 14," *Am. J. Hum. Genet.*, 34, 216–226 (1982).

Kurnit et al, "Prenatal Analysis of Human DNA–Sequence Variation," Ch. 12 in *Methods in Cell Biology*, vol. 26, Academic Press, New York, 1982, pp. 311–330.

Page et al., "Single–Copy Sequence Hybridizes to Polymorphic and Homologous Loci on Human X and Y Chromosomes," *Proc. Nat. Acad. Sci. USA*, 79(17), 5352–5356 (1982).

Skolnick et al., "Strategies for Detecting and Characterizing Restriction Fragment Length Polymorphisms (RFLP's)," *Cytogenet. Cell Genet.*, 32, 158–67 (1982).

Puck et al., "Somatic Cell Genetics and Its Application to Medicine," *Am. Rev. Genet.*, 16, 225–271 (1982).

Brinton et al., "Genetic Determinants of Virus Susceptibility: Epidemiologic Implications of Murine Models," *Epidemiologic Reviews*, 3, 115–139 (1981).

Krumlauf et al., "Construction and Characterization of Genomic Libraries From Specific Human Chromosomes," *Proc. Nat. Acad. Sci. USA*, 79(1), 2971–2975 (1982).

Schedl et al., "Mendelian Analysis of the Organization of Actin Sequences in *Physarum polycephalum*," *J. Mol. Biol.*, 160, 41–57 (1982).

Lange et al, "How Many Polymorphic Genes Will It Take to Span the Human Genome?" *Am. J. Hum. Genet.*, 34, 842–845 (1982).

Kao et al., "Isolation and Chromosomal Localization of Unique DNA Sequences for am Human Genomic Library," *Proc. Nat. Acad. Sci. USA*, 79, 865–869 (1982).

Alwine et al., "Method for Detection of Specific RNAs in Agarose Gels by Transfer to Diazobenzyloxymethyl–paper and Hybridization with DNA Probes," *Proc. Nat. Acad. Sci. USA, 74(12), 5350–5354 (1977)*.

Williamson, "Human Chromosome–Specific Libraries," *Biology of the Cell*, 45, 346 (1982).

Wood, "DNA Probes and Carriers of X–Linked Disease," *Lancet 2*, 1219–1220 (1982).

Kan et al., "Polymorphism of DNA Sequence Adjacent to Human β—Globin Structural Gene: Relationship to Sickle Mutation," *Proc. Nat. Acad. Sci USA*, 75, 5631–5634 (1978).

Kan et al., "Antenatal Diagnosis of Sickle–Cell Anaemia by DNA Analysis of Amniotic–Fluid Cells," *Lancet 2*, 910 (1978).

Kronenberg, "Looking at Genes," *N. Engl. J. Med.*, 307(1), 50–51 (1982).

Law et al., "Isolation of a Human Repetitive Sequence and Its Application to Regional Chromosome Mapping," *Proc. Nat. Acad. Sci USA*, 79, 7390–7394 (1982).

Murray et al., "Linkage Relationship of a Cloned DNA Sequence on the Short Arm of the X–Chromosome to Duchenne Muscular Dystrophy," *Nature*, 300, 69–71 (1982).

Old et al., "First–Trimester Fetal Diagnosis for Haemoglobinopathies: Three Cases," *Lancet 2*, 1413–1416 (1982).

Dadone et al., "Hereditary Hemochromatosis," *Am. J. Clinical Pathologists*, 78, 196 (1982).

Davies, "A Cloned DNA Library from the Human X–Chromosome," *Biology of the Cell*, 45, 348 (1982).

Hill et al., "The Mendelian Inheritance of a Human X Chromosome–Specific DNA Sequence Polymorphism and Its Use in Linkage Studies of Genetic Disease," *Hum. Genet.*, 60(3), 222–226 (1982).

Kennett et al., "Cell Surface Changes in Malignancy," Ch. X in *Methods in Cancer Research*, vol. XX, Academic Press., New York, 1982, pp. 355–370.

Arnheim et al., "Distribution of Ribosomal Gene Length Variants Among Mouse Chromosomes," *Proc. Nat. Acad. Sci. USA*, 79(15), 4677–4680 (1982).

Asmussen et al., "Use of Restriction Fragment Length Polymorphisms for Genetic Counseling: Population Genetic Considerations," *Am. J. Hum. Genet.*, 34, 369–380 (1982).

Beaudet et al., "Dispersion of Argininosuccinate–Synthetase–Like Human Genes to Multiple Autosomes and the X Chromosomes," *Cell*, 30(1), 287–293 (1982).

Chakravarti et al., "Utility and Efficiency of Linked Marker Genes for Genetic Counseling. II. Identification of Linkage Phase by Offspring Phenotypes," *Am. J. Hum. Genet.*, 34, 531–551 (1982).

McFadden, "Reliability of DNA Testing Challenged by Judge's Ruling," *The New York Times*, Sec. B, p. 1, Aug. 15, 1989.

Reeck et al., "'Homology' in Proteins and Nucleic Acids: A Terminology Muddle and a Way out of It," *Cell*, 50, 667 (1987).

Lewin, "When Does Homology Mean Something Else?" *Science*, 237, 1570 (25 Sep. 1987).

(List continued on next page.)

OTHER PUBLICATIONS

Bishop et al., *Nucleic acid and protein sequence analysis*, IRL Press, Washington, D.C., 1987, see pp. 41–42, 322–358.

Leak, *Computational Molecular Biology, Sources and Methods for Sequence Analysis*, ICSU CODATA, New York, 1988, see pp. 10–11, 161–178.

Eppelen, "On Simple Repeated GAT/CA Sequences in Animal Genomes: A Critical Reappraisal," *J. Heredity*, 79, 409–417 (1988).

Jeffreys et al., "Abstract of a Talk to Poultry Research Center", GB, Circulated Oct. 22, 1984, Presented Nov. 22 & 27, 1984.

Gusella et al., "A Polymorphic DNA Marker Genetically Linked to Huntington's Disease," *Nature*, 306, 234–238 (1983).

*DNA Technology in Forensic Science*, Committee on DNA Technology in Forensic Science, National Academy Press, Washington, D.C., 1992, pp. 1–185.

Ballantyne et al., *DNA Technology and Forensic Science*, Banbury Report 32, Cold Spring Harbor Laboratory Press, Cold Spring Harbor, N.Y., 1989, pp. 1–368.

Chemical Abstracts, vol. 101, 1984 No. 1 24106n, Proc. Natl. Acad-Sa, USA 1984 81 (15), 4884–8 (eng).

Chemical Abstracts, vol. 98, 1983 No. 12 302 mm Proc Natl. Acad. Sci., USA 1982 79 (21) 6593–7, (eng).

Chemical Abstracts vol. 101, 1984, No. 66997r, Genetika, 1984, 20 (5) 738–45 (Russ).

Chemical abstracts vol. 100, 1984, No. 186642x Nucleic Acids res, 1984, 12 (6) 2887–900 (eng).

Chemical abstracts vol. 100, 1984, No. 62783z J Mol appl Genet 1983 2 (3) 237–47, (eng).

Chemical abstracts vol. 98, 1983 No. 105243h, Halmatologica 1982, 67 (5) 655–70 (eng).

Chemical abstracts vol. 99, 1983 No. 188876m, Gene 1983, 23 (3) 355–67 (eng).

Jeffreys et al, The Embo Journal, vol. 3, 1984, pp. 439–446.

Akaboshi (I), Gene, vol. 40, 137–140 (1985).

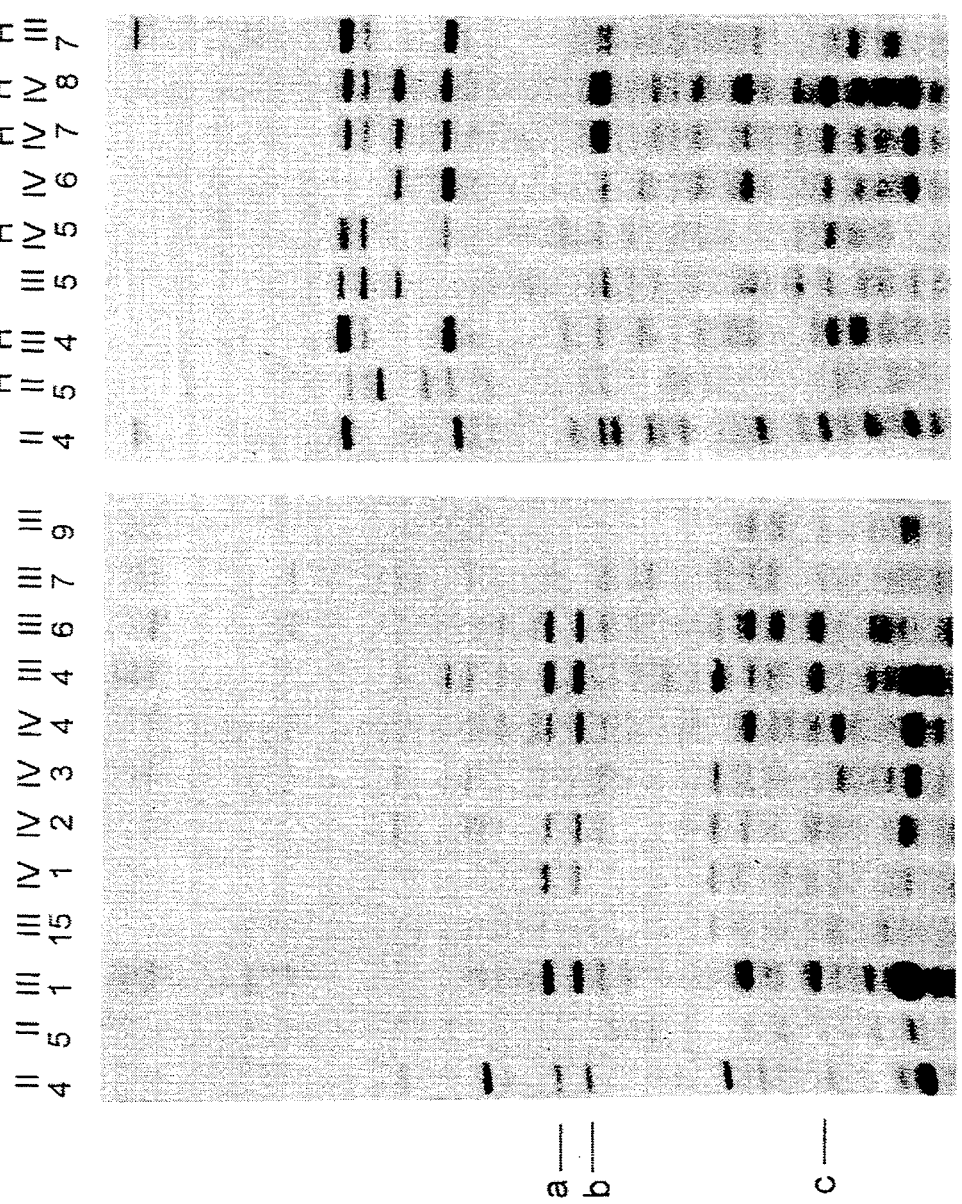

x33.6   x33.15 x33.6   x33.15

METHOD OF CHARACTERIZING GENOMIC DNA BY REFERENCE TO A GENETIC VARIABLE

This is a continuation of application Ser. No. 07/228,523, filed on Aug. 4, 1988, which was abandoned upon the filing hereof which is a divisional of appln. Ser. No. 06/783,790, filed Oct. 3, 1985, now abandoned.

BACKGROUND OF THE INVENTION

1. Field of the Invention

The invention relates to polynucleotides which can be labelled to serve as probes useful in probing the human or animal genome, and to a method of identifying genomic DNA using such probes. The method of identification is useful, for example, in paternity and maternity testing, forensic medicine and in the diagnosis of genetic diseases, and cancer.

2. Description of the prior art

The main prior method of identifying genetic variation in genomic DNA is by detecting restriction fragment length polymorphisms (RFLPs). See, for example, the identification of the locus of the DNA defect responsible for Huntington's chorea disease, by J. F. Gusella et al., Nature 306, 234–238 (1983), and the analysis of pre-disposition to retinoblastoma by W. K. Cavanee et al., Nature 305, 779–784 (1983).

Most RFLPs result from small scale changes in DNA, usually base substitutions, which create or destroy specific restriction endonuclease cleavage sites. Since the mean heterozygosity of human DNA is low (approximately 0.001 per base pair), restriction endonucleases will seldom detect a RFLP at a given locus. Even when detected, most RFLPs are only dimorphic (presence and absence of a restriction endonuclease cleavage site) with a heterozygosity, determined by allele frequencies, which can never exceed 50% and which is usually much less. As a result, all such RFLPs will be uninformative in pedigree analysis whenever critical individuals are homozygous.

Genetic analysis could be considerably simplified by the availability of probes for hypervariable regions of DNA which show multiallelic variation and correspondingly by high heterozygosities. The first such region was isolated by A. R. Wyman et al., Proc. Nat. Acad. Sci. U.S.A. 77, 6754–6758 (1980), by chance from a library of random segments of human DNA. The structural basis for multiallelic variation at this locus is not yet known. Subsequently, and again by chance, several other highly variable regions have been discovered near the human insulin gene, [G. I. Bell et al., Nature 295, 31–35 (1982)], zeta-globin genes [N. J. Proudfoot et al., Cell 31, 553–563 (1982) and S. E. Y. Goodbourn et al., Proc. Nat. Acad. Sci. U.S.A. 80, 5022–5026 (1983)] and c-Ha-ras-1 oncogene [D. J. Capon et al., Nature 302, 33–37 (1983)]. In each case, the variable region consists of tandem repeats of a short sequence (a "minisatellite") and polymorphism is due to allelic differences in the number of repeats, arising presumably by mitotic or meiotic unequal exchanges or by DNA slippage during replication. The resulting minisatellite length variation can be detected using any restriction endonuclease which does not cleave the repeat unit.

The present inventor and his colleagues have previously described a short minisatellite comprised of four tandem repeats of a 33 bp sequence in an intron of the human myoglobin gene, see P. Weller et al., EMBO J. 3, 439–446 (1984). It was noticed that the 33 bp repeat showed weak similarity in sequence to the above-mentioned other human minisatellites previously characterised. The paper speculated that the minisatellite regions might arise by transposition. If the 33 bp repeat in the human myoglobin gene were transposable then it might provide a probe for tandem repetitive regions of the human genome which are frequently associated with multiallelic polymorphism due to repeat number variation.

3. Additional, Unpublished, Background Information

Human genomic DNA was probed with a DNA probe comprising tandem repeats of the 33 bp sequence from the myoglobin gene. Polymorphic variation was observed at several different regions in the genomic DNA of 3 individuals (father, mother and daughter), the variation occurring in the size of larger fragments (2–6 kb). The data were consistent with stably inherited polymorphism due to length variation of more than one minisatellite regions.

SUMMARY OF THE INVENTION

Further research has revealed that it is possible to probe genomic DNA in such a way as to display variability in the minisatellite or hypervariable regions fax more effectively than by using the myoglobin gene 33 bp-repeat probe.

The present invention is based on the discovery that many minisatellites in human or animal genomic DNA contain a region of DNA which has a high degree of homology between different minisatellites. This common core region is of short length, approximately 16 base pairs. It has now been found that a probe having as its essential constituent a short core sequence of nucleotides tandemly repeated at least three times will serve to detect many different minisatellite regions in the genomic DNA and with such a fine degree of precision as to enable individuals to be identified or fingerprinted by reference to variations in their DNA in these regions. Such an excellent result is highly unexpected, since previous research has produced probes which are only capable of detecting single minisatellite regions in genomic DNA. These prior probes lead to a better degree of differentiation than that given by RFLPs, but not to a fingerprint which is in essence unique for an individual. Remarkably, it has been found that the present core probe is capable of differentiating DNA by reference to more than one minisatellite region or hypervariable locus, and it is this discovery which lends an unusual degree of unobviousness to the inventive act, making this an invention of fundamental scientific novelty and importance.

From knowledge of a core sequence, DNA probes can be produced which have the property of hybridising with minisatellite regions from a variety of loci in the genome. However the mere recognition or identification of a particular core sequence is insufficient in itself for the production of an operable probe. It is also necessary to produce a polynucleotide containing tandem repeats of the core sequence or derivatives thereof. Such probes may be isolated as minisatellites from human or animal DNA, or instead may be constructed by synthetic techniques. It is also important to establish the additional constraints which affect successful hybridisation. These include knowledge of the degree of homology with the consensus core which may be tolerable and also the tolerable length of any non-core DNA within and without the repeating unit as a whole.

Thus the invention involves the recognition and discovery:

(1) that knowledge of any one core sequence can be utilised in this way. It involves the further appreciation:
(2) that by investigating different hypervariable loci in a genome, different core sequences can be found having the necessary degree of consensus;
(3) that a family of DNA probes can be accumulated which will recognise different spectra of polymorphisms;
(4) that a particular genetic classification may be more successfully accomplished with one probe than another;
(5) that by the use of more than one probe in any one classification, the probability of identification is amplified;
(6) that by further study of a first generation of successful probes, simpler and more successful probes can be produced e.g. by synthesis.

Thus according to a first aspect of the invention there is provided a method of making a polynucleotide having polymorphic minisatellite-length-specific binding characteristics comprising:

(i) identifying a natural tandem repeat sequence in DNA which is capable of limited hybridisation to other polymorphic DNA regions,
(ii) identifying a natural consensus core sequence of the repeat sequence putatively responsible for such binding, and
(iii) isolating or artificially building a perfect or imperfect tandem repeat sequence derived from the natural consensus core sequence having minisatellite binding properties which exhibits lower genome-locus-specificity and higher polymorphic fragment acceptance than the natural repeat sequence.

The core component of the probe can be defined in various ways founded on the same underlying principles. The most fundamental underlying principle is that the repeat sequence of the probe shall consist of or include a nucleotide sequence from a common core region, common to minisatellites of human or animal genomic DNA. The common core region is "common" in the sense of displaying a high degree of consensus, e.g. at least 80%, as between one minisatellite and another. These minisatellites are detectable e.g. by probing genomic DNA fragments with the myoglobin gene 33 bp repeat sequence, to yield hybridised fragments herein referred to as "λ33-positive" fragments. These fragments and the 33 bp repeat of the myoglobin gene contain an approximately 16 bp common core sequence. The λ33-positive fragments can themselves be used as probes of genomic DNA to generate further fragments which also have the common core sequence, although possibly with some small variation thereof.

Another principle is that the core nucleotide sequence shall be not so short that it fails to hybridise effectively to the minisatellite regions of the sample DNA, nor so long that it fails to detect the polymorphisms well, e.g. that it becomes too much like the 33 bp tandem repeat in the myoglobin gene. Generally, the core should have from 6 nucleotides up to the maximum found in the common core of minisatellites, approximately 16. The repeat sequence of the probe need not consist entirely of the core but can contain a small number of flanking nucleotides on either side of the core sequence. The repeating units need not be exact repeats either as to number or kind of nucleotides and either as to the core or non-core components of the repeating units. It is, however, convenient to describe and define them herein as repeating units, notwithstanding that this is an approximate term. The block of n repeating units can be flanked on either side by any nucleotide sequence, the extent and kind of which is ordinarily irrelevant.

Polynucleotides of the invention include specifically those defined in each of the following ways:

FIRST DEFINITION

Polynucleotides having the general formula, read in the 5'→3' sense $$H.(J.core.K)_n.L \qquad (1)$$

wherein:

"core" represents a sequence having at least 6 consecutive nucleotides, selected from within any of the following sequences read in the same sense:

$$GGAGGTGGGCAGGAXG \qquad (2)$$

$$AGAGGTGGGCAGGTGG \qquad (3)$$

$$GGAGGYGGGCAGGAGG \qquad (4)$$

$$T(C)_mGGAGGAXGG(G)_pC \qquad (5A)$$

$$T(C)_mGGAGGA(A)_qGGGC \qquad (5B)$$

wherein:

X is A or G, Y is C or T, m is 0, 1 or 2, p is 0 or 1, q is 0 or 1, n is at least 3;

J and K together represent 0 to 15 additional nucleotides within the repeating unit; and H and L each represent 0 or at least 1 additional nucleotide flanking the repeating units, and provided that:

(i) "core" and J and K do not necessarily have the same sequence or length in each (J.core.K) repeating unit;
(ii) "core" can also represent a variant core sequence;
(iii) total actual core sequences in all n repeating units have at least 70% homology with total "true" core sequences as defined above with respect to formulae 2 to 5 in the same number n of repeating units;

and polynucleotides of complementary sequence to the above.

SECOND DEFINITION

Polynucleotides having the general formula $$H. (J.core.K.)_n.L \qquad (1)$$

wherein:

"core" represents a sequence of from 6 to 16 consecutive nucleotides, read in the same 5'-3' sense, selected from (1) the 5'→3' common core region of a first human or animal minisatellite obtained by probing human or animal genomic DNA with a probe DNA containing a myoglobin tandem repeat sequence of approximately 33 nt per repeat unit (2) the 5'→3' common core region of a second human or animal minisatellite obtained by probing human or animal DNA with a probe DNA containg a tandem repeat sequence comprising the common core region of the first minisatellite, and (3) and 5'→3' common core region of a third human or animal minisatellite obtained by probing human or animal genomic DNA with a probe DNA containing a tandem repeat sequence comprising the common core region of the second minisatellite, each said tandem repeat sequence being a repeat of at least 3 units, and polynucleotides of complementary sequence to the above.

THIRD DEFINITION

Polynucleotides having the general formula $$H.(J.core.K.)_n.L \tag{1}$$

wherein:

"core" represents any of the sequences having at least 6 consecutive nucleotides from within a common core region of minisatellites of human or animal genomic DNA which displays at least 75%, preferably 80% consensus;

"core" does not necessarily have the same sequence in each repeating unit and all other symbols are as defined above, and polynucleotides of complementary sequence to the above.

FOURTH DEFINITION

Polynucleotides having at least three repeats of a sequence of from 6 to 36 nt including a consecutive (5'→3') core sequence selected from within:

$$(5') \text{ GPGGGCWGGWXG } (3') \tag{6}$$

where P=not G, W=A or T and X=A or G or a variant thereof, provided that the total actual core sequences in all repeats have at least 70% homology with the total "true" core sequences defined with respect to formula (6) in the same number of repeats, and polynucleotides of complementary sequence to the above.

In the above formulae and throughout the sequence are shown in the usual notation 5'→3'.

The invention includes polynucleotides of DNA, RNA and of any other kind hybridisable to DNA. The polynucleotides as defined above are unlabelled and can be in double stranded (ds) or single stranded (ss) form.

The invention includes labelled polynucleotides in ss-form for use as probes as well as their labelled ds-precursors, from which the ss-probes can be produced.

They are preferably $^{32}$P-radiolabelled in any conventional way, but can alternatively be radiolabelled by other means well known in the hybridisation art, labelled with biotin or a similar species by the method of D. C. Ward et al., as described in Proceedings of the 1981 ICN-UCLA Symposium on Developmental Biology using Purified Genes held in Keystone, Colorado on Mar. 15–20, 1981 vol. XXIII 1981 pages 647–658 Academic Press; Editor Donald D. Brown et al or even enzyme-labelled by the method of A. D. B. Malcolm et al, Abstracts of the 604th Biochemical Society Meeting, Cambridge, England (meeting of 1 Jul. 1983).

Thus according to another aspect of the invention there is provided a polynucleotide probe useful in genetic origin determinations of human or animal DNA-containing samples comprising, with the inclusion of a labelled or marker component, a polynucleotide comprising at least three tandem repeats (including variants) of sequences which are homologous with a minisatellite region of the human or animal genome to a degree enabling hybridisation of the probe to a corresponding DNA fragment obtained by fragmenting the sample DNA with a restriction endonuclease, characterised in that:

a) the repeats each contain a core which is at least 70% homologous with a consensus core region of similar length present in a plurality of minisatellites from different genomic loci;

b) the core is from 6 to 16 nucleotides long;

c) the total number of nucleotides within the repeating unit which do not contribute to the core is not more than 15.

The invention also includes a method of identifying a sample of human or animal genomic DNA which comprises probing said DNA with a probe of the invention and detecting hybridised fragments of the DNA.

This aspect of the invention may involve:

fragmenting total DNA from a sample of cellular material using a restriction endonuclease, hybridising highly variable DNA fragments with a probe as defined above which contains, in addition to a labelled or marker component, a repeated core component, and determining the label or marker concentration bound to DNA fragments of different length, or more generally to bands of different molecular size.

Normally the fragmented DNA is sorted or segregated according to chain length, e.g. by electrophoresis, before hybridisation, and the marker concentration is sensed to obtain a characteristic pattern, individual elements of which are of specific genetic origin.

DEFINITIONS

The following definitions used in the present invention and the above-mentioned earlier specifications may be of assistance.

Hypervariable

A region of human or animal DNA at a recognised locus or site is said be hypervariable if it occurs in many different forms e.g. as to length or sequence.

Restriction Fragment Length Polymorphism (RFLP)

Is genetic variation in the pattern of human or animal DNA fragments separated after electrophoresis and detected by a probe.

Minisatellite

A region of human or animal DNA which is comprised of tandem repeats of a short DNA sequence. All repeat units may not necessarily show perfect identity. (Probes of the invention comprise minisatellites which are polymorphic).

Polymorphic

A gene or other segment of DNA which shows variability from individual to individual is said to be polymorphic.

Core (Sequence)

Originally used in the sense of consensus core sequence, but extended to any repeated or variant sequence derived therefrom.

Consensus Core (Sequence)

A sequence which can be identified as a substantial or perfect match between the repeat units of two or more minisatellites of differing origin or loci.

Repeat (Sequence)

A sequence which is a perfect or imperfect tandem repeat of a given core sequence or segment containing the core sequence.

Defined Core (Sequence)

A core sequence fully consistent with one of formulae (2) to (8) within its own length.

Variant (Core Sequence)

An actual core sequence which differs from a defined core sequence to a minor extent (>50% homology).

Perfect Repeat (Sequence)

A sequence which is an exact tandem replication of a given core sequence or of a segment containing the core sequence.

Imperfect Repeat (Sequence)

A sequence in which at least one unit differs in base pair substitution and/or length from at least one other unit. (There will normally be at least three tandem repeats in a probe sequence within which there will normally be at least one defined core sequence and at least one variant).

% Homology

In comparing two sequences of the same length, the number of base pairs (bp) less the number of bp substitutions in one necessary to give the other, as a percentage of the number of bps.

Nucleotide (nt) and base pair (bp) are used synonimously. Both can refer to DNA or RNA. The abbreviations C, A, G, T refer conventionally to (deoxy)cytidine, (deoxy)adenosine, (deoxy)guanosine and either deoxythymidine or uridine.

The tandem repeat sequence (artificial or a natural isolate) may thus be a perfect repeat but is more preferably an imperfect repeat. Preferably at least two repeats are imperfect repeats of the consensus core sequence. There are preferably at least three repeats and more preferably at least 7 in the probe sequence.

Production of a probe may involve isolation of a natural minisatellite by cloning and identification by DNA sequencing. It may also involve excision of the required core and its subsequent conversion into a tandem repeat, or the stimulation of unequal exchanges with core fragments of different origin. It may also include cloning of the polynucleotide.

On the other hand, the building step may include synthesising the identified consensus core sequence or a fragment thereof. The consensus core sequence preferably contains not less than 6 bp and preferably contains not more than 16 bp. A tandem repeat of the synthetic core is then constructed.

Naturally the polynucleotide may be the result of a succession of operations at different times following cloning of successful or partially successful intermediates and may include fragments of natural or synthetic origin, so that the end polynucleotide may bear little resemblence to the parent minisatellite.

The probes of the invention are useful in the following areas:
1. Paternity and maternity testing in man.
2. Family group varification in e.g. immigration disputes and inheritance disputes.
3. Zygosity testing in twins.
4. Tests for inbreeding in man.
5. General pedigree analysis in man.
6. Identification of loci of genetic disease in man, thereby enabling specific probes to be constructed to detect a genetic defect.
7. Forensic medicine
    (a) fingerprinting semen samples from rape victims
    (b) fingerprinting blood, hair and semen samples from e.g. soiled clothing
    (c) identification of human remains.
8. Cell Chimaerism studies, e.g. following donor versus recipient cells after bone marrow transplantation.
9. Livestock breeding and pedigree analysis/authentication. (This could include, for example, the routine control and checking of pure strains of animals, and checking pedigrees in the case of litigations involving e.g. race horse and dog breeding). Also to provide genetic markers which might show association with inherited traits of economic importance.
10. Routine quality control of cultured animal cell lines, checking for contamination of pure cell lines and for routine identification work.
11. Analysis of tumour cells and tumours for molecular abnormalities.
12. It is anticipated that the polynucleotides or probes derived therefrom have a potential use in plant breeding.

BRIEF DESCRIPTION OF THE DRAWINGS

FIGS. 8 and 8A show autoradiographs of DNA from a Gujerati pedigree produced for examination of possible coinheritance of minisatellite fragments and hereditary persistance of foetal haemoglobin (HPFH)

FIGS. 15 and 15A are autoradiographs showing DNA fingerprints obtained from forensic samples.

DESCRIPTION OF THE PREFERRED EMBODIMENTS

Figure 1:
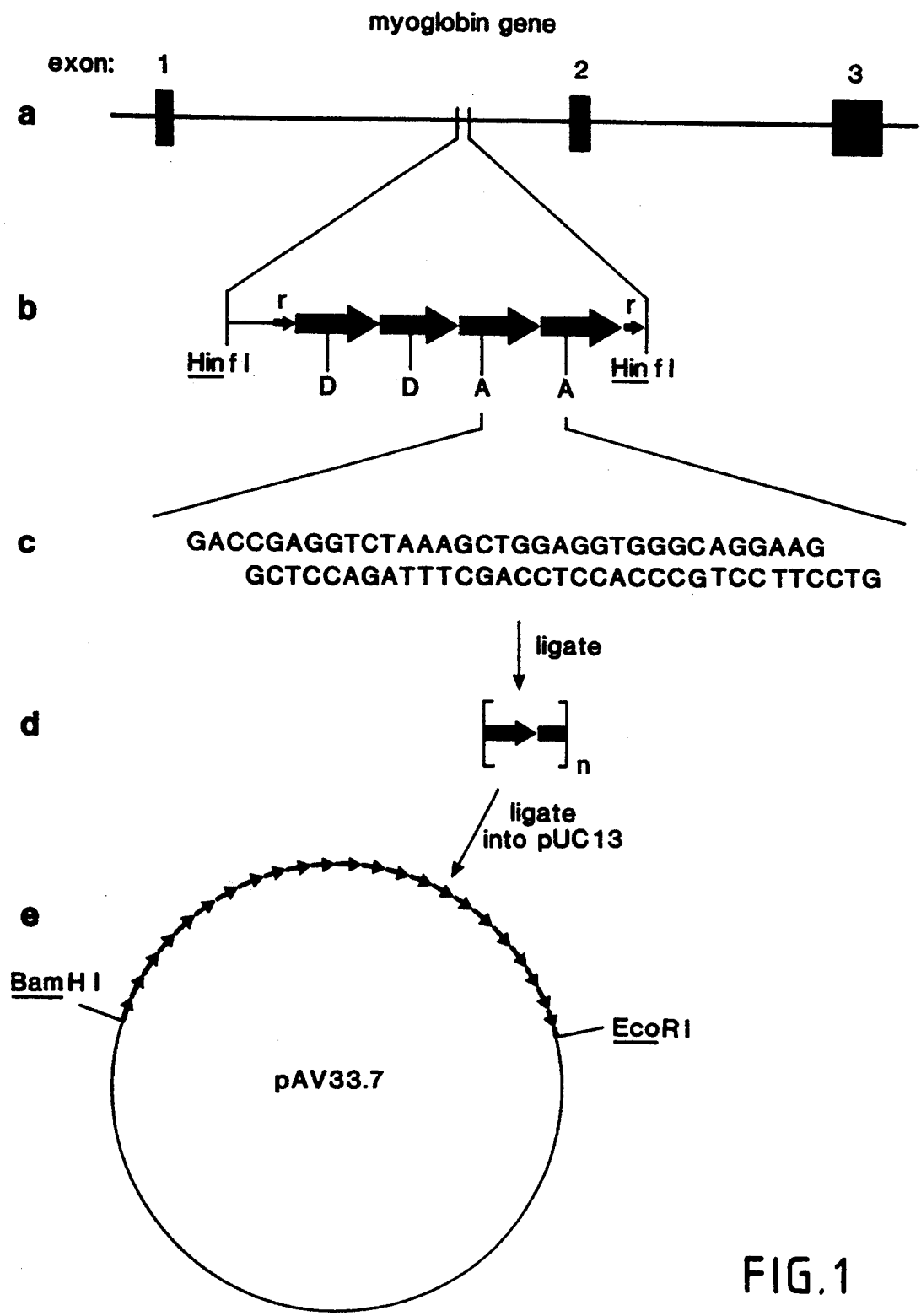
FIG. 1 is a schematic representation of the procedure of preparing a 33 bp repeat sequence of the myoglobin gene inserting it in a plasmid and cloning it.

A human genomic library of 10–20 kb Sau3A partial of human DNA cloned in phage λL47.1 was screened by hybridization with the 33 bp myoglobin repeat probe "pAV33.7". At least 40 strongly-to-weakly hybridizing plaques were identified in a library of $3 \times 10^5$ recombinants. A random selection of eight of these positive plaques was purified (λ33.1-15), and Southern blot analysis of phage DNA was used to show that in each recombinant the hybridizing DNA was localised within a unique short (0.2–2 kb) region of the recombinant. Sequence analysis showed that this region in each of the eight recombinants contains a minisatellite comprised of 3–29 tandem copies of a repeat sequence whose length ranged from 16 bp in λ33.15 to 64 in λ33.4. Most minisatellites contained an integral number of repeats. In λ33.6, the 37 bp repeat consisted in turn of a diverged trimer of a basic 12 bp unit. Each λ33 recombinant represented a different region of the human genome, as judged by the clone-specific DNA sequence flanking each minisatellite.

The eight cloned minisatellite regions were located within 0.5–2.2 kb HinfI DNA fragments, smaller than the polymorphic 2–6 kb DNA fragments which can be detected by pAV33.7 in HinfI digests of human DNA. To determine whether any of the cloned minisatellite regions were also polymorphic, $^{32}$P-labelled single-stranded DNA probes were prepared from suitable M13 subclones of each minisatellite and hybridized at high stringency to a panel of 14 unrelated British caucasian DNAs digested with HinfI. Typical hybridization patterns show that under these hybridization conditions, each probe detects a unique region of the human genome, and that three of these regions are highly polymorphic.

Fuller details of the above procedure are given in the Examples.

Referring now to the definitions of the polynucleotides set out above, the definitions conform to the general formula $$H.(J.C.K.)_n.L \tag{8}$$

wherein C represents a core sequence and the other symbols are as defined above. In all definitions the cope sequence in one unit can be the same or different from the next. For example, it might contain an extra nucleotide or two, lack a nucleotide or two or differ in (say) 1 to 4 nucleotides, as compared with a consensus sequence applicable to the repeating units as a whole.

The core can be defined in various ways. A general definition can be obtained by reference to the procedure by which core sequences can be identified. A minisatellite region of genomic DNA is compared with a sequence such as $$\text{GGAGGTGGGCAGGAXG} \tag{2}$$

An x-nucleotide long sequence taken from the minisatellite which shows the greatest homology with an x-nucleotide selected from all possible x-nucleotide long sequences comprised in formula (2) is taken to be the core sequence. That is, of course, a very narrow way of defining the core, and should result in 1 or a few cores of 6 nucleotides long, 1 or a few 7 nucleotides long and so on up to 16 nucleotides long, ("a few" because in some cases there will be more than one sequence of greatest, e.g. 100%, homology). To reflect the discovered possibility of variation in the core sequence so defined, it is postulated that there can be variation to an extent that all n repeating units have on average at least 70% homology of their cores with cores as defined above. Any flanking sequences, J and K, within the repeat unit, are not included in the reckoning for homology purposes, the comparison being solely between cores. The cores defined can have various lengths and can be "mixed", i.e. in some repeating units be homologous with (say) GGGCAGGAXG of formula (2) and in others be homologous with (say) GGGCAGGTGG of formula (3). Variants should therefore be considered in terms of homologies with $(core)_n$ rather than necessarily with "core" itself.

The "first" definition defined earlier is derived from the above considerations but simplified in that the core is defined as a sequence of any length from 6 up to the maximum of 12–16, as the case may be, in the formulae (2) to (5) shown. There is a similar provision for variants.

The "second" definition defines the core in terms of successive hybridisation steps, each of which can produce additional minisatellite fragments. It will readily be seen that by performing a sufficient number of hybridisations on extensive libraries of human genomic DNA, examining a sufficient number of hybridised fragments, making probes from them, again probing the genomic DNA and so on, theoretically up to an infinite number of times, it should be possible to arrive at a range of consensus core sequences which is widely represented in minisatellite DNAs. In practice, it is not expected that these operations would have to be done a very large number of times and on a vast scale to arrive at a sufficiently wide consensus core region, and therefore (arbitrarily) only 3 probing operations are included in the definition.

In the "third" definition, W represents the core and looks to the possibility of a widely shared consensus core region with variations thereon not departing by more than 25% (say, 4 nucleotides in 16). Having thus defined a core region of up to approximately 16 nucleotides with possible variation up to 25%, the core W is defined as a sequence of at least 6 consecutive nucleotides from within that region.

The "fourth" definition involves a redefined consensus core formula (6) obtained from studies involving synthetic polynucleotides.

These studies have led to further definitions of shorter core sequences.

Thus preferably the consecutive (5'→3') sequence:

$$\text{PGGGCWG} \tag{7}$$

is conserved in all repeating units, P and W having the meanings given in the fourth definition above. P is preferably T; W is preferably A.

Preferably also the consecutive (5' 3') sequence:

TGGGCA             (8)

is conserved in all repeating units.

According to another aspect there is provided polynucleotides having at least three repeats including the consecutive 5'→3' core sequence

GGPGGGCWGGWXG             (7)

where P=not G, W=A or T and X=A or G or a variant thereof, provided that the total actual core sequences in all repeats have at least 70% homology with the total "true" core sequences defined with respect to formula (7) in the same number of repeats, and polynucleotides of complementary sequence to the above.

In all the definitions above, the core is at least 6 nucleotides long, more preferably at least 7 or 8 and most preferably 12 or more e.g. 14 to 16. The sequence GGGCAGGAXG of formula (2) (the end 10 nucleotides at the 3' end) is a sequence of high consensus and appears particularly promising. Preferably the core comprises at least 6 and more preferably all 10 nucleotides of this sequence.

The variant cores preferably have at least 75% and more preferably at least 80 or 85% homology.

The flanking sequences J and K within each repeating unit are preferably omitted or kept short, e.g. to 0, 1 or 2 nucleotides on each side and preferably J and K together should not exceed 20, more preferably 15. The total number of nucleotides in the sum of J+core+K, within a repeating unit should preferably not exceed 36, and more preferably 31 and most preferably 25.

The number of repeat units n is preferably at least 10, conveniently 10 to 40, but in principle n can be any number, even up to 10,000.

The flanking sequences H and L are irrelevant. They can be omitted or can be present in any number of nucleotides e.g. up to 20,000 although to work with such a long probe would not ordinarily be sensible. They can contain ds-DNA even when the repeat sequences are of ss-DNA.

The method of identification can make use of any known techniques of probing, most usual of which is to cleave the sample DNA with restriction enzyme(s) (one or more, as appropriate) which do not cleave the tandem repeat sequences or cleave only to an irrelevant extent not interfering with their ability to be probed.

The following Examples illustrate the invention. Temperatures are in °C.

EXAMPLE 1

(1) Construction of a Probe Containing Long Tandem Repeat Sequences, from the Human Myoglobin Gene The construction of this probe is illustrated schematically in FIG. 1 of the drawings showing five stages, labelled (a) to (e). The starting myoglobin gene (a) is described by P. Weller et al, EMBO J., 3, 439–446 (1984). As shown therein, the gene has a region located in the first intron, comprising four repeats of a 33 bp sequence flanked by almost identical 9 bp sequences (r in FIG. 1). This region was isolated in a 169 bp HinfI fragment (b), which was end-repaired and amplified by cloning into the SmaI site of the plasmid pUC13, see J. Vieira et al, Gene 19, 259–268 (1982). A monomer was isolated (c) by cleaving the third and fourth repeats with the restriction endonuclease AvaII (A). (A single base substitution in repeats 1 and 2 eliminates this site and creates instead a DdeI (D) site). Ligation of the 83 bp monomer via the non-identical AvaII sticky ends produced a head-to-tail polymer (d), having an unknown number (n) of repeating units. Polymers containing at least 10 repeats were isolated by preparative agarose gel electrophoresis, end-repaired, ligated into the SmaI site of pUC13 and cloned in E.coli JM83, see J. Vieira et al, supra. The structure of the polymeric DNA insert in the resultant plasmid, designated pAV33.7, (e), was confirmed by excision of the insert at the polylinker with BamHI plus EcoRI, fill-in labelling with $\alpha$-$^{32}$P-dCTP at the BamHI site, and partial digestion with AvaII. Labelled partial digest products were resolved by electrophoresis on a 2% agarose gel. pAV33.7 was found to contain 23 repeats of the 33 bp monomer contained in a 767 bp BamHI-EcoRI fragment as shown (e).

(2) Sequencing of a Selection of Minisatellite Regions of the Human Genome by the Myoglobin 33 bp Repeat Probe A library of 10–20 kb human DNA fragments cloned in bacteriophage $\lambda$L47.1, see P. Weller et al, supra and W. A. M. Loenen et al, Gene 20, 249–259 (1980), was screened by hybridization with the 767 bp pAV33.7 insert described in step (1) above, $^{32}$P-labelled in vitro by the method of P. Weller et al, supra. A selection of eight positive plaques was purified to give recombinants designated $\lambda$33.1-15. Each such phage DNA was digested singly with HinfI or HaeIII, electrophoresed through a 1.5% agarose gel, and 33-repeat related sequences therein were localised by Southern blot hybridization with pAV33.7 DNA. Each recombinant Save a single "$\lambda$33-positive" HinfI and HaeIII fragment, except for $\lambda$33.4 and 11 which gave no detectable positive HaeIII fragments (due to a HaeIII cleavage site being present in the repeat regions in these recombinants). The $\lambda$33-positive HinfI and HaeIII fragments were isolated by preparative gel electrophoresis, end-repaired if necessary, and blunt-end ligated into the SmaI site of the double-stranded DNA M13mp8, J. Messing et al, Gene 19, 269–276 (1982). Positive ss-M13 recombinants were isolated after transformation into E.coli JM101 and sequenced by the dideoxynucleotide chain-termination method. All $\lambda$33-positive fragments contained a tandem repetitive region, which in some cases could be sequenced directly. In other cases where the repeat region was too far from the sequencing primer site, the M13 inserts were shortened by cleavage with restriction endonucleases and resequenced.

The structure of the $\lambda$33-positive fragments is shown below in the form of 8 maps designated $\lambda$33.1, 33.3, 33.4, 33.5, 33.6, 33.10, 33.11 and 33.15. The actual restriction enzyme used and lengths of fragments in nucleotides were $\lambda$33.1: HaeIII, 2000; 33.3: HinfI, 465; 33.4: HinfI, 2000; 33.5: HinfI, 1600; 33.6: HaeIII, 720; 33.10: HaeIII, 720; 33.11: HinfI, 1020; $\lambda$33.15: HinfI, 1220. Each map shows repeated sequence of bases in upper case script above a rectangular box. The "repeats" are not invariably complete in terms of number of bases, and some differ by substitution of bases. Therefore, the repeated sequence shown above the box is a consensus sequence (con), being that with which most of the sequencing done is in agreement. The box shows how the repeats differ from the consensus. Blanks in the box denote found agreement. Base symbols A, C, G, T in the box denote

5 lambda 33.1

```
       ccgtgtcacccacaagctctgggggtgggggtacgatgttcaggaaa
con  AAGGGTGGGCAGGAAGTGGAGTGTGTGCCTGCTTCCCTTCCCTGTCTTGTCCTGGAAACTCA
```

|     |                                              |
|-----|----------------------------------------------|
| 1   |                                              |
| 2   |                                              |
| 3   |                                              |
| 4   |           G          >>>>>>>>>>>>>>>>>>>>>>> |
| 23  | <<<<<<<<<<<<<<<<<<<<<<<<<<<<<<<<<<<          |
| 24  |                                              |
| 25  |           G                                  |
| 26  |           G                                  |

```
gcagttgtggcatcccaucgtggagaaagcaagcccctgccccggcagg
``` lambda 33.3

```
cctttcccttcctgccgtcagccctggaaaaggttgtgggggagaaag
    con  CCGGGAGGTGGGCCAGGAAXGGGTGGAGXXGGG
```

|   |     |   |   |   |      |      |   |
|---|-----|---|---|---|------|------|---|
| 1 | G   |   |   | G | AATA | CGA  |   |
| 2 | TTT | A | G |   | AA   | GGATA|   |
| 3 |     | A |   |   | G    | AAG  | T |
| 4 | G   |   | A |   | G    | GG   | C |
| 5 |     | A | A |   | G    | AA   |   |
| 6 |     |   | T |   | A T  | GAAA | A |

```
gtagagaggtgaggggtggttcctccatggaggagacctagcccactg
``` lambda 33.4

```
              ggcagggatgtgggaccgggccagacccagctgctgagcacgcgccacc
con  TGCAGGGTGGGGAGGGCAG-AAAGAACCCCCGCGTGXAGGGGCACC-CACATCTGGGGCCACAGGA
```

|    |                                                              |
|----|--------------------------------------------------------------|
| 1  | A--       G     G    TGT  -------------------------------    |
| 2  | G A  A                       A    A-                         |
| 3  |                              -    - A                        |
| 4  |                              -    - A                        |
| 5  |              >>>>>>>>>>>>>>>>>>>>>>>>>>>>>>>>>>              |
| 10 | <<<<<<<<<<<<<<<<<<<<<<<<<<<<<<<<<<<<<                        |
| 11 | G             G        - G         T     G                   |
| 12 | G             G        - G                                   |
| 13 |                        - G         T     G                   |
| 14 |                             ---------------------            |

```
cctaagcaggttctggtggcctcctggctgggtgtaggcagaggctggct
``` lambda 33.5

```
gagctaatgtttcgggggctgcactgggtcatgtgagtaatcatgagggc
           con  YGGGCAGG-AGGGGGAGG
```

|    |    |     |     |     |
|----|----|-----|-----|-----|
| 1  | T  | CAG |     |     |
| 2  | C  |     | – A |     |
| 3  | C  | A   | –   |     | –
| 4  | T  |     | – A |     | A
| 5  | T  | TG  | – – – – – – G |  |
| 6  | T  |     | – A T |   |
| 7  | T A |    | –   | A G |
| 8  | T  |     | – A |     |
| 9  | T  |     | G   |     |
| 10 | C  | T   | –   |     |
| 11 | C  | T   | T – | T   |
| 12 | CA |     | –   |     |
| 13 | CA | A   | –   |     |
| 14 | CC | – A | –   | T   | ccagtatcctgggaattcgtaatcatggtcatagctgtttcctgtgtgaa lambda 33.6 tacaatgtgagtagaggagacctcacatttgaccttggaaagt
con TGGAGGAAGGGCTGGAGGAGGGCTCCGGAGGAAGGGC
    – – – – – – – – > – – – – – – – – >   – – – – – – – – – >

|    |                              |
|----|------------------------------|
| 1  |                        A     |
| 2  |                        A     |
| 3  |                              |
| 4  |                              |
| 5  |                              |
| 6  |                              |
| 7  |                              |
| 8  |  – – – – – – – – – – – – – – – – – – –  |
| 9  |                              |
| 10 |                              |
| 11 |           > > > > > > > > >  |
| 17 | <                            |
| 18 |                       A    – | ggttgctcctcactctgtggtctttgtctgtccagaccttcccttcttgg lambda 33.10 aagcatcaaacagggctgggtgtttagtccttttccacatctggctcca
con GAAGTAGGAGGTGGCTGGAGTGGGCAGGCAGGACTG–TCCCC

|   |   |   |   |   |     |   |   |
|---|---|---|---|---|-----|---|---|
| 1 | G | G |   |   | CCA |   | – |
| 2 | G | G | C | A |     |   |   |
| 3 |   |   |   |   |     |   |   |
| 4 |   | C |   |   |     |   |   |
| 5 |   |   |   | A |     | G | C | aggagacactgccctggtggctctgacccctgcagcctcctatgctcta lambda 33.11 caggaggaggcagaaagtggcagaggagccctccaggccggagggacacg
    con CAGGAAGCAGTGAGGCCCTGGGCTGGTGGTGGG

| 1 |  |
|---|--|
| 2 |  |
| 3 |  | cacgatgcttggggcagcactcacacacagtaagtgcccaagtcaaatga lambda 33.15 ggtggttttcaagaaagcgtttcatgcaatttgctttaaatgttaggaaa
      con  GAGGTGGGCAGGTGGA

| # | | | | | | |
|---|---|---|---|---|---|---|
| 1 | — | — | — | — | — | |
| 2 | T | | | | | |
| 3 | T | | | | | |
| 4 | | | A | | | |
| 5 | | | | | | |
| 6 | | | | | | |
| 7 | | | | | | |
| 8 | | | | | | |
| 9 | | | A | | | |
| 10 | T | | | | | |
| 11 | | | | | | |
| 12 | | | | | | |
| 13 | — | — | | | | |

| 14 | T | | | | | |
|---|---|---|---|---|---|---|
| 15 | | | A | | | |
| 16 | | | | | | |
| 17 | | | | | | |
| 18 | | | | | | |
| 19 | | | | | | |
| 20 | | | | | | |
| 21 | | | A | | | |
| 22 | T | | | | | |
| 23 | | | | | | |
| 24 | | | | | | |
| 25 | — | — | | | | |
| 26 | | | | | | |
| 27 | | | | | | |
| 28 | | | | | | |
| 29 | | | | | | A | aatacctacagatgaggtgtgtgcttattctctgtgcaagatttcagagt substitution by that base for the one shown above it in the consensus sequence. X=A or G. Y=C or T. —=a missing nucleotide compared with the consensus. >>><<< (herring-bone) symbols indicate that the sequencing has not yet been done, although it is clear from autoradiographs radiographs of the sequencing gels that the sequence is a "repeat" of the consensus (using the term "repeat" of course, in the same approximate manner as above). Fragments λ33.3, 33.5, 33.10, 33.11 and 33.15 have been fully sequenced, the others partly sequenced. The numbers underneath "con" at the lef-hand side of the boxes are the repeat numbers of the sequences. The bottom number in this column indicates the number of repeats. Thus, λ33.1 contains 26 repeats of a 62 nucleotide (nt) sequence shown in upper case script above the box. The sequence shown in lower case script at the top and bottom of each map is flanking sequence lying respectively to the 5' and 3' sides of the repeat sequence block, and these flanking sequences are not repeated. In other words, the structure is analogous to that of random copolymer represented by the flanking sequences, in which units of block copolymer, represented by the tandem repeats, appear.

(3) Discovery and Identification of a Common, Short "Core" Sequence Located within and Shared by the Repeat Sequence of Each λ33-Positive Fragment The repeat sequence of each region was compared with the myoglobin 33 bp repeat sequence in pAV33.7, and with its reverse complement, using dot matrix analysis. Very remarkably, there was found a single, small unambiguous region of sequence similarity between the myoglobin 33 bp repeat sequence and the consensus repeat sequences of the λ33-positive fragments. The same region was shared by the repeats of all eight λ33 fragments and will be called the "common core". The chart below shows the comparison.

In the chart, the whole of each consensus sequence as determined in step (2) above is shown. These are the portions which tandemly repeat in the myoglobin 33 bp probe and in the λ33-positive fragments isolated from human genomic DNA. The chart shows the common core region as 16 nucleotides long in upper case script.

|  |  | common core region |  |
|---|---|---|---|
| 33 bp myoglobin | ctaaagct | GGAGGTGGGCAGGAAG ▼ | gaccgaggt |
| λ33.1 | cctgtcttgtcctggaaacta | ▼a a gGGTGGGCAGGAAG | tggagtgtgtgcctgcttccctt |
| λ33.3 | xxgggccg | GGAGGTGGGCAGGAAX | gggtggag ▽ |
| λ33.4 catctggggccacaggatgcaggg | | t G gGGa GGGCAG aAAG ▽ | aaccccgcgtgxaggggcaccca |
| λ33.5 | g | GGAGGYGGGCAGGAGG ▼ | |
| λ33.6* | aggaagggct | GGAGG aGGGC t GGAGG | agggctccgg ▼ |
| λ33.10 | gtaggaggtggct | GGA—GTGGGCAGG c AG ▼ | gactgtccccgaa |
| λ33.11 | ccctgggct | GG t GGTGGGCAGGAAG ▽ ▽ | cagtgaggc |
| λ33.15 | | aGAGGTGGGCAGG t GG | |
| common core region | 5' — | GGAG<u>GTGGGCAGGA</u>XG | — 3' |

*This sequence is a trimer, so the flanking regions contribute to the core.

Again, X=A or G, Y=C or T, — =a missing nucleotide. It will be seen that there is a substantial measure of agreement for these 16 nucleotides, of which 8 display 100% agreement and a ninth "X" agrees to the extent of being either A or G. These 9 nucleotides are underlined in the bottom row, showing the nucleotides of the common core region. Flanking the common core region are the residues of the tandem repeat sequences shown in lower case script. The beginning/end point of each repeat consensus is identified by the symbol ▼; in the case of λ33.4 and λ33.15, there are a non-integral number of repeats and the separate repeat beginning and end points are therefore shown by the different symbols ▽. It will be appreciated that the common core region was identifiable only by sophisticated analysis, since it often does not fall wholly within a single consensus sequence of the λ33-positive fragments and straddles two successive sequences of the myoglobin gene 33 bp repeat.

To illustrate the extent of compliance with the polynucleotides defined as being within the invention, the various determinants are given in Table 1 below:

TABLE 1

Figure 2:
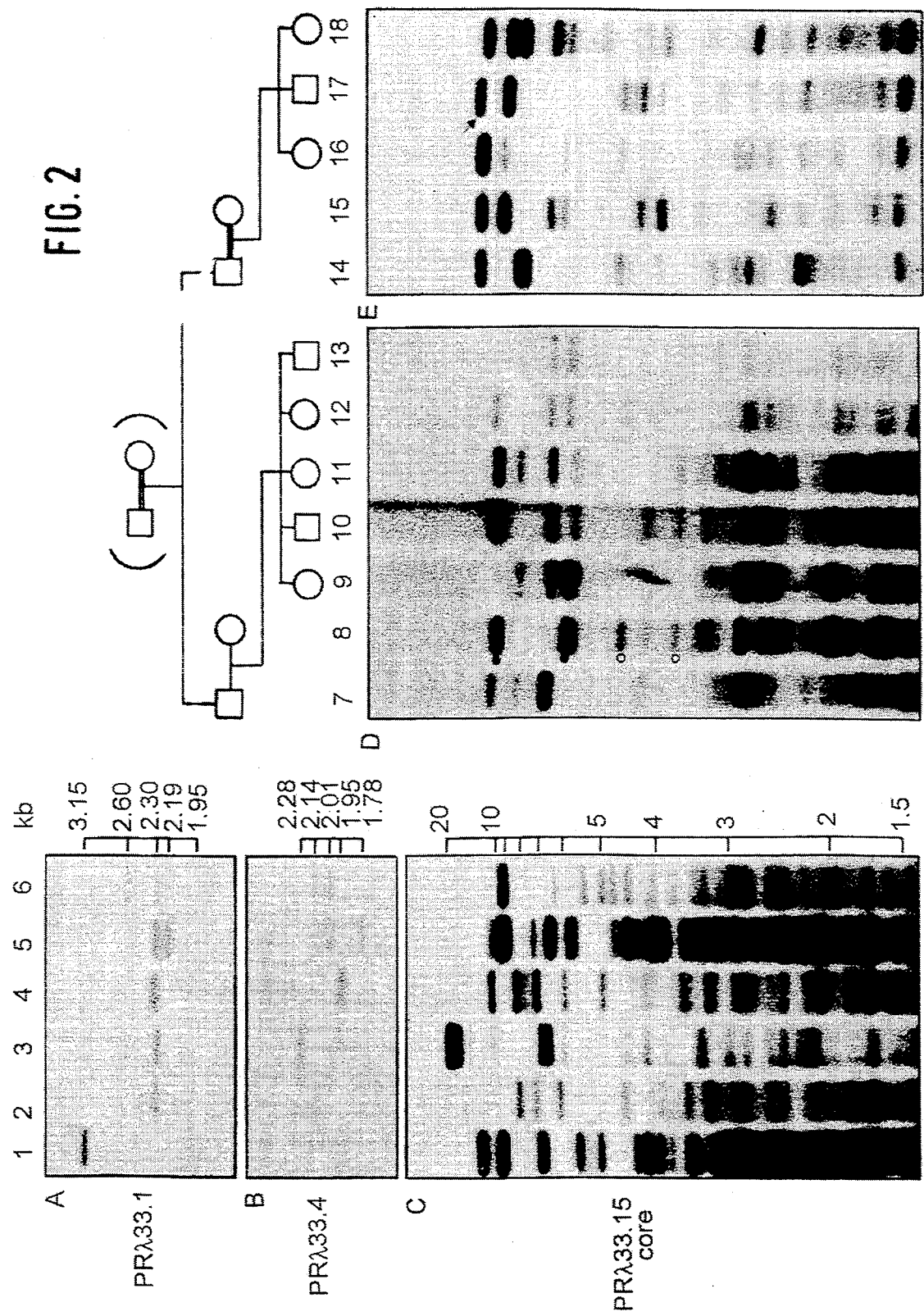
FIG. 2 is a photocopy of a photograph of autoradiographs of fragments of genomic DNA hybridising to various DNA probes, and also showing a pedigree of related individuals whose DNA was identified in two of the autoradiographs.

| Poly-nucleotides | Core Length | Formula No. | % Homology | Repeat Length | J & K | n | Within Invention |
|---|---|---|---|---|---|---|---|
| 33 bp myoglobin | 16 | 2 | 100 | 33 | 17 | 4 | X |
| 33.1 | 16 | 2 | 81 | 62 | 46 | 26 | X |
| 33.3 | 16 | 2 | 100 | 32 | 16 | 6 | X |
| 33.4 | 16 | 2 | 75 | 64 | 48 | 14 | X |
| 33.5 | 16 | 4 | 100 | 17 | 1 | 14 | ✓ |
| 33.6 | 11 | 5A,5B | 100 | 18 | 0 | 18 | ✓ |
| 33.10 | 15 | 2 | 88 | 41 | 26 | 5 | X |
| 33.11 | 16 | 2 | 94 | 33 | 17 | 3 | X |
| 33.15 | 16 | 3 | 100 | 16 | 0 | 29 | ✓ | underlined figures indicate impermissible lengths (4) Discovery that Polymorphic Human Genomic DNA Fragments can be Detected by Hybridization with Probes of Individual λ33-Positive Fragments Referring to FIG. 2, DNA was prepared from white blood cells taken from a random sample of British caucasians (1–6) and from selected members of a large British Asian pedigree (7–18). The pedigree is shown conventionally with the square denoting a male, the circle a female and marriage by a line between them. Two consanguinous marriages, between first first cousins, are denoted by a double line between the partners. 10 μg samples of DNA were digested with HinfI, electrophoresed through a 20 cm long 1% agarose gel, denatured in situ and transferred by blotting to a Sartorius nitrocellulose filter. Single-stranded $^{32}P$-labelled hybridization probes were prepared from M13 recombinants containing minisatellite (tandemly repeating) regions. The precise probes used are described later. The procedure was as follows. Approximately 0.4 μg M13 single-stranded DNA was annealed with 4 ng 17-mer sequencing primer, [M. L. Duckworth et al., Nucleic Acids Res. 9, 1691–1706 (1981)], in 10 μl 10 mM $MgCl_2$, 10 mM Tris-HCl (pH8.0) at 60° for 30 min. Primer extension was performed by adding 16 μl 80 μM dATP, 80 μM dGTP, 80 μM dTTP, 10 mM Tris-HCl (pH8.0), 0.1 mM EDTA plus 3 μl (30 μCi) $\alpha$-$^{32}P$-dCTP (3000 Ci mmole$^{-1}$) and 1 μl of 5 units μl$^{-1}$ Klenow fragment (Boehringer) and incubating at 37° for 15 min. Extension was completed by adding 2.5 μl 0.5 mM dCTP and chasing at 37° for a further 15 min. ("Chasing" means adding a dNTP mixture to complete the circle of ds DNA on the template of M13 ss DNA.) The DNA was cleaved at a suitable restriction endonuclease site either in the insert or in the M13 polylinker distal to the insert, denatured by adding 1/10 vol. 1.5M NaOH, 0.1M EDTA, and the $^{32}P$-labelled single-stranded DNA fragment extending from the primer was recovered by electrophoresis through a 1.5% low melting point agarose gel (Sea Plaque). The excised band (specific activity >10$^9$ cpm/μg DNA) was melted at 100° C. in the presence of 1 mg alkali-sheared carrier human placental DNA (sheared in 0.3M NaOH, 20 mM EDTA at 100° for 5 min then neutralised with HCl) and added directly to the hybridization chamber. The carrier DNA also served to suppress any subsequent hybridization to repetitive DNA sequences.

The precise hybridization probes used were: (A) 33.1, an approximate 2000 nt subcloned HaeIII fragment containing the minisatellite (26 repeats of a 62 nt sequence=1612 nt) plus approximately 350 nt flanking human DNA; (B) 33.4, a 695 nt non-minisatellite EcoRI fragment on the primer-proximal side of the minisatellite contained in a 2015 nt HinfI fragment; and (C, D, E) 33.15, a 592 nt subcloned fragment containing the λ33.15 minisatellite sequence (29 repeats of a 16 nt sequence, which is on average two nucleotides different from the common core region shown above) plus 128 nt flanking human DNA.

Hybridizations were performed as described by A. J. Jeffreys et al., Cell 21, 555–564 (1980), except that dextran sulphate was replaced by 6% (w/v) polyethylene glycol 6000 to reduce background labelling. Filters A and B were hybridized overnight in 0.5×SSC at 65° and washed in 0.2×SSC at 65°. Filters C–E were hybridized and washed in 1×SSC at 65°. Filters were autoradiographed for 1–3 days at −80° C. using a fast tungstate intensifying screen.

As shown in FIG. 2, the repeated core probe λ33.15, detected an extremely complex profile of hybridizing fragments in human DNA digested with HinfI. Only the largest (4–20 knt) HinfI fragments could be fully resolved and these showed extreme polymorphism to the extent that the hybridization profile provides an individual-specific DNA "fingerprint".

The pedigree analysis confirmed the extreme polymorphic variation, which is so great that all individuals, even within a single sibship of a first-cousin marriage (16–18 of FIG. 2), can be distinguished. The families in FIG. 2(D, E) shows that most of the large HinfI fragments were transmitted from each parent to only some of the offspring, thereby establishing that most of these fragments are present in the heterozygous state and that the heterozygosity for these large hypervariable fragments must be approaching 100%. Conversely, all fragments in offspring can be traced back to one or other parent (with only one exception), and therefore provide a set of stably inherited genetic markers. No band is specifically transmitted from father to son or father to daughter, see filter D, FIG. 2. This rules out Y and X linkage respectively, and implies that these minisatellite fragments are mainly autosomal in origin. While it is not yet known whence these DNA fragments originate in the set of autosomes, they are not derived from a single localised region of one autosome. Instead, pairs of parental fragments can be identified which segregate independently in the offspring, see filter D, FIG. 2. To be precise, a pair of bands AB in one parent (and absent from the other) cannot be allelic if there is at least one AB or—offspring; the presence of A- or -B recombinant progeny further establishes lack of tight linkage between A and B. Careful examination of the original autoradiograph of the family shown in FIG. 2D reveals by these criteria at least 10 resolvable bands in the mother, 8 of which are mutually non-allelic and not closely linked. Two other bands might each be an allele of one of the 8 unlinked fragments, in that only A- and -B progeny are observed in the limited number of offspring analysed, although such a small sample is insufficient to prove that such pairs of fragments are alleles of a single locus. The conclusion is that the core probe is capable of giving useful information simultaneously on at least several distinct unlinked hypervariable loci. This conclusion is examined in more details in Example 8.

By contrast, the other two probes (filters A and B, FIG. 2), not in accordance with the present invention, gave only one or two bands and were clearly incapable of detecting many different polymorphic regions simultaneously and therefore being of general diagnostic use.

EXAMPLE 2

The Use of Additional, Variant, (Core) in Probes to Detect New Sets of Hypervariable Regions in Human DNA Two further probes, derived from cloned λ33-positive fragments, λ33.5 and λ33.6, were prepared analogously to Example 1, step (4). The 33.5 probe consisted of a 308 nt DNA fragment cloned in M13mp8 and comprised 14 repeats of the consensus sequence shown above, which is an effect a 17 nt long variant of the common core sequence, together with 70 nt flanking human DNA. The 33.6 probe included 18 repeats of a 37 nt sequence which in turn, comprises 3 repeats of an approximate 12 nt shortened sequence derived from the common core region plus an additional TC at the 5'-end thereof. The 18×37 nt repeat blocks were flanked by 95 nt human DNA. The structure of the 37 nt sequence can be represented as:

| TGG AGG | AGG | GGC |
| TGG AGG | A—G | GGC (or TGG AGG AGG G—C) |
| TCCGG AGG | AGG | GGC |

This probe was likewise cloned in M13mp8.

In later description an 11 nt consensus sequence AGGGCTGGAGG is given for this probe.

Both probes were labelled with $^{32}P$ and hybridised analogously to Example 1, step (4) to human DNA from a panel of 14 unrelated caucasians. Both probes detected a complex set of hybridising fragments, many of which showed extreme polymorphic variation. Several of the fragments detected by 33.5 were new and had not previously been detected by the 33.15 core probe. The 33.6 probe detected an almost entirely new set of minisatellites, and the correct inheritance of these has been verified by pedigree analysis. (See Example 8).

The following examples further illustrate and exemplify the invention.

The digestion of the sample DNA is preferably carried out using a restriction endonuclease which recognises 4 base pairs of nucleotides. It has been found that the DNA fingerprint pattern for the longest hypervariable fragments is largely independent of the 4 bp recognition restriction endonuclease used. This strongly suggests that these large fragments are not derived from longer minisatellites, but that each contains a complete long homogeneous minisatellite, devoid of restriction endonuclease cleavage sites and flanked by human DNA containing the normal high density of 4 bp cleavage sites. This is in agreement with results presented in the earlier examples and in Example 8 which show that most of these large minisatellite fragments are unlinked and segregate independently in pedigree.

In a preferred embodiment a sample of DNA is "doubly fingerprinted" by using two different probes, in separate hybridisations producing two different fingerprints, for example probes from fragments lambda 33.15 and 33.6. By this means the already low probability that two unrelated individuals will have the same fingerprint is decreased further. For instance, Example 4 indicates a probability as low as $10^{-19}$ even when, as is preferred, incompletely-resolved hybridising DNA fragments of length less than 4 kb are ignored.

The invention includes a method for paternity testing. Approximately half of the polymorphic minisatellite fragments in an offspring are derived from the father, and these paternal fragments can be identified by comparison of the mother's and offspring's DNA fingerprints. All of these paternal fragments will ordinarily be present in the father's DNA. It is estimated that using a probe 33.15 and DNA fragments of length at least 4 kb, the probability that the putative father will by chance possess all 6 paternal-specific DNA fragments typically identified in the offspring is of the order of $10^{-5}$ and that use of both probes 33.6 and 33.15 reduces it to the order of $10^{-8}$. Naturally, the precise probabilities will depend on the exact resolution and complexity of the DNA patterns obtained, and will be improved if additional paternal fragments less than 4 kb long are analysed or if a third probe is used.

Sufficient DNA (0.5–5 micrograms) can be isolated rapidly from a single drop of human blood for DNA fingerprinting. Thus, DNA fingerprints have been produced from a randomised panel of individuals including two people whose DNA had been previously fingerprinted, plus two sisters. The two previously characterised individuals could be readily and unambiguously identified on the basis of DNA fingerprint comparisons, as could the two sisters who shared a substantial number of minisatellite fragments in common.

The DNA can be taken from a variety of cells from a given individual, all giving the same fingerprint. Thus the DNA fingerprints for sperm and blood DNA are indistinguishable, as are the patterns of monozygous twins. Furthermore, the patterns appear to be stably maintained in cultured cells, as shown by comparing the DNA fingerprints of blood DNA with DNA isolated from Epstein-Barr virus transformed lyphoblastoid cell lines derived from the same individual.

Non-human animals to which the invention is applicable include most mammals, birds, amphibians and fish. Examples are chickens, hamsters, rabbits, mice, sparrows, kestrels, frogs, newts and fish. In the case of chickens, a very complex smeared portion of hybridising DNA fragments was produced. Digestion with HaeIII eliminated the smear, revealing a "clean" fingerprint. It is therfore likely that chicken DNA also contains a long core-containing satellite whose repeat units contain one or more HaeIII cleavage sites; cleavage with HaeIII therefore reduces this satellite to very small DNA fragments which migrate off the bottom of the gel during DNA electrophoresis. It is likely occasionally that other animals will produce smeared bands and that these will be resolvable if the DNA is digested with appropriate enzymes which cleave the longer fragments.

In the following additional Examples, temperatures are in °C.

EXAMPLE 3

DNA was isolated from fresh human placentae, as described by A. J. Jeffreys, Cell 1–10 (1979). Three individual placentae were used, labelled 1–3. 8 microgram samples of DNA were digested with HinfI and/or Sau3A, in the presence of 4 mM spermidine trichloride to aid complete digestion, recovered after phenol extraction by ethanol precipitation, and electrophoresed through a 20 cm long 0.6% agarose gel at 30 V for about 24 hours, until all DNA fragments less than 1.5 kb long had electrophoresed off the gel. DNA was then transferred by blotting to a Sartorius nitrocellulose filter. High specific activity (greater than 109 cpm $^{32}$P/microgram DNA) single stranded M13 DNA probes were prepared as described in Example 1, step 4). The precise probes used were: (a) 33.5 probe consisting of a 220 nt HaeIII DNA fragment containing most of the lambda 33.5 minisatellite (17 nt × 14 repeats) plus about 60 nt flanking human DNA, subcloned into the Sinai site of M13mp8; (b) 33.6 probe consisting of a 720 nt HaeIII fragment consisting of the minisatellite plus about 50 nt flanking human DNA subcloned into the Sinai site of M13mp8; and (c) the same 33.15 probe as in Example 1, step (4), this being a 592 nt Psti - AhaIII fragment containing the minisatellite plus 128 nt flanking human DNA subcloned into M13mp19 DNA digested with PstI plus Sinai. Southern blot hybridisation and washing were performed in 1×SSC at 65° as described previously for filters C–E in Example 1, step (4). Filters were autoradiographed at room temperature without an intensifier screen for four days.

Figure 3:
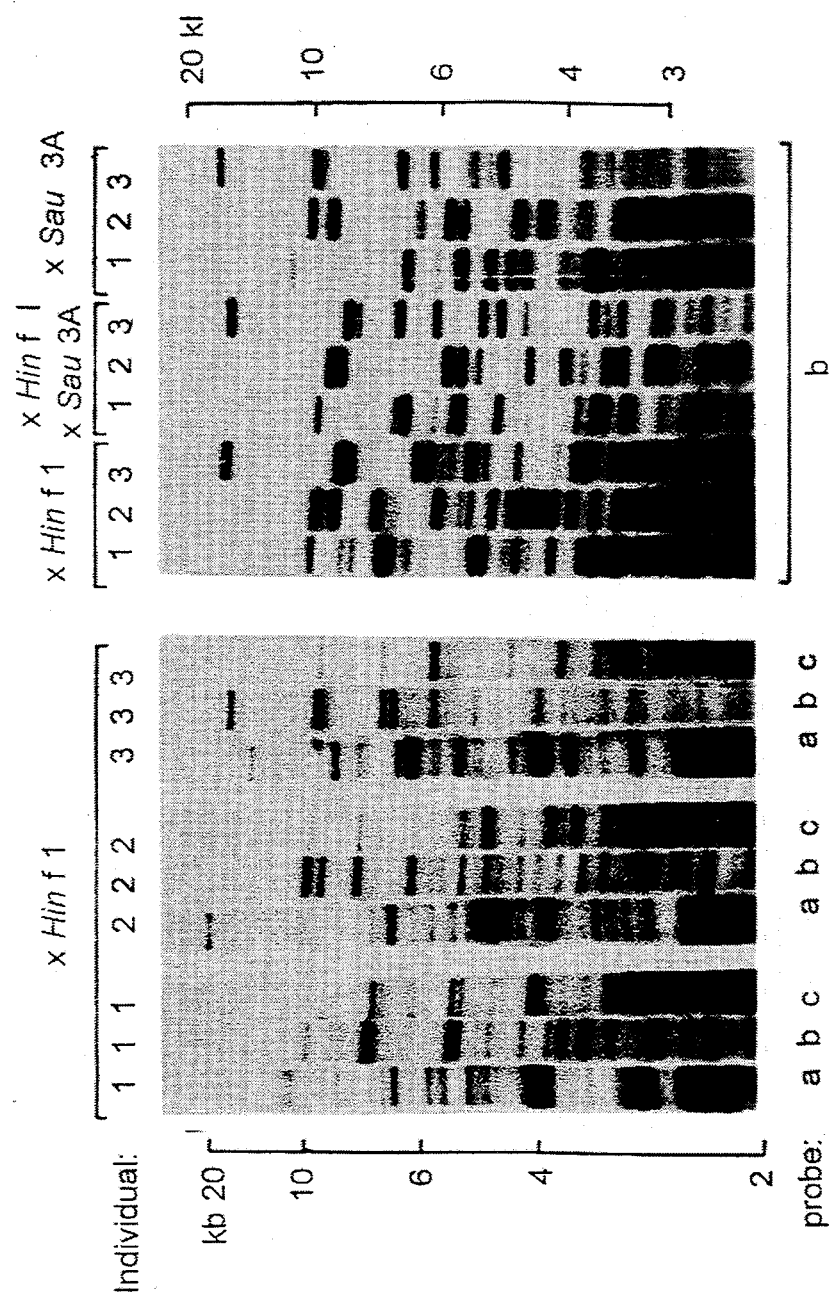
FIG. 3 shows autoradiographs of DNA samples from 3 unrelated human individuals probed with three different probes of the invention.
Figure 4:
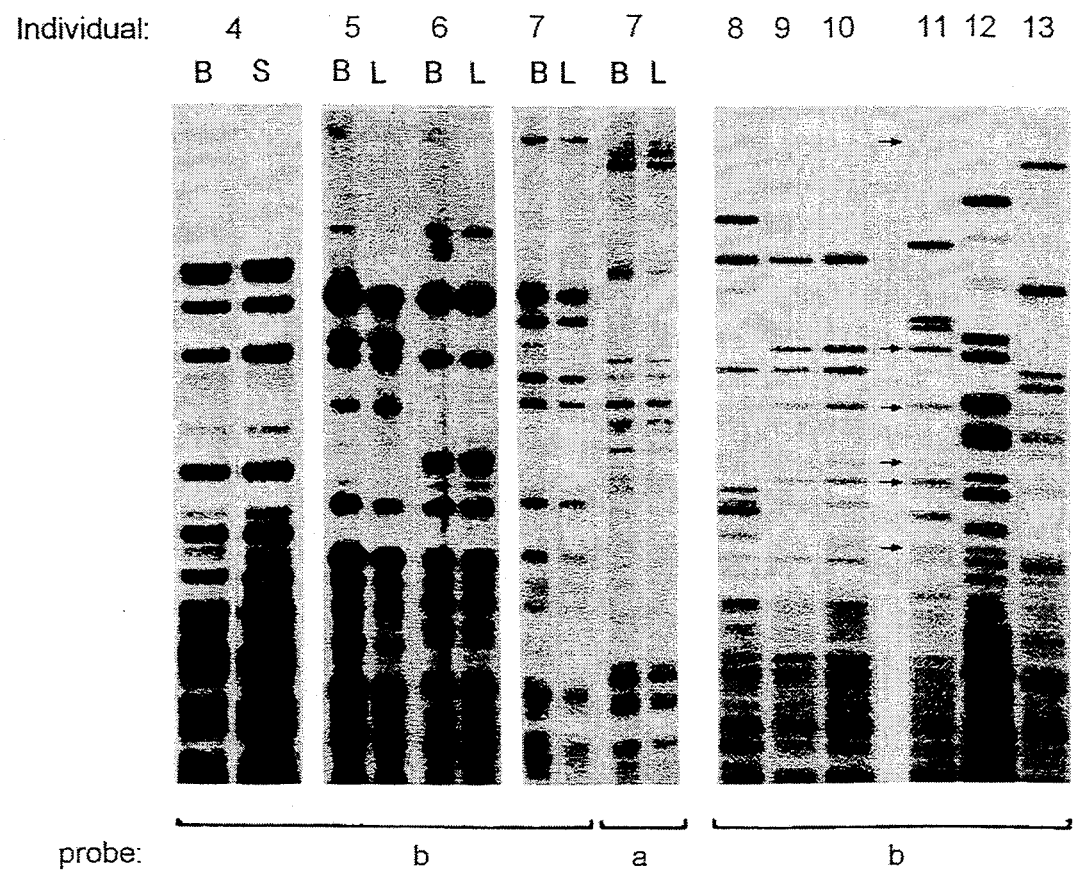
FIG. 4 shows an autoradiograph of DNA samples from 9 human individuals, some of whom are related and two of whom are identical twins, probed with a probe of the invention.

Each probe produced a different fragment pattern the complexity of which is largely independent of the tetranucleotide restriction endonuclease used. FIG. 3 shows the pattern obtained. Resolution of polymorphic fragments less than 4 kb long is improved in double digests with HinfI plus Sau3A, due to the elimination of background hybridisation caused presumably by relatively diverged and invariant HinfI minisatellite fragments which have accumulated Sau3A cleavage sites within one or more repeat units. In double digests, the number of resolvable polymorphic fragments detected by probe 33.15 can be increased from about 15 to about 23 per individual, at the expense of losing about 20% of long single digest minisatellite fragments which presumably contain a Sau3A cleavage site in most or all repeat units.

EXAMPLE 4

8 microgram samples of human blood DNA taken from a random sample of 20 unrelated British caucasians were digested with HinfI and Southern blot hybridised with the minisatellite probe 33.6 or 33.15 as described in Example 3. Each DNA fingerprint (individual A) was compared with the pattern in the adjacent gel track (individual B), and the number of bands in A which were clearly absent from B, plus those which had a co-migrating counterpart of roughly similar autoradiographic intensity in B, were scored. The results, shorn in the table below, are averages for all pairwise comparisons. A small proportion (about 6%) of additional weakly hybridising fragments in A were matched by strongly hybridising fragments in B, and since in such cases it was not possible to decide whether the band in A was also present in B, such fragments were ignored. If co-migrating bands in A and B are always identical alleles of the same minisatellite locus, then the mean probability x that an allele in A is also present in B is related to the mean allele frequency (homozygosity) q by $x=2q-q^2$, whence $q=1-(1-x)^{\frac{1}{2}}$. In practice, an (unknown) proportion of co-migrating bands in A and B will be derived by chance from different minisatellite loci, and thus the estimates of mean allele frequency and homozygosity are maximal, and depend upon the electrophoretic resolution of minisatellite fragments.

The probabilities shown in Table 1 relate to the individual size fragments of DNA shown. To obtain an overall probability relating to the most legible part of the fingerprint, i.e. all DNA above 4 kb in size, the three figures have to be combined. Thus, for example, the mean probability that all fragments detected by the probe 33.15 in individual A are also present in B is $0.08^{2.9} \times 0.20^{5.1} \times 0.27^{6.7} = 3 \times 10^{-11}$. The probability that oil fragments detected by both probes 33.15 and 33.6 in A are also present in B is $5 \times 10^{-19}$.

TABLE 2

Similarities of DNA fingerprints between random pairs of individuals

| Probe | DNA fragment size, kb | No. of fragments per individual ± S.D. | Probability x that fragment in A is present in B | Maximum mean allelic frequency (homozygosity) |
|---|---|---|---|---|
| 33.6 | 10–20 | 2.8 ± 1.0 | 0.11 | 0.06 |
|  | 6–10 | 5.1 ± 1.3 | 0.18 | 0.09 |
|  | 4–6 | 5.9 ± 1.6 | 0.28 | 0.15 |
| 33.15 | 10–20 | 2.9 ± 1.0 | 0.08 | 0.04 |
|  | 6–10 | 5.1 ± 1.1 | 0.20 | 0.11 |
|  | 4–6 | 6.7 ± 1.2 | 0.27 | 0.15 |

EXAMPLE 5

This example illustrates the somatic stability of DNA fingerprints and their use in paternity testing.

Lymphoblastoid cell lines transformed by EB virus and stored in liquid nitrogen were re-established in liquid culture after 2 years. These cultured lymphocytes were washed twice in normal saline; DNA from the lymphocyte pellet and from white blood cells was prepared as described by A. J. Jeffreys, Cell 18, 1–10 (1979). Sperm DNA was similarly prepared, except that sperm collected from semen were treated with 1M 2-mercaptoethanol for 5 minutes at room temperature, prior to lysis with SDS. DNA fingerprints were prepared as described in Example 3, using 5 microgram samples of DNA digested with HinfI and hybridised with probe 33.6 (a) or 33.15 (b).

EXAMPLE 6

This example illustrates use of a probe of the invention to detect highly polymorphic regions in the DNA of various vertebrates.

Figure 5:
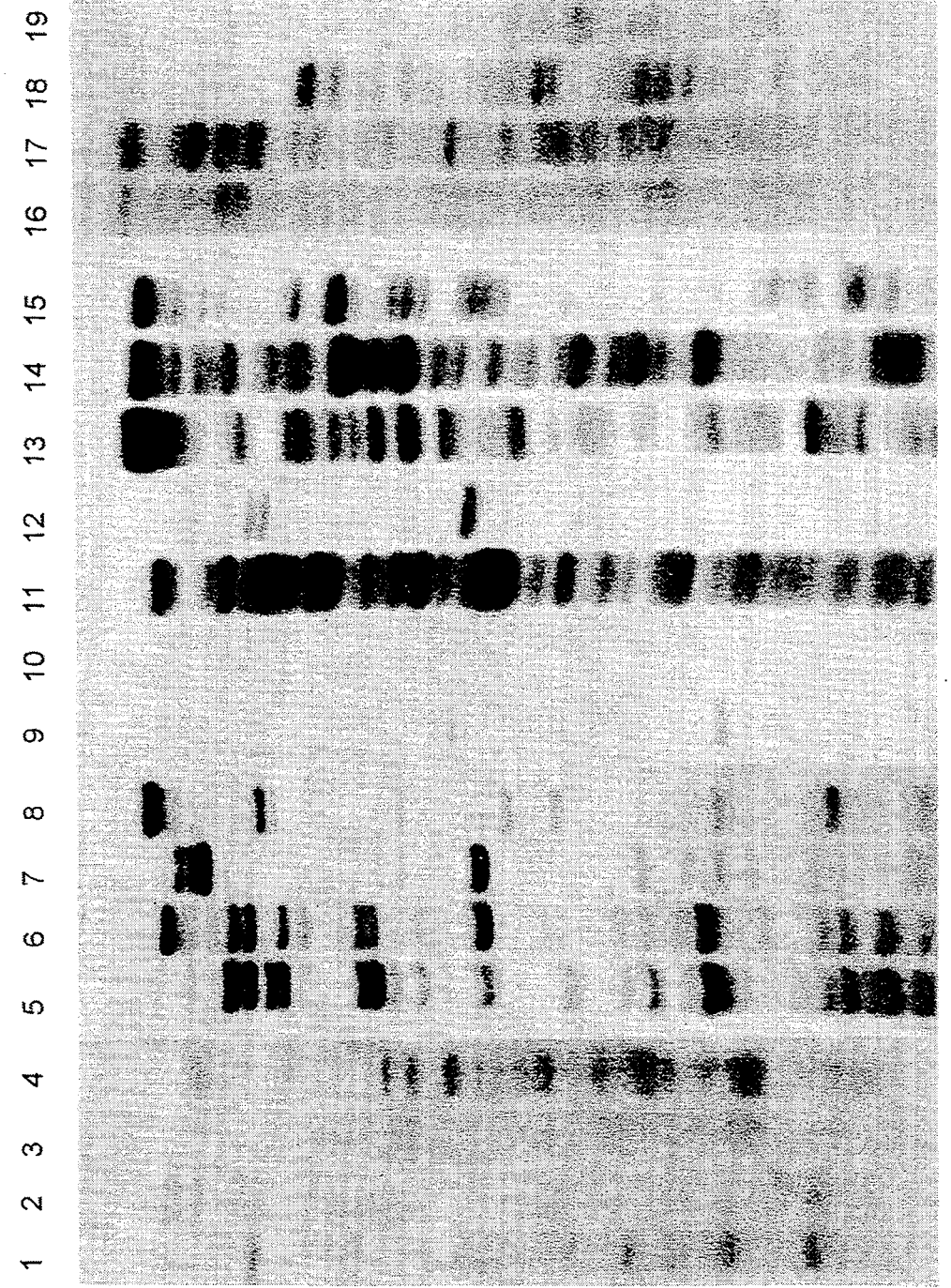
FIG. 5 shows autoradiographs of DNA samples from 2 humans and 17 non-human animals probed with a probe of the invention.

DNA samples were prepared from blood taken from chickens, sparrows and kestrels, from rabbit and mouse liver, from human placentae, and from the degutted carcasses of frogs and fish. 8 ug samples of DNA were digested with HinfI, except for chicken DNA which was digested with HaeIII. The restriction digests were electrophoresed through a 0.6% agarose gel, denatured, transferred to a Sartorius nitrocellulose filter and hybridised as described previously with the human minisatellite probe 33.15. The hybridisation stringency was at 65° in 1×SSC. The results are shown in FIG. 5, with the following samples:

| 1, 2 | unrelated human placentae DNA. |
|---|---|
| 3 | rabbit DNA, from an $F_1$ hybrid of Alaska and Vienna White strains. |
| 4 | rabbit DNA, from Alaska strain. |
| 5, 6 | mouse (Mus musculus) DNA: from two Greek mice caught in the wild. |
| 7 | mouse (Mus musculus) DNA: from inbred strain DBA-2. |
| 8 | mouse (Mus musculus) DNA: from inbred strain C57/BL10. |
| 9, 10 | chicken DNA: NB the DNA was digested with HaeIII. |
| 11, 12 | sparrow DNA. |
| 13, 14, 15 | kestrel DNA. |
| 16, 17 | frog (Xenopus tropicalis) DNA. |
| 18, 19 | minnow DNA. |

As can be seen, successful variable DNA fingerprints were obtained from nearly all vertebrates tested, and are apparently as informative as the human DNA fingerprints.

The chicken DNA cleaved with HinfI also produced a very complex, though less intense, smear of hybridising DNA (not shown). However, digestion with HaeIII eliminated this smear and revealed a clean polymorphic fingerprint pattern.

The two inbred mouse strains have simpler fingerprints than the wild-caught mice. This is to be expected since most hypervariable minisatellite loci will be heterozygous in the wild but homozygous on inbreeding, halving the number of hybridising DNA fragments in inbred strains.

The following examples illustrate further the application of particular probes described above.

EXAMPLE 7

This describes the use of DNA fingerprint analysis in an immigration case, the solution of which would have been very difficult, if not impossible, by conventional genetic methods.

The case concerned a Ghanaian boy born in the U.K. who emigrated to Ghana to be reunited with his father and subsequently returned alone to the U.K. to rejoin his mother, brother and two sisters. However, there was evidence to suggest that a substitution had occurred, either for an unrelated boy, or for a son of one of the mother's sisters all of whom live in Ghana. As a result, the returning boy was not granted residence in the U.K. At the request of the family's solicitor, an analysis was undertaken to determine the maternity of the boy. To complicate matters, neither the father nor any of the the mother's sisters were available for analysis. Furthermore, while the mother was certain that the boy was her son, she was not sure about his paternity. DNA fingerprints from blood DNA samples taken from available members of the family (the mother M, brother B, sisters S1 and S2 and the boy X in dispute) were therefore prepared by Southern blot hybridisation to two minisatellite probes 33.6 and 33.15 described above, each of which detects a different set of hypervariable minisatellites in human DNA.

Figure 6:
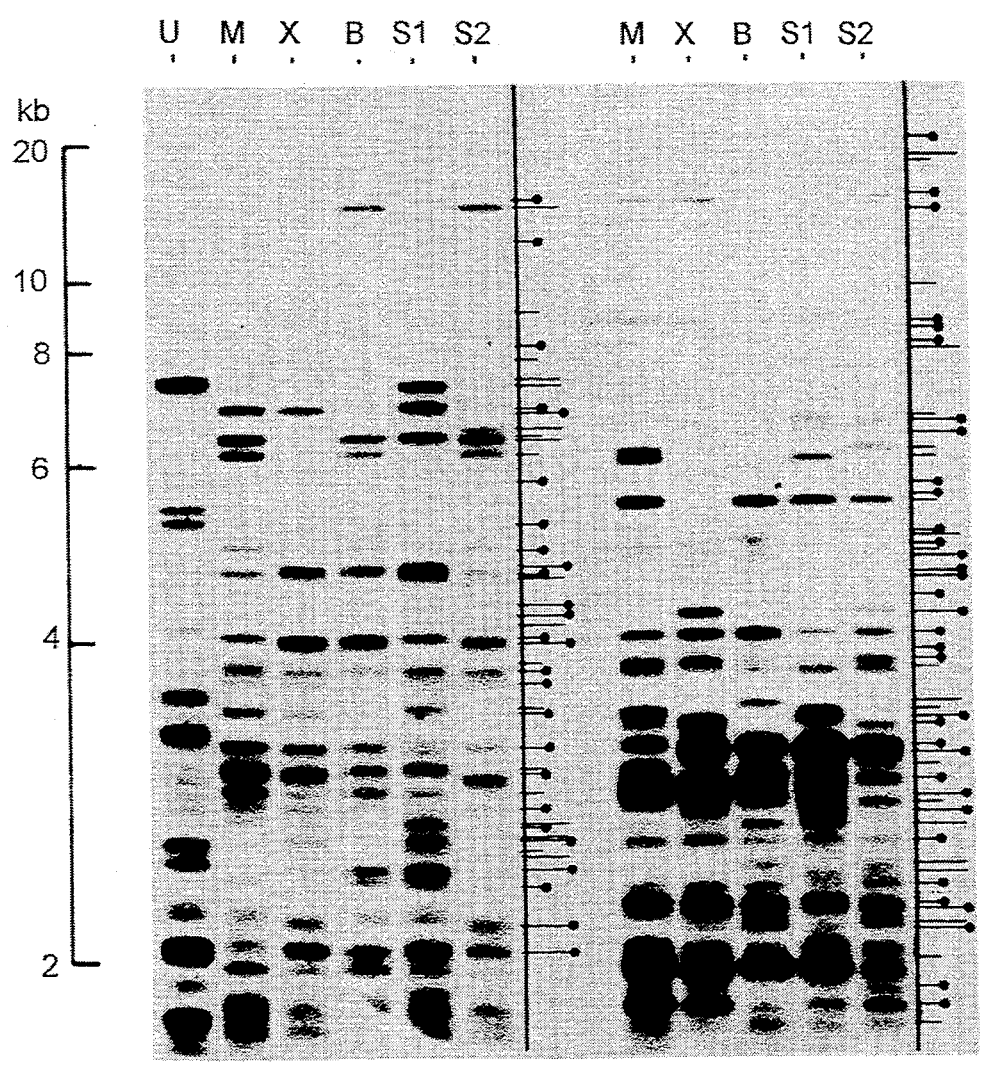
FIG. 6 shows a series of autoradiographs of DNA samples from members of a Ghanaian family involved in an immigration dispute, probed in accordance with the invention.

8 μg samples of blood DNA from the mother (M), the boy in dispute (X), his brother (B), sisters (S1, S2) and an unrelated individual (U) were digested with HinfI, electrophoresed through a 0.7% agarose gel and Southern blot hybridised to the probes. The autoradiographs are shown in FIG. 6. Fragments present in the mother's (M) DNA fingerprints are indicated by a short horizontal line; paternal fragments absent from M but present in at least one of the undisputed sibs (B, S1, S2) are marked with a long line. "Maternal" and paternal fragments transmitted to X are shown by a dot. The DNA fingerprints of X contain no additional resolved fragments. All fragments were scored from the original autoradiographs taken at various exposures; partially-resolved fainter bands, particularly towards the bottom of the gel, which could not be reliably scored were ignored.

The first step was to establish the paternity of X from the patterns of hypervariable fragments. Although the father was unavailable, most of his DNA fingerprint could be reconstructed from paternal-specific DNA fragments present in at least one of the three undisputed sibs (B, S1, S2) but absent from M. Of the 39 paternal fragments so identified, approximately half were present in the DNA fingerprints of X. Since DNA fragments are seldom shared between the DNA fingerprints of unrelated individuals (see individual U in FIG. 6), this very strongly suggests that X has the same father as B, S1 and S2. After subtracting these paternal-specific DNA fragments, there remained 40 fragments in X, all of which were present in M. This in turn provides strong evidence that M is the mother of X, and therefore that X, B, S1 and S2 are true sibs.

It has been shown above that the mean probability that a fragment in the DNA fingerprint of one person is present in a second individual selected at random is approximately 0.2 for North Europeans. The corresponding estimate for the father and M is 0.26, establishing that DNA fingerprint variability in these Ghanaians is not significantly different from that of North Europeans. In the following probability estimates, the highly conservative assumption is made that all bands are shared with a uniform probability of 0.26 (quantitation follows).

The first question is whether X is related to this family. The DNA fingerprints of X contain 61 scorable fragments, all of which are present in M and/or the father. If X is unrelated, then the probability that each of his bands is present in these parents is $1-(1-0.26)^2=0.45$; the probability that M and/or the father by chance possess all 61 of X's bands is therefore $0.45^{61}=7\times 10^{-22}$. X is clearly related to this family.

The next problem is whether an unrelated woman, and not M, could be the mother of X. The DNA fingerprints of X contain 40 "maternal" fragments, of which we estimate that $\sim 25$ were inherited specifically from the mother; remaining fragments are shared between the mother and father and cannot therefore be used to adduce evidence for M's maternity. All 25 maternal-specific fragments in X are present in M. The chance that M is unrelated to X but happens to share all 25 fragments is therefore $0.26^{25}=2\times 10^{-15}$. Thus X and M must be related.

The final and most difficult problem is whether M's sister, who was not available for analysis, could be the mother of X (the father of course would have to be M's husband). If bands are shared between random people with a mean probability of 0.26, then the corresponding chance that a fragment in one individual is also present in a sib is 0.62. The odds that M is the sister of X's true mother and by chance contains all 25 of X's maternal-specific bands are therefore $0.62^{25}=3\times 10^{-6}$. We therefore conclude that, beyond any reasonable doubt, M must be the true mother of X. This evidence was provided to the immigration authorities, who dropped the case against X and granted him residence in the U.K., allowing him to remain with his family.

This difficult case demonstrates how DNA fingerprints can give unequivocal positive evidence of relationship, even in some cases where critical family members are missing. The present case was simplified by the fact that X had the same father as his sibs, and that this father did not transmit any bands solely to X (on average, 1/16 of paternal bands would be so transmitted). Such X-unique fragments, while apparently weakening the evidence for the relationship between X and M, would not in practice necessarily invalidate the analysis. X would be unlikely to have more than 5 such paternal fragments, in addition to the 25 maternal-specific fragments. The odds of at least 25 out of 30 specified bands matching by chance between X and M if they are unrelated, or if M is X's aunt, is $8\times 10^{-11}$ and $9\times 10^{-3}$ respectively. This analysis is therefore robust and would give clear evidence for or against claimed relationships in most such cases. Usually, of course, all relevant members of a family will be available, in for example paternity disputes or with families having difficulties in reuniting by immigration; DNA fingerprints will almost always be capable of resolving such problems.

Quantitation of DNA Fingerprints

61 DNA fragments were scored in M, compared with 39 fragments inherited specifically from the father. $\frac{1}{8}$ of the father's heterozygous DNA fragments will not be transmitted to B, S1 or S2 and thus the corrected estimate for the number of paternal-specific fragments is $39\times 8/7=45$. Since the total number of fragments in the DNA fingerprints of M and the father should be approximately equal, then the number of fragments in M which are shared by the father is $\sim(61-45)=16$. The mean probability of band sharing (x) in M and the father is therefore $16/61=0.26$, consistent with previous estimates derived from screening a B random sample of North Europeans (x=0.2, ref. 2).

Approximately half of the 45 paternal bands were transmitted to B, S1 and S2 (18, 24 and 18 respectively) as expected for heterozygous bands. Of the 61 bands in M, more than half were inherited by B, S1 and S2 (32, 38 and 39 respectively, mean=36.3), as expected since some of M's bands will be shared by the father and will therefore be transmitted to most or all children. If M's DNA fingerprints contain n shared bands transmitted to all children plus (61−n) heterozygous bands transmitted to half the children, then $n+0.5(61-n)=36.3$, whence $n=12$, consistent with the estimate of 16 bands common to M and the father (see above).

The DNA fingerprints of X are comprised of 21 paternal-specific fragments plus 40 bands shared with M. The proportion of the latter bands which are maternal-specific and not shared by the father can be estimated in two ways. First, the number of maternal-specific bands should be roughly equal to the number specific to the father, that is $45/2=22.5$. Second, n ($\sim 12$) of the 40 maternal bands in X will be shared maternal/paternal bands (see above), which leaves 28 maternal-specific bands in X. The number of fragments that X has acquired specifically from his mother is therefore $\sim 25$.

Probabilities of band sharing: The mean probability that a fragment in one individual is matched by a band of similar electrophoretic mobility and autoradiographic intensity in a second random person is defined as x (x=0.2−0.26, see above). Larger minisatellite fragments are less frequently shared, probably due to lower allele frequencies and better electrophoretic resolution, and thus the fragment sharing probability x is heterogeneous. Since almost all fragments are inherited independently, the maximum probability that all n fragments in an individual are present in a second random individual is therefore $x^n$; any heterogeneity in x will reduce this probability. Band sharing between sibs: If shared bands always represent identical alleles of the same hypervariable locus, then x is related to the mean allele frequency q by $x=2q-q^2$, whence it can be shown that the probability of given band in an individual is also present in his or her sib is $(4+5q-6q^2+q^3)/4(2-q)$.

For, X=0.26,q is 0.14 and the expected proportion of bands present in a first sib which are shared by a record is 0.62. This probability is B slightly reduced if it is assumed instead that bands shared by random people are never identical alleles, that is, that many minisatellites have alleles of the same size.

APPLICATION OF DNA FINGERPRINTS TO ANALYSIS OF GENETIC DISEASE

To determine the feasibility of using DNA fingerprints for linkage analysis in man, in particular for searching for hypervariable DNA fragments which cosegregate with disease loci in large pedigrees, the DNA fingerprints of two large families were investigated, one segregating for neurofibromatosis and the other for hereditary persistance of foetal haemoglobin apparently determined by an autosomal dominant gene not linked to the β-globin gene cluster.

EXAMPLE 8

Figure 7A:
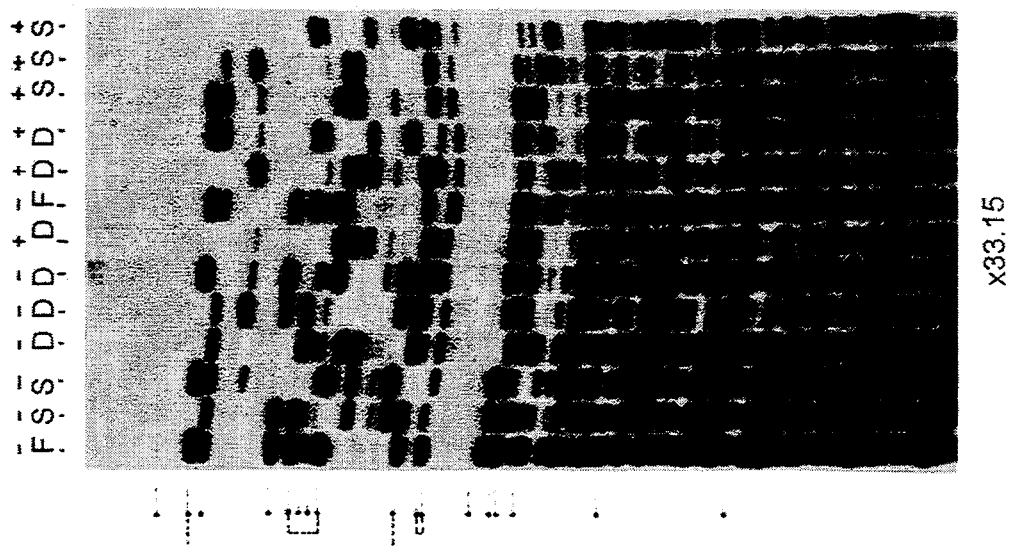
FIGS. 7 and 7A show autoradiographs of DNA samples of a sibship affected by neurofibromatosis.
Figure 7B:
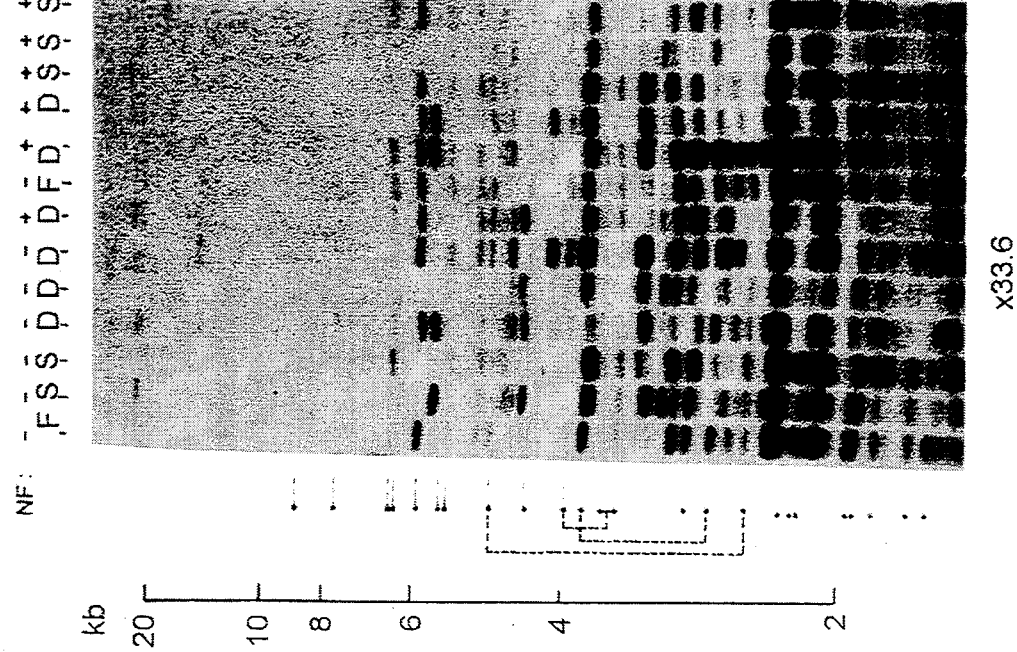

Segregation of Hypervariable Minisatellite Fragments in the DNA Fingerprints of a Sibship Affected by Neurofibromatosis Blood DNA samples digested with HinfI were electrophoresed on a 35 cm long 0.7% agarose gel and Southern blot hybridised to minisatellite probes 33.6 and 33.15. DNA fingerprints are shown in FIG. 7 for the unaffected father (F), 5 sons (S) and 6 daughters (D); the affected mother was not B available for study. Offspring affected by multiple neurofibromata are indicated (+); the remaining offspring show no sign of neurofibromatosis. Resolved paternal (●) and maternal (○) heterozygous DNA fragments are indicated, and their segregation into offspring was scored directly from original autoradiographs taken at short, medium and long exposures. Only those DNA fragments were scored whose positions and relative intensities in each offspring matched those in the parent. Linked pairs AB of DNA fragments which segregate AB or—into offspring are joined by a continuous line; alleles which segregate A- and -B are joined by dotted lines. One maternal fragment which shows evidence of linkage in coupling to neurofibromatosis is marked with an asterisk; all six affected offspring have inherited this fragment, and four out of five unaffected children do not have this band, giving a concordance of 10/11 between the inheritance of this band and neurofibromatosis.

MATERIALS AND METHODS

DNA Isolation

Fresh blood was diluted with an equal volume of 1×SSC (SSC, saline sodium citrate, 0.15M NaCl, 15 mM trisodium citrate, pH7.0), layered onto Histopaque-1077 (Sigma) and nucleated cells collected by centrifugation. Alternatively, frozen blood was thawed in 2 vol 1×SSC and nucleated cells plus nuclei pelleted by centrifugation at 10,000 g for 15 min. High molecular weight DNA was prepared as described in Jeffreys, A. J. (1979). Cell 18, 1–10.

Southern Blot Analysis

5 μg samples of human DNA were digested with 20 units of HinfI in the presence of 4 mM spermidine trichloride at 37° for 2 hr, and recovered by phenol extraction and ethanol precipitation. Restriction digests were dissolved in 16 μl H$_2$O plus 4 μl gel loading mix (12.5% ficoll 400, 0.2% bromophenol blue, 0.2M Tris acetate, 0.1M Na acetate, 1 mM EDTA, pH8.3) and 2 μl 5 mg/ml ethidium bromide, and loaded onto a horizontal agarose gel (0.7% Sigma Type I agarose in 40 mM Tris acetate, 20 mM Na acetate, 0.2 mM EDTA, 0.5 μg/ml ethidium bromide (pH8.3); gels 0.7 cm thick by 20 cm or 35 cm long). After equilibration for 10 min, gels were electrophoresed at 2 V/cm for 24–48 hr, until all DNA fragments less than 1.5 kb long had electrophoresed off the gel. DNA was transferred by blotting onto a nitrocellulose filter (Sartorius, 0.45 μm pore size). $^{32}$P-labelled single-stranded probe DNA was prepared from the human minisatellite M13 recombinants 33.6 and 33.15, hybridised to Southern blots in 1×SSC at 65° and autoradiographed as described in the main application.

Data Analysis

Storage of segregation data and analysis of linkage were performed on a BBC model B microcomputer.

Table 2 gives a summary of minisatellite markers in the neurofibromatosis family.

TABLE 3

| probe: | Father | | Mother | |
|---|---|---|---|---|
| | 33.6 | 33.15 | 33.6 | 33.15 |
| no. fragments scored (n) | 24 | 17 | 16 | 16 |
| no. allelic pairs (a) | 3 | 3 | 2 | 4 |
| no. linked pairs (b) | 1 | 0 | 1 | 0 |
| no. different loci scored (c) | 20 | 14 | 13 | 12 |
| estimated total no. loci (N) | 43 | 23 | 27 | 16 |

The number of different loci (c) scored is given by n-a-b. The entire DNA fingerprint, including unresolved and therefore unscored fragments, is derived from N heterozygous loci (2N fragments). Assuming that the (n-b) distinct fragments scored are a random sample of the 2N bands in a DNA fingerprint, then the estimated total number of hypervariable loci N detected by a given $$N = \frac{1}{2}\left[\frac{(n-b)(n-b-1)}{2a} + 1\right]$$

TABLE 4

Segregation of hypervariable fragments in the neurofibromatosis family.

| transmission of: to: no. children (r) | Father | | | | | | | Mother | | | | | | |
|---|---|---|---|---|---|---|---|---|---|---|---|---|---|---|
| | single fragment | | pair (AB or --) | | | | | single fragment | | pair (AB or --) | | | | |
| | | | | | exp | | | | | | | exp | | |
| | obs. | exp. | obs. | U | 30 | 20 | 10 | obs. | exp. | obs. | U | 30 | 20 | 10 |
| 0 | 0 | 0.02 | (0) | 0 | 1 | 2 | 9 | (0) | 0.02 | (0) | 0 | 0 | 1 | 6 |
| 1 | 0 | 0.2 | 4 | 3 | 5 | 8 | 19 | 1 | 0.2 | 0 | 2 | 3 | 5 | 13 |
| 2 | 1 | 1.1 | 16 | 15 | 18 | 22 | 31 | 2 | 0.9 | 5 | 8 | 10 | 13 | 19 |
| 3 | 1 | 3.3 | 48 | 45 | 47 | 49 | 51 | 3 | 2.6 | 26 | 24 | 26 | 27 | 28 |
| 4 | 5 | 6.7 | 90 | 90 | 89 | 85 | 76 | 5 | 5.2 | 48 | 48 | 47 | 45 | 38 |
| 5 | 8 | 9.2 | 113 | 127 | 121 | 114 | 95 | 6 | 7.2 | 61 | 68 | 64 | 59 | 45 |
| 6 | 12 | 9.2 | 120 | 127 | 121 | 114 | 95 | 5 | 7.2 | 77 | 68 | 64 | 59 | 45 |
| 7 | 10 | 6.7 | 89 | 90 | 89 | 85 | 76 | 6 | 5.2 | 52 | 48 | 47 | 45 | 38 |
| 8 | 4 | 3.3 | 58 | 45 | 47 | 49 | 51 | 4 | 2.6 | 23 | 24 | 26 | 27 | 28 |
| 9 | 0 | 1.1 | 19 | 15 | 18 | 22 | 31 | 0 | 0.9 | 7 | 8 | 10 | 13 | 19 |
| 10 | 0 | 0.2 | 4 | 3 | 5 | 8 | 19 | 0 | 0.2 | 1 | 2 | 3 | 5 | 13 |
| 11 | (0) | 0.02 | (0) | 0 | 1 | 2 | 9 | (0) | 0.02 | (0) | 0 | 0 | 1 | 6 |

TABLE 4-continued

Segregation of hypervariable fragments in the neurofibromatosis family.

| transmission of: | Father | | | | | | Mother | | | | | |
|---|---|---|---|---|---|---|---|---|---|---|---|---|
| | single fragment | | pair (AB or --) | | | | single fragment | | pair (AB or --) | | | |
| | | | | exp | | | | | | exp | | |
| no. children (r) | obs. | exp. | obs. | U | 30 | 20 | 10 | obs. | exp. | obs. | U | 30 | 20 | 10 |
| Transmission frequency: | 53.0 ± 2.4% | | | | | | | 47.7 ± 2.7% | | | | | |

To study the transmission frequency of hypervariable fragments (FIG. 7), the number of fragments detected by probes 33.6 and 33.15, out of n scored, which were transmitted to precisely r children in the sibship of 11 was compared with the expected number given by the binominal distribution $$\frac{^{11}C_r}{2^{11}} \cdot n$$

assuming 50% transmission (Table 4). Fragments present in all children may be from homozygous loci, and were ignored. Maternal fragments not transmitted to any children could not be scored since maternal DNA was not available. The mean transmission frequencies (+S.E.M.) are also given.

Linkage between pairs of fragments AB was investigated by scoring the number of offspring who were concordant for AB (either AB or —), using all possible pairwise comparisons of paternal or maternal fragments having first excluded alleles and linked bands (i.e. c loci were analysed in each parent, see Table 3, giving $$\frac{c(c-1)}{2}$$

pairwise comparisons). Pairs of fragments which fall into the zero- or 11-children classes represent alleles or tightly linked pairs respectively; by definition, no pairs fall into either class. The observed distribution is compared with that expected if all c loci are unlinked (U), in which case the number of pairwise comparisons which give precisely r (AB or —) offspring is given by the binomial distribution $$\frac{^{11}C_r}{2^{11}} \cdot \frac{c(c-1)}{2}$$

The distribution is also compared with that expected if the c loci are clustered and spaced uniformly, with adjacent loci being separated by a recombination frequency θ (10, 20 or 30 cM apart). The cluster will therefore be spread over (c-1)Ψ map units, where $\Psi = -\frac{1}{2}\ln$ (1-20). For c loci (sampled at one or other allele at random), the number of pairwise comparisons which give precisely r (AB and —) offspring in the sibship of 11 is given by:

$$\sum_{i=1}^{i=c-1}(c-i) \cdot {}^{11}C_r \left[ \frac{x_i^{11-n}(1-x_i)^n + x_i^n(1-x_i)^{11-n}}{2} \right]$$

where $x_i$ is the recombination fraction between two loci i map units apart; $x_i$ is given by the mapping function $$x_i = \tfrac{1}{2}(1-e)^{-2i\Psi}$$

Results

DNA Fingerprint Probes

Two minisatellite hybridisation probes used in this study are fully described in the main application. Probe 33.15 consists of a cloned human minisatellite comprised of 29 repeats of a 16 bp variant of the core sequence. The repeat unit of the minisatellite in probe 33.6 is a diverged trimer of the most conserved 11 bp 3' end of the core sequence and is repeated 18 times. The sequences of the core and probe repeat unit are:

| | | | | | | | | | | | | | | A | |
|---|---|---|---|---|---|---|---|---|---|---|---|---|---|---|---|
| core | G | G | A | G | G | T | G | G | G | C | A | G | G | A | G | G |
| 33.15 | A | G | A | G | G | T | G | G | G | C | A | G | G | T | G | G |
| 33.16 | | | | | A | G | G | G | C | T | G | G | A | G | G | |

The difference both in sequence and in repeat length of probes 33.6 and 33.15 results in their detecting different patterns of long hypervariable minisatellite fragments in HinfI digests of human DNA. This 4 bp restriction endonuclease maximises the resolution of variable minisatellites by releasing long tandem-repetitive minisatellites in DNA fragments with little flanking DNA.

Analysis of DNA Fingerprints in a Large Sibship

To investigate the segregation of individual minisatellite DNA fragments, a large sibship of 11 English individuals was segregated for neurofibromatosis (von Recklinghausen's disease), an autosomal dominant disorder associated with tumours of the peripheral and central nervous system. No genetic markers have yet been linked to this disease.

Blood DNA fingerprints, detected by probes 33.6 and 33.15, of the 11 children (6 affected, 5 unaffected) were compared with their unaffected father in FIG. 7. Resolution of minisatellite DNA fragments was maximised by electrophoresis in 35 cm long agarose gels.

Since many of these hypervariable minisatellites, particularly the largest DNA fragments, have low allele frequencies and are seldom shared by unrelated individuals as predicted, many of these fragments in the neurofibromatosis family are present in the heterozygous state and are transmitted to only some of the progeny. Even though the DNA of the affected mother was unavailable, maternally-derived minisatellite fragments could be readily identified as fragments present in some offspring but absent from the father. Paternal fragments could similarly be identified. Using both probes 33.6 and 33.15, it was possible to score the segregation of 41 paternal and 32 maternal DNA fragments in this sibship (FIG. 7, Table 3). Numerous additional polymorphic fragments also exist, but were either electrophoresed off the gel or were incompletely resolved and could not therefore be reliably scored.

Heterozygous paternal DNA fragments were transmitted on average to 53% of the progeny. Similarly, maternal fragments showed 48% transmission, again consistent with 1:1 segregation (Table 4). Furthermore, the number of children receiving each fragment followed the expected binomial distribution, in which the proportion of parental fragments which are transmitted to precisely r children in the sibship of 11 is $$\frac{^{11}C_r}{2^{11}}$$

(Table 4). It was concluded that these DNA fragments show Mendelian inheritance, and that the scoring of parental bands, particularly the smaller and less well-resolved fragments, is not significantly influenced by possible cases of segregation of two or more superimposed bands which would give an apparent ≧75% transmission frequency. The correct maternity and paternity of all sibs is also established by these DNA fingerprints.

By pairwise comparisons of the segregation patterns of all paternal or maternal DNA fragments in this large sibship, it is possible to identify allelic pairs of fragments plus pairs which show tight linkage in coupling (the odds of chance cosegregation of a given pair of bands in this sibship is 1/1024). Several instances of allelic pairs of both paternal and maternal fragments could be identified with both probes (FIG. 7). Probe 33.6 also detected a linked pair of fragments in both the mother and father. A similar linkage was found in a second pedigree (see below), which suggests that at least one of the hypervariable regions hybridising to probe 33.6 is a long minisatellite/satellite which contains internal cleavage site(s) for HinfI and is therefore cleaved to produce two or more fragments which cosegregate as a minisatellite "haplotype" in pedigrees. None of the polymorphic DNA fragments scored using probe 33.15 were present in the set of fragments detected by 33.6; any such fragment which hybridised to both probes would have been detected as bands of equal size which were transmitted from the same parent to the same children (i.e. "linked"). These two probes therefore hybridise to essentially completely different subsets of human minisatellites.

By eliminating alleles and linked fragments it was concluded that 34 and 25 distinct loci were scored in the father and mother respectively (Table 3). For ~80% of loci, only one of the two alleles is resolved, and the second allele is probably located in the poorly-resolved complex of shorter minisatellite fragments. This implies that large differences in minisatellite allele lengths must exist, arising presumably by unequal exchange in these tandem repetitive regions; several allelic pairs identified in FIG. 7 do indeed show substantial length differences. From the proportion of bands which can be paired into alleles, it is possible to estimate that the total number of heterozygous loci present in the entire DNA fingerprints detected by probes 33.6 and 33.15 is approximately 43–66, of which approximately half can be scored in the father and mother (Table 3). It is not possible to determine allelism between paternal and maternal fragments in this sibship.

All of the paternal loci scored are autosomal and do not show specific transmission either into daughters (X linkage) or sons (Y linkage). Furthermore, all pairs AB of paternal DNA fragments apparently segregate independently into offspring, to give on average equal numbers of (AB, —) and A-, -B) progeny; precise numbers followed the expected binomial distribution for unlinked loci (Table 4). Maternal DNA fragments behaved similarly. More detailed analysis suggests that the minimal locus-to-locus spacing for these loci must be ≧30 cM (46 map units); any closer spacing would generate significant numbers of pairs of fragments which tend to cosegregate (linked in coupling) or segregate as pseudo-alleles (linked in repulsion) (Table 4). The resolvable minisatellite loci must therefore be spread over at least half of the 3000 cM long human genome, and must therefore be scattered over many or all of the human autosomes.

One maternal minisatellite fragment (FIG. 7) shows weak evidence of linkage in coupling with neurofibromatosis, with 10/11 children being concordant for this fragment and the disease ($\theta = 10$ cM, p=0,006). Since, however, 25 different maternal loci have been scored, the probability that an allele of at least one of these loci would by chance show the observed degree of linkage in coupling or in repulsion is high (p=0.24).

EXAMPLE 9

DNA Fingerprints of an Extended Pedigree: Possible Linkage to HPFH

Analysis of DNA fingerprints was extended to a more extensive four-generation pedigree of Gujerati Asians which is segregating both for β-thalassaemia and for hereditary persistance of foetal haemoglobin (HPFH).

Autoradiographs of marker segregation patterns shown in FIGS. 8A and 8B were produced as follows.

10 μg samples of blood DNA were digested with HinfI, and DNA fingerprints were produced as described in FIG. 7, using probe 33.6 (A) or 33.15 (B). Electrophoresis was performed in a relatively short (20 cm) agarose gel. The relationship between individuals are given in FIG. 9. A, hypervariable fragments a, b and c are closely linked and are either all present or all absent in each individual in the pedigree. B, cosegregation of band g and HPFH (H). Individuals IV 7 and IV 8 are identical twins and have indistinguishable DNA fingerprints.

Materials and methods were as in Example 8.

Figure 9A:
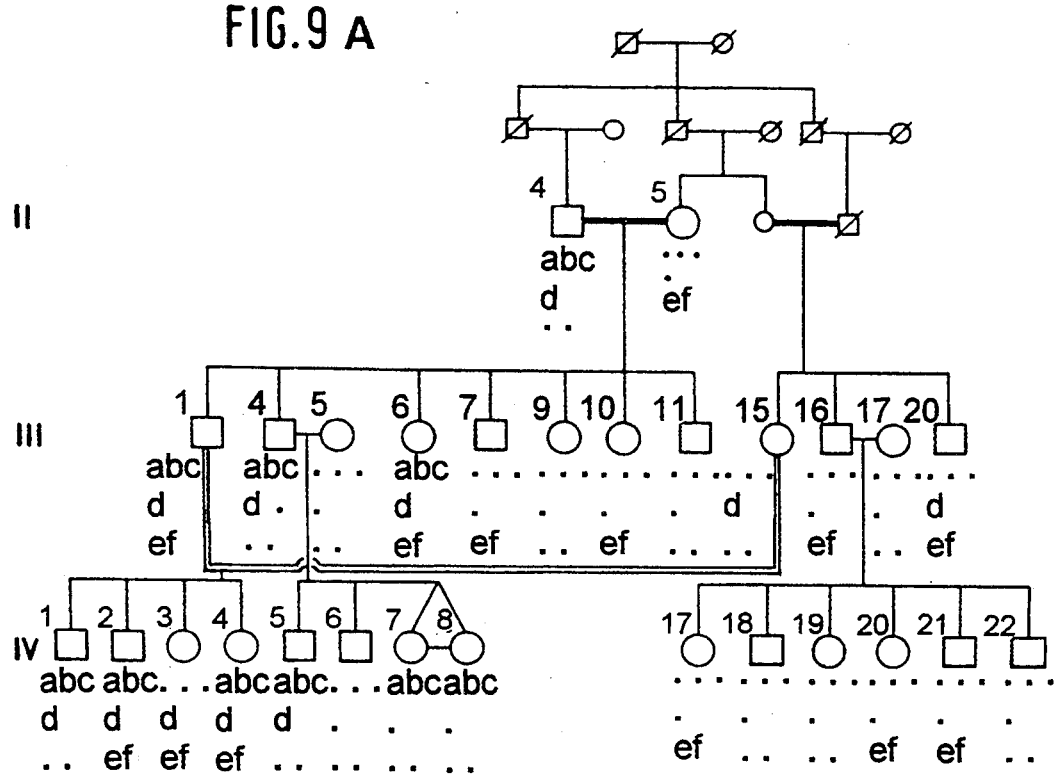
FIGS. 9a and 9b are genetic diagrams illustrating the inheritance of HPFH and of various minisatellites in a large pedigree.
Figure 9B:
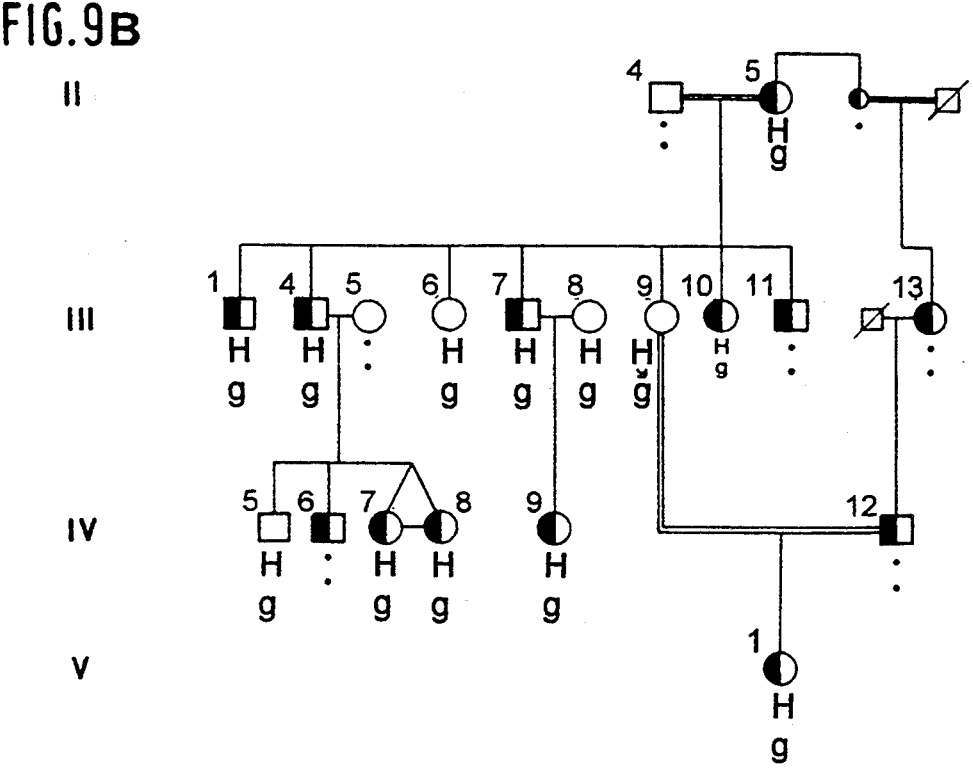

Co-segregation analysis is shown in FIGS. 9A and 9B.

In FIG. 9A, the segregation of 30 hypervariable fragments from II 4 and 27 fragments from II 5 into offspring III 1–11 was screened for possible linkage of pairs AB of parental fragments; possible examples of linkage showing at least 6/7 (AB, —) offspring were further examined in additional relatives. The two clearest examples of linkage are shown (a–f, presence of fragments a–f in an individual; ●, fragment absent). Fragments a–c and e,f each show perfect cosegregation; fragment d tends to cosegregate with a–c, but sibship IV 1–4 is uninformative and identical twins IV 7,8 are recombinant, having inherited a–c but not d. B, inheritance of -thalassaemia trait (●, ◻), HPFH (H) and minisatellite fragment g. Individuals are scored as having HPFH if they showed >1% HbF (normal) or >3% HbF (β-thalassaemia trait). HPFH and β-thalassaemia trait segregate independently in III 1-11 and IV 5-8 and are determined by unlinked loci. Fragment g cosegregates perfectly with HPFH in the individuals examined.

Results

As shown in FIG. 9A, B elevation of HbF is transmitted independently of β-thalassaemia trait, and is apparently determined by an autosomal dominant locus unlinked to the β-globin gene cluster. A similar Sardinian pedigree has been reported by Gianni et al, EMBO J.2, 921-925 (1983).

In FIGS. 8A and 8B, 30 variable fragments were scored in the grandfather (II 4) and 27 fragments in the grandmother (II 5). Study of their seven offspring (III 1-11) indicated that these fragments were derived from at least 22 distinct unlinked paternal and 18 maternal autosomal loci, using the criteria described for the neurofibromatosis family. The remaining DNA fragments showed evidence of allelism or linkage to other fragments, although proof with this small sibship is not possible (a given pair of parental DNA fragments has a 1/64 chance of fortuitously being transmitted B either linked or as alleles in a sibship of 7). Further evidence of linkage was sought in additional members of the pedigree, and the two strongest cases of linkage are shown in FIGS. 8 and 9. Fragments a, b and c detected by probe 33.6 are transmitted in perfect linkage from II 4 into his children (III 1-11) and thence grandchildren (IV 1-8); no recombinants were seen in 14 informative progeny ($p=4\times10^{-9}$ for three cosegregating bands). As discussed above, this suggests that fragments a-c represent a minisatellite "haplotype" derived from a single hypervariable locus. Band d detected by probe 33.15 also shows evidence of linkage to bands a-c; however, one sibship (IV 1-4) is uninformative since both parents carry fragment d, and another (IV 5-8) contains a recombinant (identical twins IV 7,8). The evidence of linkage between band d and the a-c cluster is therefore weak ($\theta=10$ cM, $p=0.01$). Maternal bands e (detected by 33.6) and f (detected by 33.15) also show tight linkage both in the descendants of II 4 and II 5, and in additional related sibships III 15-20 and IV 17-22, (20 informative progeny, no recombinants, $\theta=0$ cM, $p=10^{-6}$). Since probes 33.6 and 33.15 detect different sets of minisatellites and do not cross-hybridize to fragments e and f, these fragments may represent an example of authentic linkage between two different autosomal minisatellite loci. Finally, the two linkage groups (fragments a-c and e-f) are not alleles of the same locus. Individual III 1 is a compound heterozygote carrying both the paternal a-c cluster and the maternal e-f pair; both clusters are transmitted to two of his four children, establishing that they are not segregating as alleles but instead must be derived from two unlinked hypervariable regions.

None of the maternal (II 5) minisatellite fragments showed significant linkage to β-thalassaemia trait and are therefore not closely linked to the β-globin gene cluster on chromosome 11. In contrast, one maternal fragment (g) 8.6 kb in length cosegregated with HPFH in the seven offspring and in three informative sibships of grandchildren (FIG. 9). No recombinants were seen in 12 progeny, suggesting close linkage ($\theta=0$ cM, $p=2\times10^{-4}$). Even allowing for the fact that 17 loci in II 5 have been investigated, this linkage is still significant (the probability that an allele of at least one of the 17 scored loci would show cosegregation by chance with HPFH is 0.004). It has been further checked that fragment g in II 5 is a single minisatellite allele, and not two superimposed segregating DNA fragments, by investigating the DNA fingerprints of all individuals shown in FIG. 9, digested with Sau3A instead of HinfI; every positive fingerprint contained a corresponding Sau3A fragment of size similar to that of fragment g (8.2 kb vs. 8.6 kb), as expected for a single minisatellite fragment.

Discussion

Human pedigree analysis shows that the DNA fingerprints detected by minisatellite probes can be reliably used for studying the segregation of multiple heterozygous DNA fragments, even in families where one or other parent is unavailable for study. Using two such probes, it is possible to analyse up to 34 hypervariable loci simultaneously in a single individual, a rate of genetic marker generation which is far higher than that obtained by conventional methods, including RFLPs, in human genetics. The stable inheritance of variable minisatellite fragments together with the low population frequency of individual fragments makes them ideally suited to linkage analysis, as shown by the examples of linkage discovered in the two pedigrees analysed. We should stress that, while these hypervariable minisatellites may be recombination hotspots, the estimated rate of unequal exchange occurring at a long minisatellite (~0.001 per gamete) is not sufficient to perturb significantly the linkage between a minisatellite locus and a neighbouring gene such as a disease locus.

It is estimated that the total number of hypervariable loci detected together by minisatellite probes 33.6 and 33.15 is approximately 60. At least one of the two alleles of about half of these loci can be resolved in a given DNA fingerprint, and it therefore follows that in different DNA fingerprints, the spectrum of loci examined will not be identical. Most or all of these loci are genetically unlinked, and must therefore be scattered over a substantial proportion of the human genome. Their precise location is not known, and must await the cloning and regional localisation of individual hypervariable minisatellite loci. Curiously, no minisatellites have yet been found on the X or Y chromosome in either pedigree studied. We estimate that approximately 43 different loci have been scored for possible sex linkage in the father of the neurofibromatosis family together with individual II 4 in the HPFH family. Since the X and Y chromosomes together constitute ~5% of the genome of a male, then the probability that none of 43 randomly dispersed loci resides on these chromosomes is $(0.95)^{43}=0.1$; the apparent lack of sex-linked minisatellites is therefore not significant.

These dispersed hypervariable minisatellite loci are well suited to the search for markers linked to disease loci, as shown by the provisional examples of linkage to neurofibromatosis and to HPFH. Unlike conventional single-locus genetic analysis, linkage data cannot be pooled between unrelated small pedigrees, since a different minisatellite allele is likely to be associated with the disease locus in each pedigree. Instead, DNA fingerprints are only suitable for studying linkage, particularly of dominant disorders, in an extensive pedigree and most ideally in a single large sibship.

So far, probes 33.6 and 33.15 permit up to 34 autosomal hypervariable loci to be scored in an individual. The chance that at least one of these loci is closely linked to a given disease locus (within 10 cM) is 20%, assuming random dispersal of minisatellites throughout the 3000 cM long human linkage map. For extended pedigrees such as the HPFH family, this probability falls to ~10% since only one allele of most loci is scorable, and to detect linkage, this allele must be linked in coupling to the disease locus. To raise these probabilities above 50% would require the scoring of >104 hypervariable loci in a single large sibship and >208 loci in an extended pedigree. These numbers exceed the total number of loci detected by the two minisatellite probes used so far. However, probes 33.6 and 33.15 detect essentially totally different sets of hypervariable loci, which suggests that the total number of human minisatellites which contain various versions of the core sequence may be large.

In conventional human pedigree analysis using defined single-locus markers, evidence of linkage between a marker and a disease locus usually directly gives the approximate genomic location of the disease gene, and can be further established by analysing additional pedigrees. The converse is true for DNA fingerprints. Further analysis of possible linkage between a hypervariable DNA fragment and a disease is possible via isolation of the fragment by preparative gel electrophoresis and cloning. Locus-specific hybridisation probes can then be designed from the isolated minisatellite, either by using unique sequence DNA segments immediately flanking the minisatellite or by using the entire minisatellite in high stringency hybridisations. Such locus-specific probes can be used both to extend the linkage data in additional families and to localise the minisatellite within the human genome. This approach is currently being confirmed by cloning the 8.2 kb Sau3A minisatellite fragment apparently linked to the HPFH locus in the Gujerati pedigree.

As described above, probes 33.5, 33.6 and 33.15, each of which consists of a human minisatellite comprised in each case of a different variant of the core sequence, produce different DNA fingerprints and therefore detect different sets of hypervariable minisatellite regions in human and other vertebrate DNA. In particular, probes 33.6 and 33.15 detect largely or entirely different sets of minisatellites (cf. the third application and "DNA 'fingerprints' and linkage analysis in human pedigrees" by A. J. Jeffreys, V. Wilson, S. L. Thein, D. J. Weatherall & B. A. J. Ponder), as a result of differences both in length and precise sequence of the repeated core present in each probe.

To investigate the feasibility of detecting additional hypervariable regions using tandem repeats of other versions of the core sequence, a series of synthetic minisatellites have been prepared.

EXAMPLE 10

Synthesis and Cloning of an Artificial Minisatellite

Figure 10:
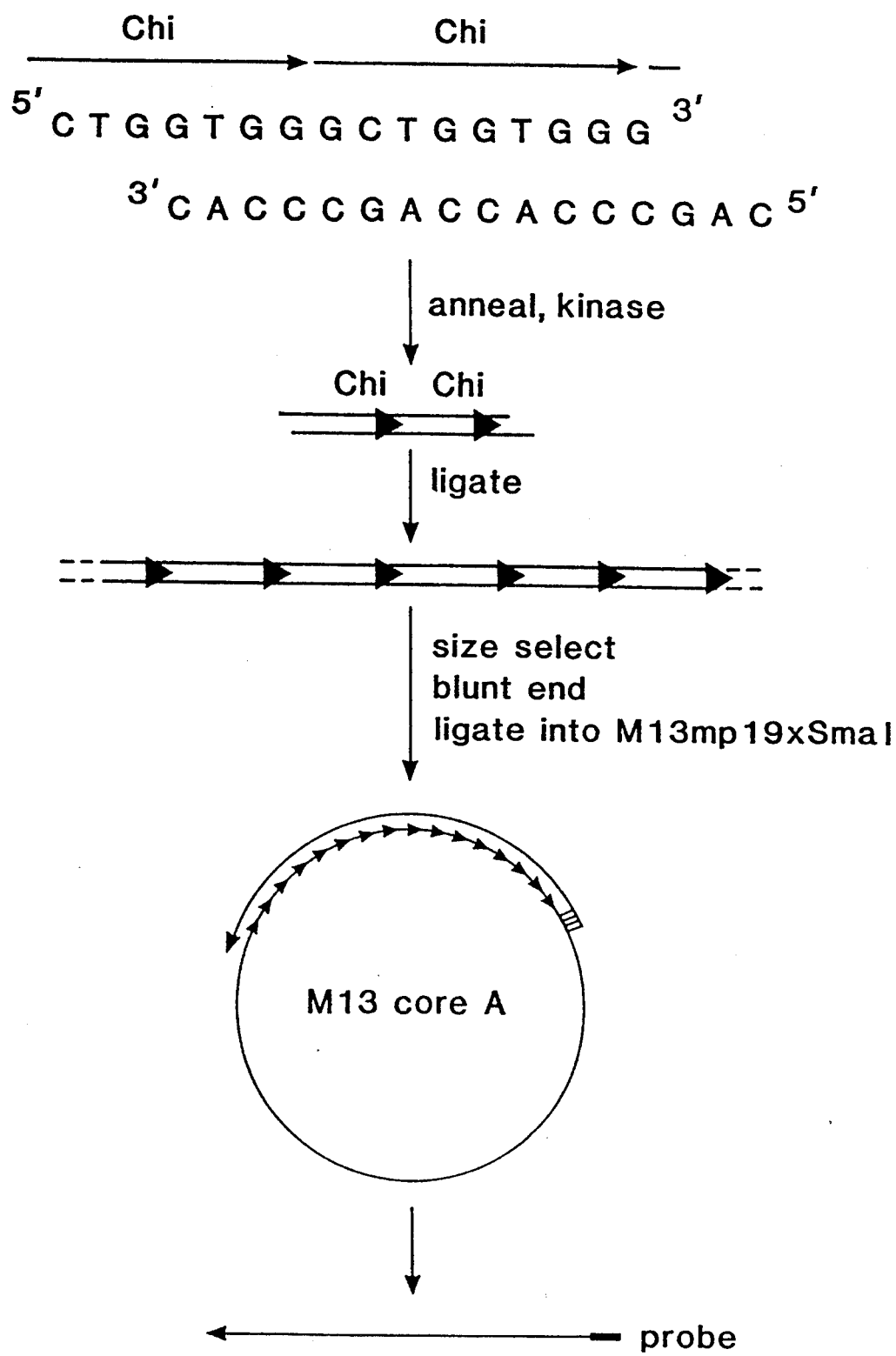
FIG. 10 is a diagram illustrating the preparation of a cloned artificial minisatellite.

The approach to preparing polycore probes is outlined in FIG. 10, which illustrates the route towards preparing a cloned tandem repeat of the crossover hotspot initiator sequence (Chi, GCTGGTGG) of *E. coli*. The steps involved in making a poly-Chi probe used standard DNA techniques and were:

1. A synthetic oligonucleotide containing a tandem repeat of the 8 nucleotide-long Chi sequence was prepared by the method of H. W. D. Matthes et al. (1984) (EMBO J. 3, 801-805) and D. G. Brenner & W. V. Shaw (1985) EMBO J. 4, 561-568. A second oligonucleotide consisting of a dimer of the complementary sequence of Chi was also synthesised.
2. These two oligonucleotides were annealed together at 37° in 10mM MgCl$_2$, 10 mM Tris-HCl (pH8.0) to form a short double-stranded segment of DNA. The sequence of the second oligonucleotide was chosen to produce an annealed molecule with 3-nucleotide long 5' projecting termini suitable for head-to-tail ligation.
3. The 5' termini were phosphorylated using T4 polynucleotide kinase plus ATP.
4. Annealed DNA fragments were ligated together in a head-to-tail fashion using T4 DNA ligase plus ATP to produce a repeated Chi polymer.
5. Ligated polymers were separated by size, by electrophoresis through a 1.5% agarose gel, and polymers greater than 150 base pairs in length were isolated by electrophoresis onto DE81 paper (Dretzen, G., Bellard, M., Sassone-Corri, P. & Chambon, P., 1981. Anal. Biochem. 112, 295-298).
6. The recovered long polymers were blunt-ended by fill-in repair using the Klenow fragment of *E. coli* DNA polymerase I and were ligated into the SmaI site of M13mp19 RF DNA (J. Messing & J. Vieira, 1982. Gene 19, 269-276). Ligated DNA was transformed into *E. coli* JM101 and single-stranded phage DNA isolated from individual white plaques.
7. The DNA insert of each cloned isolate was sequenced by the dideoxynucleotide method (M. D. Biggin, T. J. Gibson & H. F. Hong, 1983. Proc. Nat. Acad. Sci. U.S.A. 80, 3963-3965) to determine the length, orientation and sequence of the polymeric insert. One recombinant M13 phage was found, termed M13.core A, which contained 50 tandem repeats of the Chi sequence orientated 5'→3' in the mature single-stranded phage DNA [i.e. the insert is poly (Chi), not poly (complement of Chi)].
8. A $^{32}$P-labelled single-stranded hybridization probe was prepared by primer-extension, using the same methods as for preparing probes from phage 33.6 and 33.15.

EXAMPLES 11 TO 15

Preparation of Five Further New Artificial Minisatellites

Using the above technique, five further versions of the core sequence were synthesised and cloned as polycore recombinants in M13, to give recombinants M13.core A-F. The core variants were chosen so as to vary both the length and precise sequence of the core. Table 5 summarises the repeat sequence in clones M13.core A-F as compared with the core sequence and with previously-used probes 33.5, 33.6 and 33.15 described in the earlier applications. The most invariant bases in the core sequence are underlined. The orientation of each insert in the vector M13mp19 is also given (→, insert is poly(core); ←, insert is the complementary sequence of poly(core)). Bases given in lower script indicate departures from the core sequence. Brief characteristics of each sequence are summarised in the "comments".

TABLE 5

Characteristics of six artificial minisatellite probes (M13.core A-F)

| probe | sequence | bp | no. repeats | orientation | Homology (%) | comments |
|---|---|---|---|---|---|---|
| core | G G A G <u>G</u> T <u>G</u> <u>G</u> <u>G</u> <u>C</u> A <u>G</u> <u>G</u> A(A) <u>G</u> <u>G</u> | 16 | | | 100 | |
| 33.6 | (a) a G G G C t G G A G G | 11(12) | 3 × 18 | ← | (82) | |
| 33.15 | a G A G G T(C) G G G C A G G t G G | 16 | 29 | ← | (87.5) | |
| 33.5 | g G G A G G T G G G C A G G A G G | 17 | 14 | ← | (91) | |
| M13.core A | T G G G C t G G | 8 | 50 | → | 87.5 | Chi |
| M13.core B | G T G G G C A G G A A G | 12 | 7 | ← | 100 | short core |
| M13.core C | T G G G C A G | 7 | 47 | → | 100 | very short core |
| M13.core D | G G T G G G C A G G t G G | 13 | 5 | ← | 92 | short 33.15 |
| M13.core E | a G G G C A | 6 | 34 | → | 83 | very short 33.6/33.15 hybrid |
| M13.core F | A G G c a G G t A G G t G G | 14 | 9 | ← | 71 | short 33.15, TGGGCA disrputed |

EXAMPLE 16

Hybridization of M13.Core A-F to Human DNA Digested with HinfI

Figure 11:
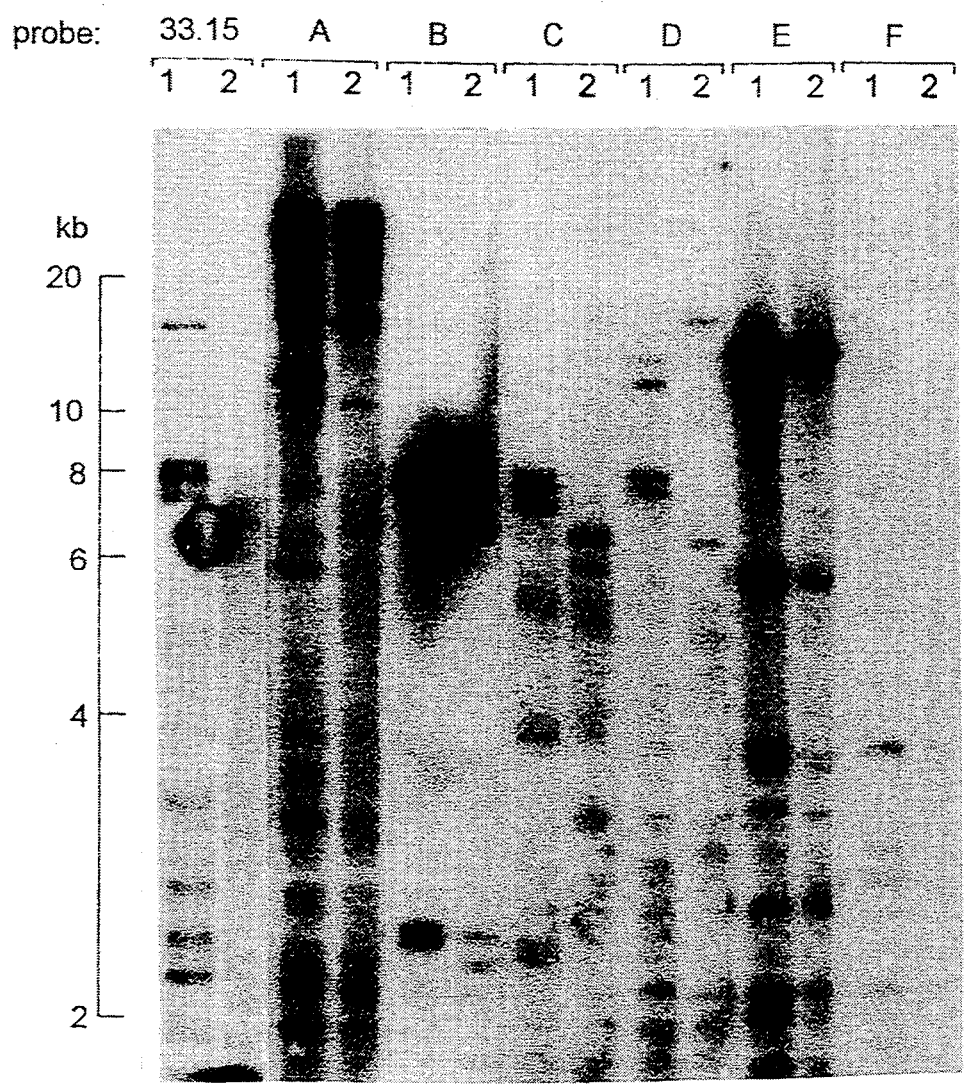
FIG. 11 shows a series of autoradiographs of DNA samples from two unrelated placentae, probed with novel synthetic probes.

In an initial screen, DNA digests of two unrelated individuals were probed with 33.15 and with each of the probes M13.core A-F. 8 μg samples of DNA from two unrelated placentae (1,2) were digested with HinfI, electrophoresed through a 0.7% agarose gel, Southern blotted and hybridized to each probe labelled with $^{32}$P following the procedure described in the main application. The resulting autoradiographs are shown in FIG. 11. All probes detected multiple DNA fragments in each individual.

Results

Probes B, C and D each detected a fingerprint of DNA fragments which differed substantially between the two individuals; the fingerprint also varied from probe to probe, though some fragments were detected by more than one probe and overlapped to some extent with the set of hypervariable fragments detected by probe 33.15. We conclude that probes B-D are all suitable for DNA fingerprinting and together will extend the number of hypervariable minisatellites which can be examined in humans and other vertebrates. Of interest here is the successful fingerprint obtained with core C, which contains only the central most conserved 7 base pair segment of the core sequence.

Further truncation of the core to produce the 6 base pair repeat in core E completely altered the DNA fingerprint pattern to reveal a set of fragments which are mostly shared by the two individuals tested (i.e. these fragments do not show extreme polymorphic variation). Thus core E is unlikely to be as useful a probe for DNA fingerprint analysis as the previously used probes 33.5, 33.6 and 33.15. This also suggests a practical minimum requirement of 7 base pairs of core sequences for generally successful DNA fingerprinting. Disruption of the central most conserved region of the core (M13.core F) also appears to reduce the complexity and variability of the DNA fingerprint pattern.

M13.core A (poly Chi) produces a novel and intense pattern of hybridizing DNA fragments. Many of these fragments are very large (>15 kb) and poorly resolved, and may well be derived from a conventional long satellite sequence which contains the occasional HinfI cleavage site. Some DNA fragments show individual variability.

EXAMPLE 17

Further Examination of Core A

Figure 12:
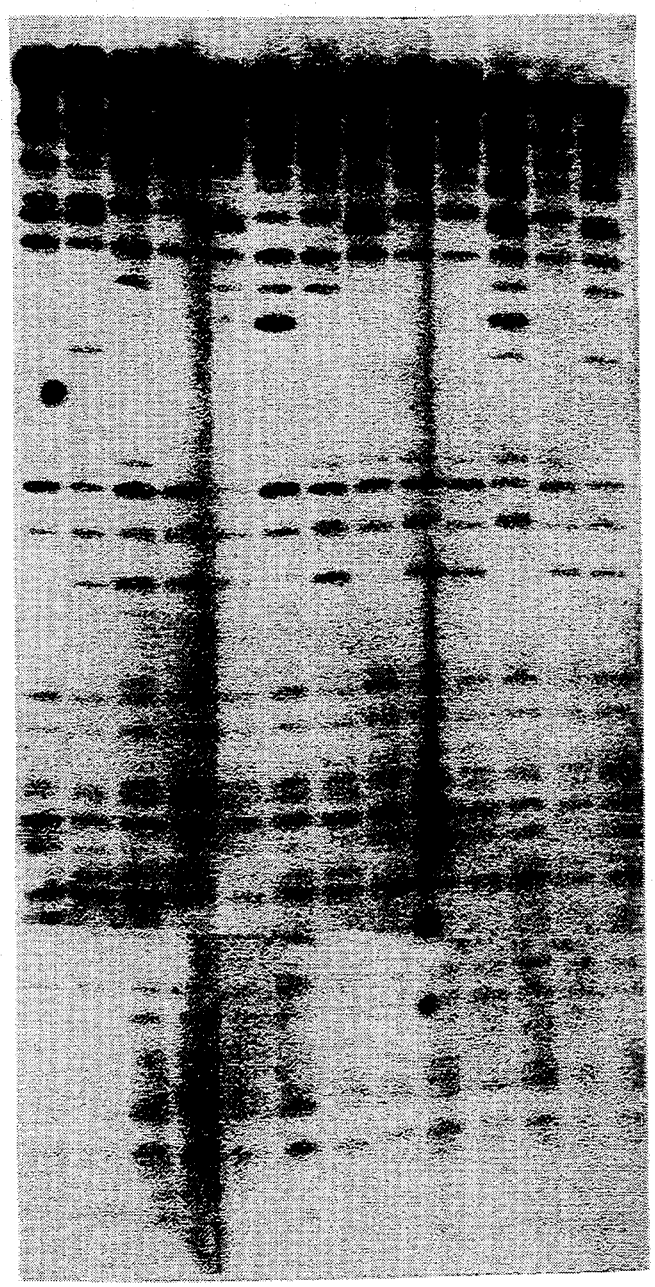
FIG. 12 shows a series of autoradiographs of probed DNA samples from a large sibship.

The patterns produced by M13.core A were further analysed in the family affected by neurofibromatosis, which has also been extensively characterised using probes 33.6 and 33.15 (cf Example 8 and FIG. 7). In FIG. 12, DNA fingerprints are shown from HinfI digests of DNA from the father (F), six daughters (D) and five sons (S). Individuals affected by neurofibromatosis, an autosomal dominant inherited cancer, are marked +; DNA from the affected mother was not available. Segregating paternal (●) and maternal (o) bands are indicated. Bands connected by a solid line are linked, and those connected by dotted lines are segregating as alleles. Bands marked (x) have been previously detected using probe 33.15.

Results

Unlike the DNA fingerprints obtained with probes 33.6 and 33.15, the level of variability is relatively low, with many fragments being transmitted to all offspring (i.e. these fragments are common, not rare, in the population and are frequently present in the homozygous state). The segregation of 6 heterozygous paternal and 9 heterozygous maternal bands could be scored in the sibship of 11 children. One of the paternal and an allelic pair of the maternal bands has been previously detected with probe 33.15. After eliminating allelic and linked pairs of bands we are left with 2 new paternal loci and 6 new maternal loci not previously scored with either probe 33.6 or 33.15, compared with 34 paternal and 25 maternal loci previously scored. The poly Chi probe is therefore of limited use in human genetic analysis.

The results of Examples 16 and 17 confirm the importance of the nine dominant nucleotides underlined in the top row of Table 5 and discussed earlier on page 18 of the main application. They also go a long way to confirm the prediction made in the main application that a minimum sequence of six nucleotides is necessary in a successful probe core. Thus, core E is representative of minimum utility and it is possible that other sequences of six nucleotides may show marginally improved utility, e.g. the sequence TGGGCA discussed later. The increase to seven nucleotides is quite dramatic within the framework of the investigation.

In attempting to define the essentials of a useful core sequence, the variants X and Y used above to indicate alternative nucleotides may usefully be extended to a complete logical group as indicated below:

| | |
|---|---|
| X = A or G | P = not G |
| Y = C or T | (Q = not A) |
| W = A or T | (R = not C) |
| V = C or G | (S = not T) |
| | (O = any) |

( ) = Not utilised in the following discussion.

Using this terminology, an aspect of the invention may be said to comprise a polynucleotide including the repeated core sequence below:

GPGGGCWGGWXG          (6)

The above of course indicates the most representative twelve nucleotide sequence. However, it has been shown that the seven nucleotide core C has also great utility and to include this with "permitted" variants from the above twelve core sequence, an aspect may be said to include also a polynucleotide comprising repeats of the seven core sequence below:

PGGGCWG          (7)

Preferably of course P will equal T as in core C. The other most favoured possibility would be A.

For the sake of clarity, the percentage homology has also been indicated in Table 3. As regards the artificial probes of this application, it should be noted that the repeats are exact repeats, so that the homology of the minisatellite as a whole can be indicated by the homology of the core sequence. This is not necessarily true of the earlier probes 33.6, 33.15 and 33.5 where the homology has been indicated in brackets. This is due to variants occurring between repeats. Core F is perhaps indicative of a minimum percentage homology for usefulness. However, this lack of concensus was perhaps exaggerated by disruption of the central grouping

TGGGCA          (8)

present in the core. It is noteworthy that the above grouping is present in the most successful probes B, C and D and is disrupted in all of the less successful probes A, E and F. It is therefore to be expected that more successful probes having a minimum 70% overall homology with formula (6) might be obtainable.

It is noteworthy that the central six polynucleotide grouping of formula (8)

TGGGCA has also been disrupted in core E. It is perhaps to be expected that a six nucleotide core sequence as above would be more successful, although the increase in length from six to seven nucleotides may prove to be a more dominating characteristic.

Accordingly, an aspect of the invention can be said to comprise a polynucleotide including repeats of the core sequence TGGGCA.

More generally, the invention can be said to include as an aspect a polynucleotide according to the "first" definition above in which the sequence TGGGCA is present in all the repeating sequences.

Viewed from another aspect, the invention can be said to include a modification of the polynucleotide of the "first" definition above in which "core" represents a sequence of at least six consecutive nucleotides, read in the same 5'→3' sense, selected from the sequence shown in formula (2); "core" does not necessarily have the same sequence in each repeating unit provided that all units contain the sequence TGGGCA.

Preferably the remaining groups of each unit will have at least 70% homology with the sequence of formula (6) (or more preferably) (2)) within the constraint of the overall unit length.

Determination of Twin Zygosity at Birth

Determination of zygosity in twins is of importance not only for epidemiological, genetic and obstetric studies but because of the difference in prognosis between monozygotic and dizygotic twins. Monozygotic, or identical, twins have lower birth weights, more medical complications and higher mortality rates than dizygotic twins. In Caucasians about 30% of newborn twins are of unlike sex and therefore dizygotic. Examination of the placental membrane shows another 20% of cases to be monochorionic and these are always monozygotic. The remaining 50%, a proportion which is relatively constant between populations, are of like sex, have diamniotic dichorionic placentae and may be either mono- or dizygotic. A variety of methods have been employed to determine zygosity in these cases, including assessment of general appearance, fingerprinting, skin grafting, taste testing and determination of genetic markers. The latter are the most reliable with an accuracy of 95–98%. However, large numbers of such markers must usually be investigated because of relatively low mean heterozygosities of most protein and antigen variants.

In the following Examples DNA from twelve sets of newborn twins was examined using minisatellite DNA probes as above described. DNA "fingerprints" obtained demonstrate such variability between individuals that only monozygous twins show identical patterns. In the seven cases where zygosity could be determined from sex observation or placental examination the DNA result agreed with these findings. In the other five twin pairs and in two sets of triplets DNA analysis allowed a rapid determination of zygosity. DNA probes in accordance with the invention therefore provide a single genetic test which should allow positive determination of zygosity in all cases of multiple pregnancy.

EXAMPLE 18

Single stranded DNA probes 33.6 and 33.15 were used to determine the zygosity of twelve sets of newborn twins, details of which are set out in Table 6.

TABLE 6

| Case | Gestational Age | Sexes | Placentation+ | DNA pattern |
|---|---|---|---|---|
| 1 | 38 weeks | FF | Monochorionic | Identical |
| 2 | 38 weeks | MF | Dichorionic | Non-identical |
| 3 | 30 weeks | MM | Dichorionic | Identical |
| 4 | 33 weeks | FF | Monochorionic | Identical |
| 5 | 40 weeks | FF | Dichorionic | Non-identical |
| 6 | 37 weeks | MF | Dichorionic | Non-identical |
| 7 | 32 weeks | FF | Dichorionic | Identical |
| 8 | 34 weeks | MF | Dichorionic | Non-identical |
| 9 | 39 weeks | MM | Dichorionic | Non-identical |
| 10 | 38 weeks | MF | Dichorionic | Non-identical |
| 11 | 27 weeks | MM | Dichorionic | Identical |

TABLE 6-continued

| Case | Gestational Age | Sexes | Placentation+ | DNA pattern |
|------|-----------------|-------|---------------|-------------|
| 12   | 35 weeks        | FF    | Dichorionic   | Non-identical |

+All placenlae were diamnionic.

Umbilical cord blood samples collected at delivery or peripheral blood samples (0.5–1.0 mls), obtained from each baby the day after birth, were used for DNA extraction. Placentae were examined to determine whether they were mono- or di- amniotic and chorionic. DNA was extracted by standard methods (Old, J. M., Higgs, D. R. Gene analysis. In: D. J. Weatherall, ed. The Thalassaemia. Methods in Haematology, Churchill Livingstone, 1983) and 10–15 μg digested with HinfI. Samples were electrophoresed through a 22 cm long 0.6% Agarose gel at 45 V for ~36 hours until all DNA fragments <1.5 kb long had electrophoresed off the gel. DNA was transferred by blotting to a nitrocellulose filter and baked at 80° under vacuum for two hours. The single stranded DNA probes, 33.15 and 33.6, were labelled with $^{32}$P as described previously.

Figure 13:
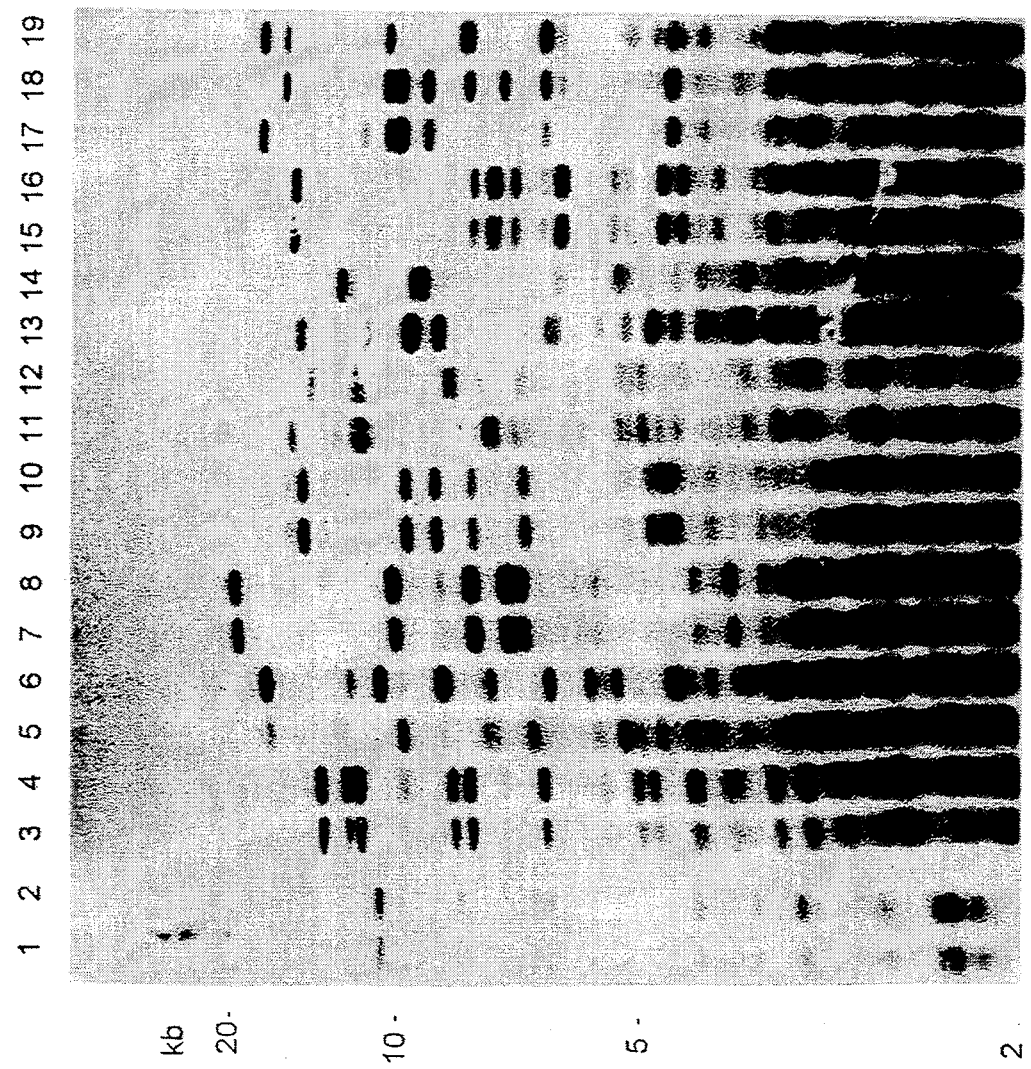
FIG. 13 is an autoradiograph showing various DNA band patterns obtained for twins using two different probes.

The results are shown in FIG. 13.

In FIG. 13, Lanes 1, 2 show the DNA band patterns obtained for each twin in Case 1 using the 33.6 single-stranded minisatellite probe. Lanes 3 to 19 show the "fingerprints" obtained with the single-stranded 33.15 probe:-Case 1, Lanes 3, 4; Case 2, Lanes 5, 6; Case 3, Lanes 7, 8; Case Lanes 9, 10; Case 5, Lanes 11, 12; Case 6, Lanes 13, 14; Case 7, Lanes 15, 16. Lanes 17–19 are three triplets of female, male and female sex. Comparison of Lanes 1 and 2 with Lanes 3 and 4 shows that the two probes, 33.6 and 33.15, detect different sets of minisatellite bands. Size markers are shown in kilobases.

In seven cases (see Table 6), zygosity could be determined simply by examination of the sex of the twins and their placental membranes. All twins with monochorionic (or monoamniotic) placentae (e.g. Case 1) are monozygotic, although only about 50% of monozygotic twins have monochorionic placentae (2). Hence, the twins in case 1 must be monozygotic and they showed identical DNA patterns with both the 33.15 and 33.6 probes (FIG. 1). In five cases the twins were of different sex and showed different band patterns with both the 33.15 and 33.6 probes. In cases 3, 5, 7, 9 and 11 the twins were of like sex and had dichorionic placentae, so these could be either mono- or di-zygotic. DNA analysis showed that two sets of twins (cases 5 and 9) had different band patterns and were, therefore, dizygotic whereas in the other three sets (Cases 3, 7 and 11) identical band patterns indicated monozygosity.

Two sets of newborn triplets were similarly studied. In both cases the mother had taken fertility drugs to induce pregnancy and each triplet showed a unique band pattern (e.g. Lane 17–19, FIG. 13).

Figure 14:
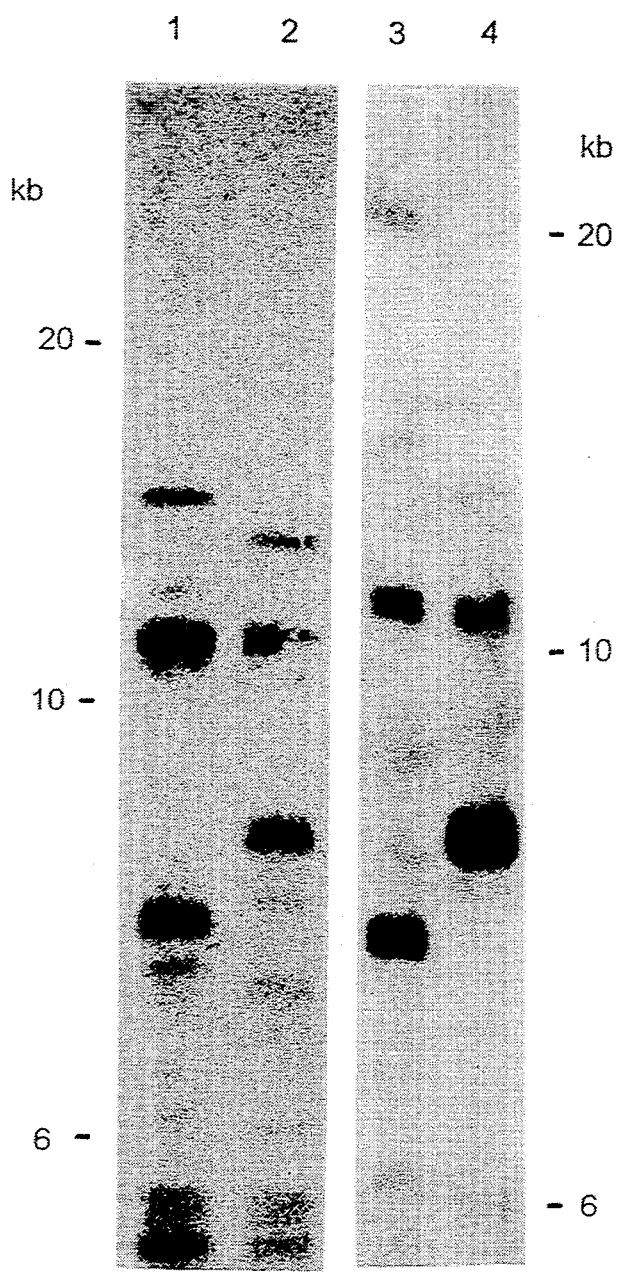
FIG. 14 is an autoradiograph comparing band patterns produced using single stranded and double stranded probes.

The results are shown in FIG. 14, in which Lanes 1 and 2 show the results using single stranded 33.15 and Lanes 3 and 4 the results using double stranded 33.15.

EXAMPLE 19

Although either single- or double-stranded probes were adequate to make each diagnosis, more bands were distinguishable with more radioactive single-stranded probes (FIG. 14).

As an alternative to these single-stranded probes we have investigated the possibility of using the corresponding double-stranded probes which may be more familiar in most laboratories. The double-stranded DNa probes used were i) a double-stranded 600 bp Pst I - Aha III fragment containing the "core" minisatellite from λ33.15 and ii) a double-stranded 720 bp Hae III fragment containing the "core" minisatellite from λ33.6. These were labelled by nick-translation to a specific activity of 0.5–1.0×10$^9$ cpm $^{32}$P/μg DNA. Prehybridisation and hybridisation conditions were as described in the above identified standard method except that 1×SSC and 10% dextran sulphate were used in the hybridisation buffer for the double-stranded probes. Filters were washed for 1 hour in 1×SSC at 65° C. and autoradiographed with intensifying screens for 1–3 days at −70° C.

DISCUSSION OF EXAMPLES 18 AND 19

In the seven cases where zygosity could be determined independently the DNA results were in agreement with the conclusion based on observations of Sex and placental examination. In the other five pairs, a clearcut determination of zygosity was possible with the minisatellite probes. Similarly both sets of triplets studied were shown to be trizygotic.

In the 50% of cases where twin zygosity cannot be determined by either unlike sex (dizygotic) or a monochorionic placenta (monozygotic), genetic analysis must be employed. The informativeness of such tests is proportional to the extent of polymorphism at the genetic loci under investigation and to the number of loci tested. With multiple red cell antigen and enzyme determinations accuracies of zygosity of the order of 95–98% may be achieved but only if the relevant allele frequencies in the population are known (Nylander, P. P. S. The phenomenon of twinning. In: Barron, S. L., Thomson, A. M. eds. Obstetrical Epidemiology. London. Academic Press, 1983: 143–165). Similarly, analysis of multiple restriction enzyme site polymorphisms with several different DNA probes produces a significant percentage of "false positive" diagnosis of monozygosity (Derom, C., Bakker, E., Vlietineck, R., Derom, R., Van der Berghe, H., Thiery, M., Pearson, P. Zygosity determination in newborn twins using DNA variants. J. Med. Genet., 1985, 22:279–282). Minisatellite probes in accordance with this invention overcome this problem because of the large number and substantial variability of the hypervariable DNA segments which they detect. As already described, hybridising minisatellite fragments are seldom shared between randomly selected individuals (compare also unrelated individuals in FIG. 13). It has already been shown above that the odds against two unrelated individuals showing identical DNA fingerprints with both probes 33.6 and 33.15, which detect different sets of hypervariable loci are therefore astronomical ($p < <10^{-18}$, see Example 4). In sibs who share about half of their fragments in common, the probability of such a "false positive" diagnosis of genetic identity is $<10^{-8}$. Hence, the combined use of single-stranded hybridisation probes 33.6 and 33.15 provides an accuracy which is orders of magnitude greater than previous genetic tests. Even using the more conventional double-stranded minisatellite probes which fail to hybridise to some of the fainter bands detected by single-stranded probes (FIG. 14), sufficient information can be obtained from DNA fingerprints to reduce the "false monozygosity" rate to $<10^{-1}$.

Another advantage of this method of zygosity determination is that very little sample is required for the analysis. Half a ml of peripheral or cord blood always provided sufficient DNA. With the availability of this straightforward means of determining zygosity in newborn as well as older twins and triplets, more precise epidemological studies on the determinants and effects of different types of multiple pregnancy should be possible.

In the following Examples molecular weight markers are not given in the autoradiographs but the effective general range was 1.5 to 20 kb as in other results.

Application of DNA Fingerprinting to Forensic Science

The individual specificity of DNA fingerprints detected by minisatellite probes 33.6 and 33.15 make them ideally suited to individual identification in forensic science. The only uncertainty is whether DNA survives in a sufficiently undegraded form in, for example, dried blood or semen stains to permit DNA fingerprint analysis. To determine the feasibility of analysing forensic specimens, a pilot study was carried out upon DNA samples supplied by Dr. Peter Gill of the Home Office Central Research Establishment, Aldermaston.

EXAMPLE 20

Dried blood and semen stains on cloth were left for various periods at room temperature prior to DNA extraction carried out by Dr. Gill (lysis with SDS in the presence of 1M DTT followed by phenol extraction and ethanol precipitation). DNA was similarly extracted from fresh hair roots and from vaginal swabs taken before and after sexual intercourse. DNA samples were digested with HinfI, electrophoresed through a 0.8% agarose gel and blotted onto a nitrocellulose filter. The filter was hybridised with $^{32}$P-labelled single stranded probe 33.15, using our standard technique as above described.

Samples electrophoresed were:
1. 40 μl semen stain on cloth, 4 weeks old.
2. 40 μl fresh semen.
3. 60 μl fresh blood.
4. 60 μl blood stain on cloth, 4 weeks old.
5. 60 μl blood stain on cloth, 2 years old.
6. 15 hair roots. NB. 1–6 were taken from the same man.
7. 60 μl blood stain on cloth, male, fresh.
8. vaginal swab taken from 11, one hour after intercourse with 7.
9. as in 8, but 7 hr after intercourse.
10. vaginal swab taken from 11.
11. 60 μl blood stain on cloth, female, fresh.

Figure 15:
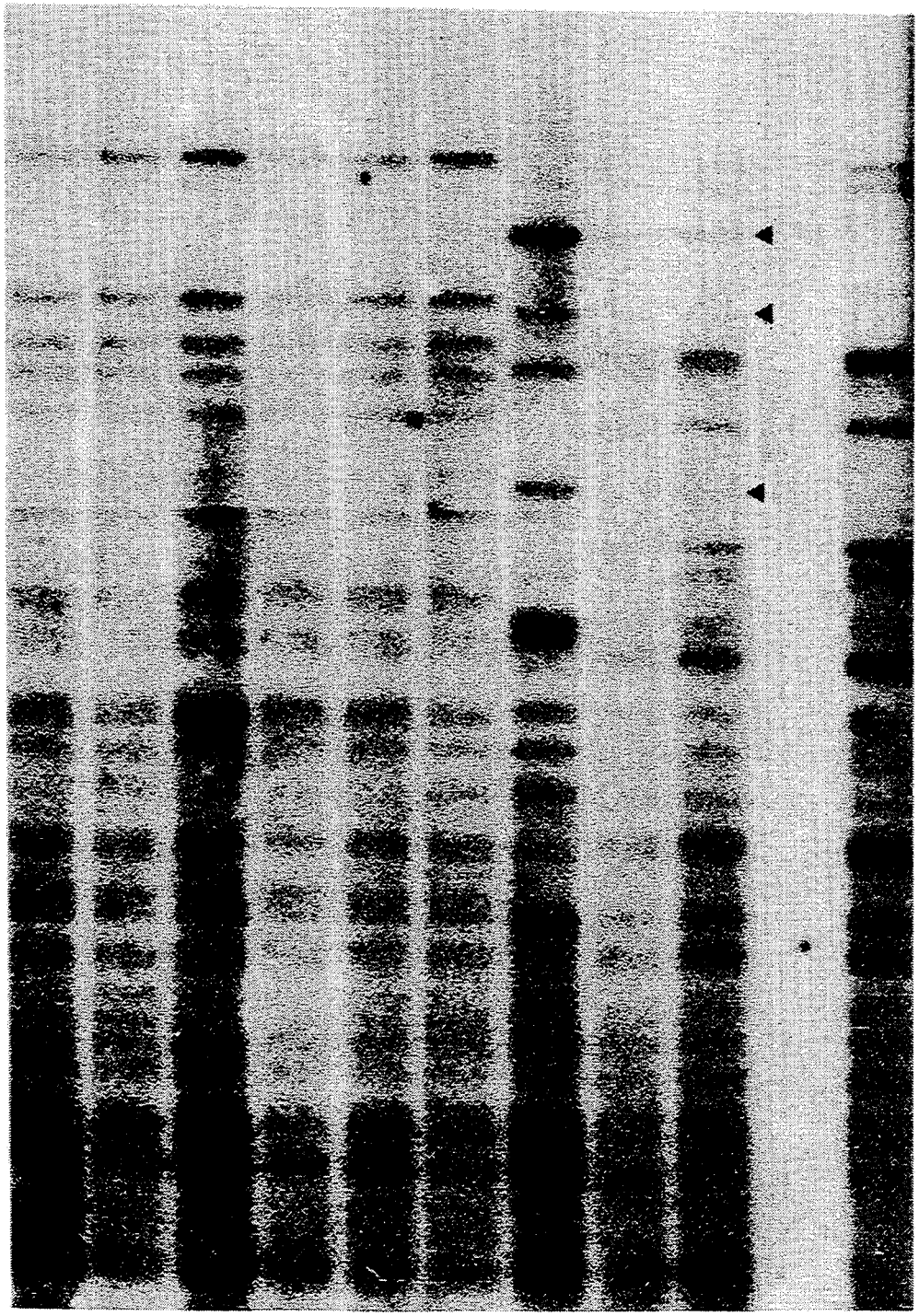
Figure 15:
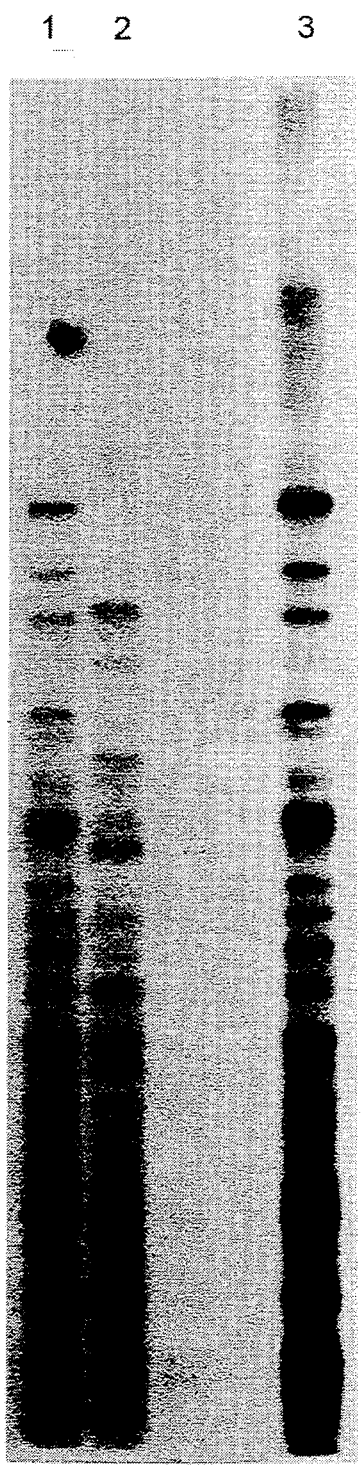

The DNA fingerprints obtained are shown in FIG. 15. Sufficient DNA (~0.5–3 μg) was extracted from each sample for analysis. DNA in dried blood stains up to 2 years old and in dried semen up to 1 month old was not significantly degraded and gave identical DNA fingerprints to those obtained from fresh blood and semen from the same individual. A DNA fingerprint could likewise be obtained from as little as 15 hair roots.

The vaginal swabs taken after intercourse also gave an undegraded DNA fingerprint. However, the swab patterns primarily matched that of the woman's, not the man's blood, which indicated that most DNA collected from the swabs was from vaginal epithelial cells sloughed off during swabbing, and not from sperm. Nevertheless, three additional non-female bands could be detected in the post-coital samples; these matched the principal bands in the man's blood and must have been derived from sperm; such bands could be detected in a sample taken 7 hrs after intercourse.

Discussion

These preliminary results indicate that DNA is maintained intact in a variety of forensic specimens and therefore that DNA fingerprinting for identification purposes is applicable to at least some forensic samples. For example, positive identification of a rapist from semen stains from a victim's clothing is now possible. The situation with vaginal swabs from rape victims is less certain in view of the contaminating vaginal DNA; however, removal of this female DNA by sds lysis prior to 2-DTT or mercaptoethanol-mediated reduction of sperm needed for isolation of sperm DNA should produce a clearer sperm DNA fingerprint. Identification of rapists should then be possible by DNA fingerprint analysis of semen stains and/or vaginal swabs.

It has since been confirmed in a recent study in cooperation with Dr. Gill that clear "fingerprints" of sperm DNA may be obtained from vaginal swabs after intercourse using a preliminary separation technique generally as described above.

FIG. 15A shows DNA fingerprints (Lane 3) from two vaginal swabs taken 6.5 h after intercourse. In Lane 1 there is shown a fingerprint from a blood sample from the male partner and in Lane 2 there is shown a DNA fingerprint from blood obtained from the female partner. Female cell nuclei from the swabs were preferentially lysed by preliminary incubation in an SDS/proteinase K mixture. Sperm nuclei are impervious to this treatment and can therefore be separated from the female component by centrifugation. Sperm nuclei were subsequently lysed by treatment with an SDS/proteinase K/DTT mixture.

It is apparent that this separation procedure was wholly successful. The sperm DNA fingerprints from semen-contaminated vaginal swabs perfectly matched fingerprints obtained from the blood of the male partner.

DNA Fingerprints of Economically-Important Animals Obtained Using Human Minisatellite Probes

EXAMPLE 21 TO 25

DNA samples were prepared from blood taken from dogs, cats, sheep, pigs, horses, and cattle. 8 μg samples were digested with a suitable restriction endonuclease (HinfI unless otherwise indicated) and the restriction digests were recovered after phenol extraction by ethanol precipitation. Restriction digests were redissolved in water, electrophoresed through a 0.7% agarose gel, denatured, transferred to a Schleicher-Schuell nitrocellulose filter and hybridised as described previously with $^{32}$P-labelled human minisatellite probes 33.6 or 33.15.

EXAMPLE 21 DOGS

Figure 16:
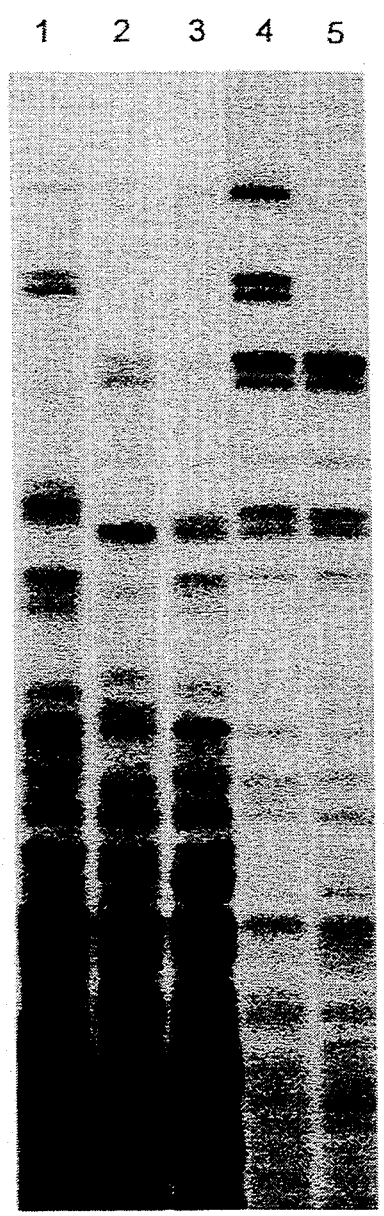
FIG. 16 is an autoradiograph showing DNA fingerprints obtained from a dog family.

DNA fingerprints obtained from a dog family using probe 33.6 are shown in FIG. 16. Samples electrophoresed were:
Lane 1. Beagle father
Lane 2. Greyhound mother.
Lanes 3,4,5. "Greagle" offspring pups of these parents (female, male, male respectively).

A detailed DNA fingerprint, similar in complexity to those derived from human DNA, was obtained from each dog. The DNA fingerprints showed substantial variability, as can be seen by comparing the patterns obtained from the father and mother (Lanes 1, 2). All three offspring have different DNA fingerprints, in each case comprised of bands all of which can be traced back to the father and/or mother. These DNA fingerprints are therefore of use in paternity testing and pedigree analysis in dogs, as in humans.

The DNA's in samples 1–3 were slightly degraded, thereby preferentially reducing the intensities of the largest (most slowly migrating) bands. Despite this degradation, the transmission of bands from parents to offspring could be readily determined.

EXAMPLE 22 CATS

Figure 17:
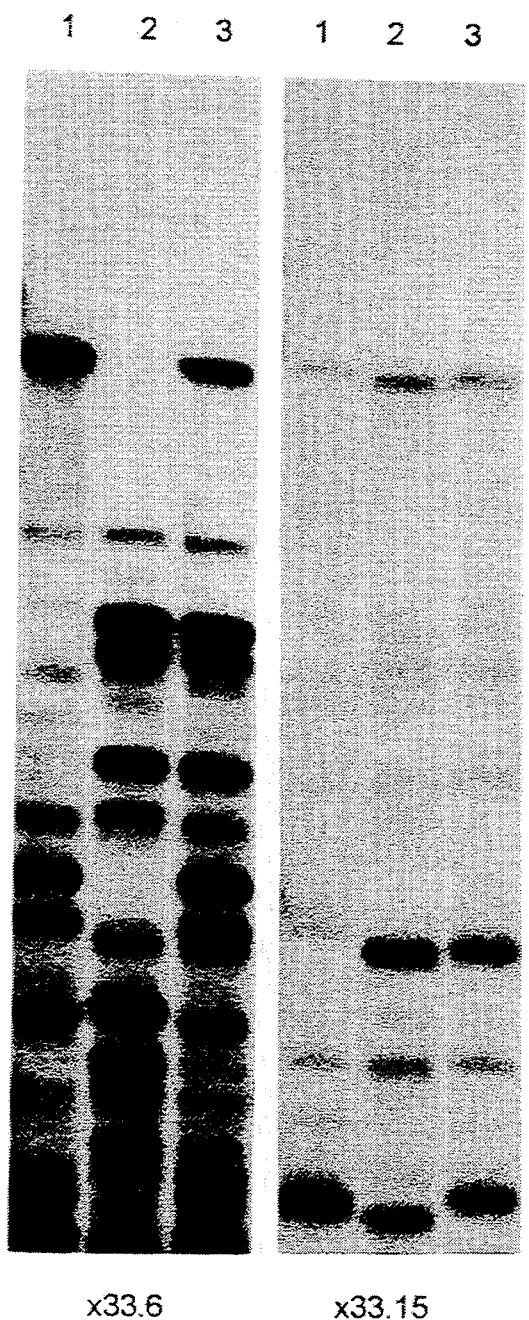
FIG. 17 is an autoradiograph showing DNA fingerprints from a short-haired domestic cat family.

FIG. 17 shows DNA fingerprints from a short-haired domestic cat family using (left) probe 33.6 and (right) probe 33.15.
Lane 1. mother
Lane 2. father
Lane 3. kitten Both probes 33.6 and 33.15 produce informative DNA fingerprints. Most bands in the kitten can be scored as being maternal or paternal and thus these DNA fingerprints are suitable for pedigree testing as well as for individual indentification in cats.

EXAMPLE 23 SHEEP

Figure 18:
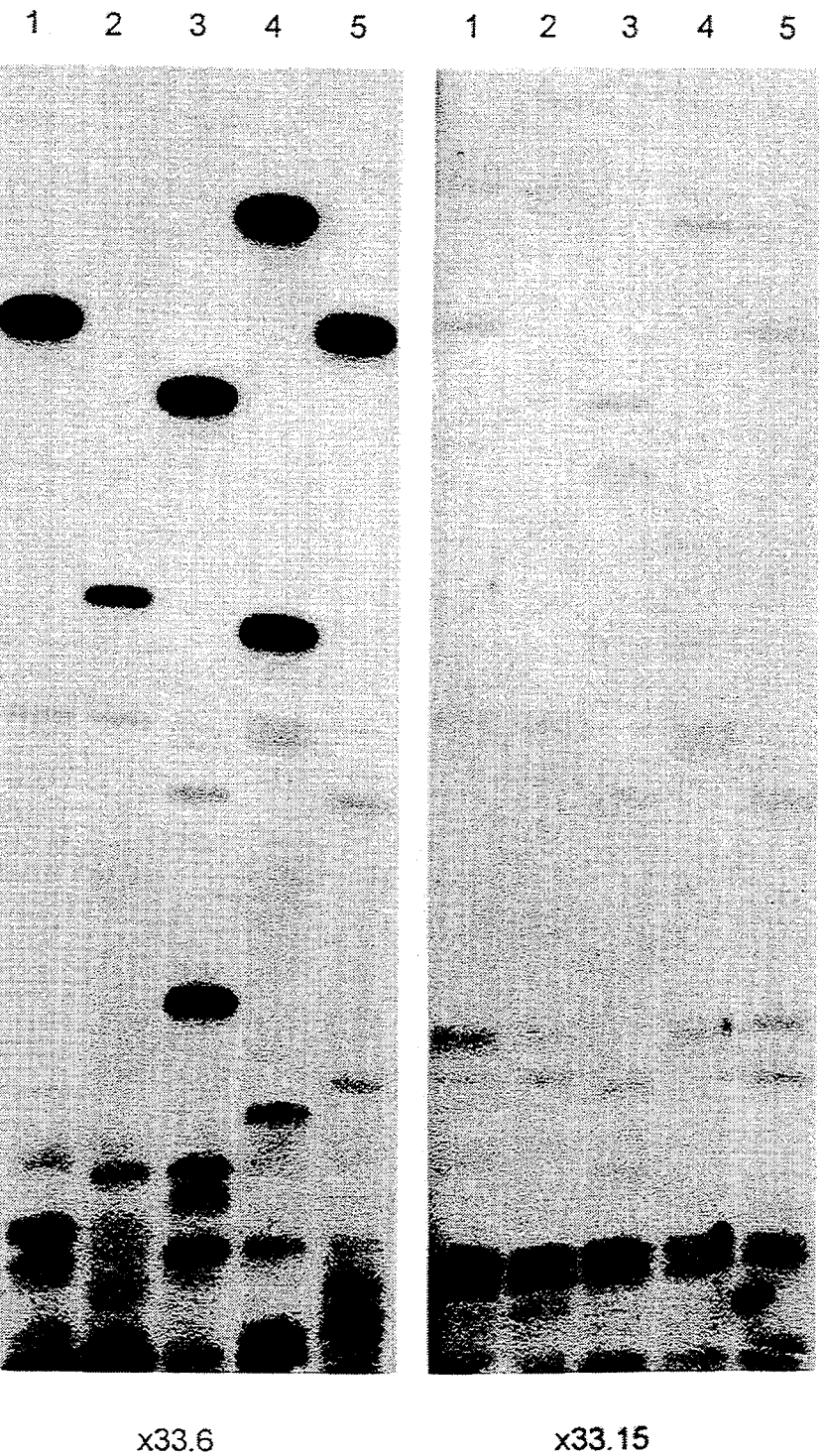
FIG. 18 is an autoradiograph showing DNA fingerprints obtained from various sheep using two different probes.

DNA fingerprints obtained from various sheep using probes 33.6 (left) and 33.15 (right) are shown in FIG. 18. Samples were:
Lane 1. Crossbred female
Lane 2. Crossbred female
Lane 3. Dorset female
Lane 4. Hampshire×Dorset female
Lane 5. Dorset male Individual-specific DNA fingerprints were obtained from each sheep with both probes. The DNA fingerprints are fainter and less complex than human DNA fingerprints but still of use for identification and genetic purposes. Probe 33.6 detects one or two very intense polymorphic bands in each sheep, in addition to a range of fainter bands. These bands are probably derived from a single minisatellite locus which by chance shows a very high degree of homology to probe 33.6.

EXAMPLE 24 PIGS AND HORSES

Figure 19:
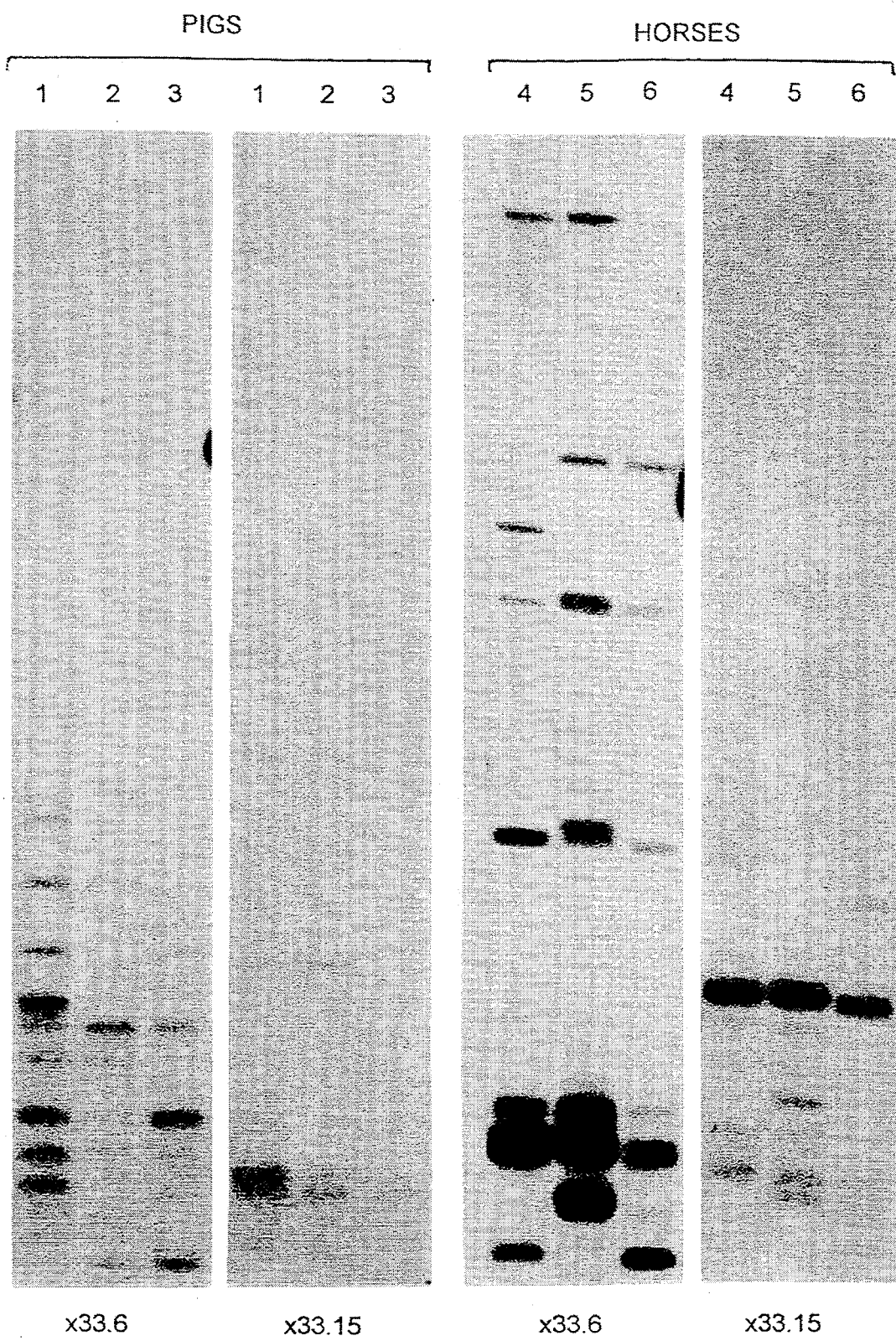
FIG. 19 is an autoradiograph showing DNA fingerprints from three different pigs.

FIG. 19 shows DNA fingerprints from three different pigs (Lanes 1–3) and three different horses (Lanes 4–6) [sex and breed not specified]. Both probes 33.6 and 33.15 produce individual-specific DNA fingerprints with each species. The DNA fingerprints, particularly with probe 33.15, are faint and contain very few bands compared with the corresponding human DNA fingerprints, but nevertheless the combined use of both probes will be of use in individual indentification.

EXAMPLE 25 CATTLE

Figure 20:
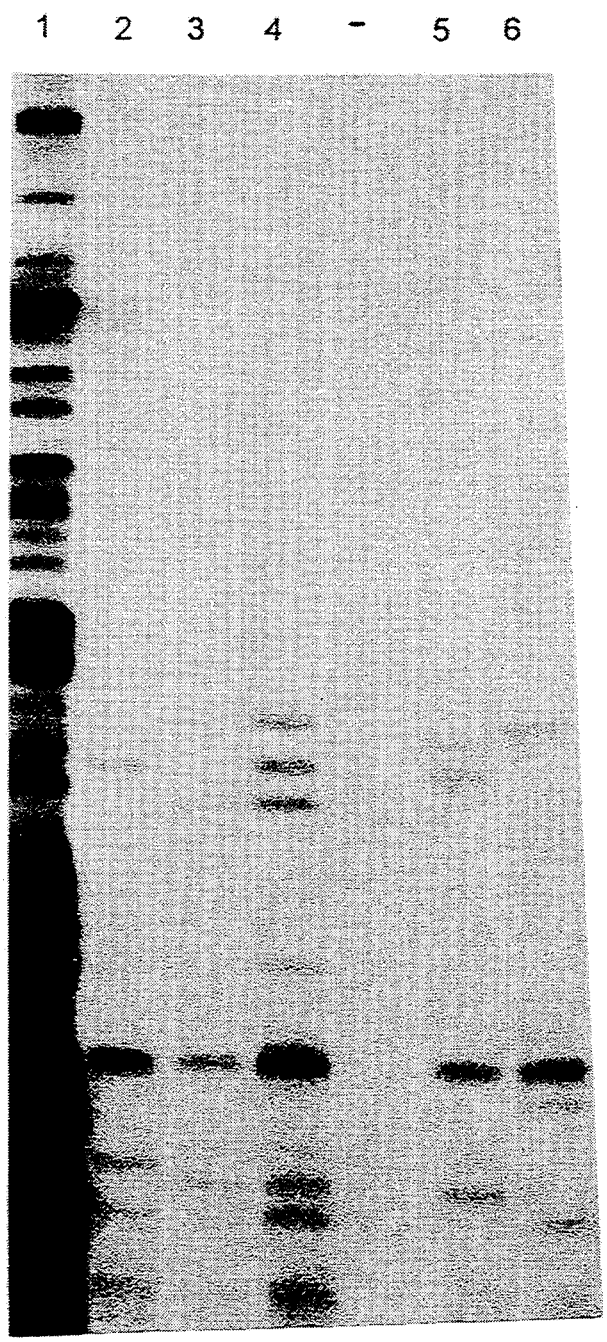
FIG. 20 is an autoradiograph showing DNA fingerprints for a cow family and additional cattle.

FIG. 20 shows DNA fingerprints of HinfI DNA digests obtained with probe 33.6 on a cow family and on additional cattle. Samples are:
[Lane 1. Human[
Lane 2. Dam
Lane 3. Sire
Lane 4. Calf of 1 and 2
Lane 5. Angus bull
Lane 6. Fresian bull As with sheep, pigs and horses, a fairly simple but nevertheless individual-specific DNA fingerprint was obtained from each animal. In the calf, all bands could be traced back to the dam and/or sire, confirming the pedigree of this animal.

Figure 21:
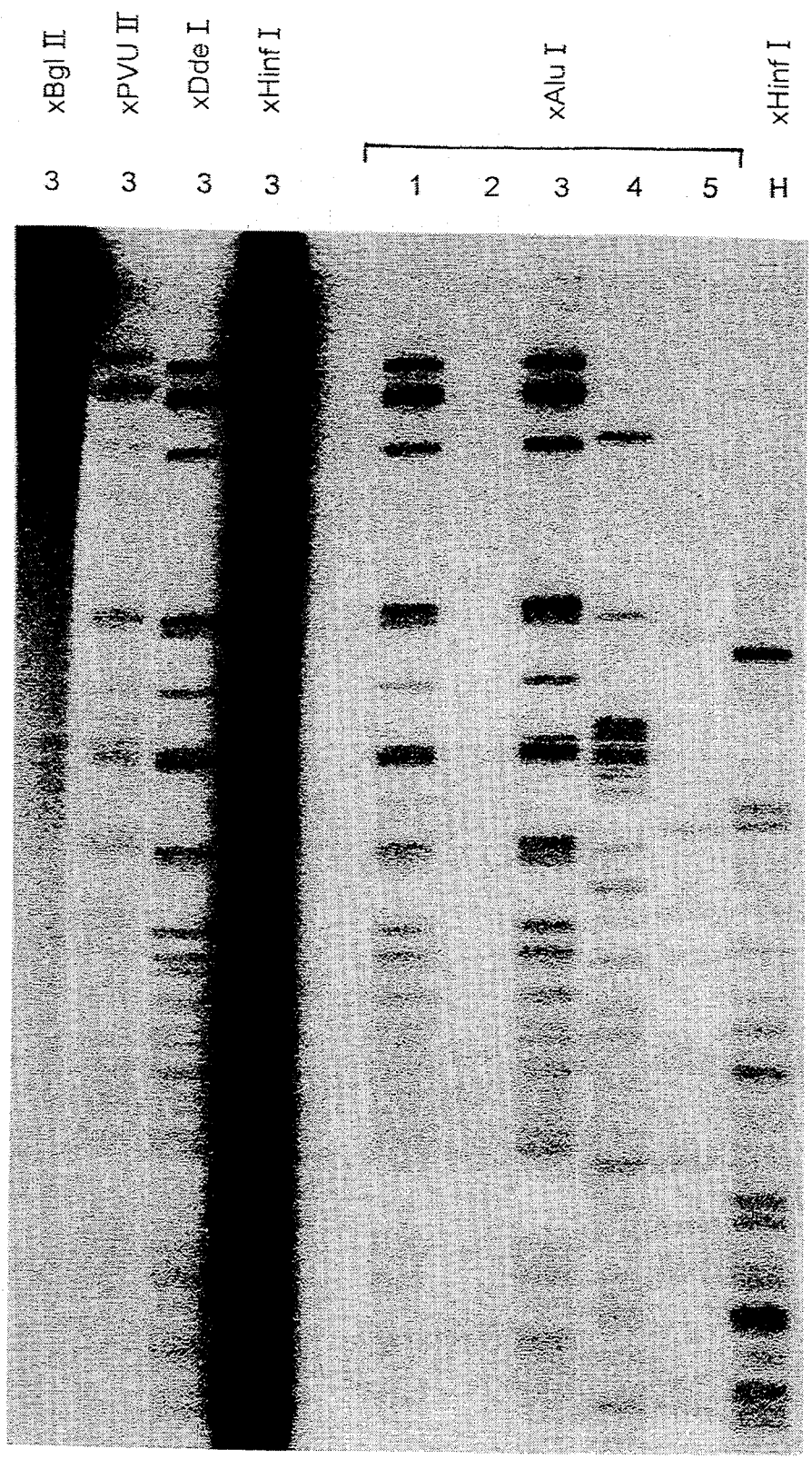
FIG. 21 is an autoradiograph similar to FIG. 20 utilising a different probe.

FIG. 21 shows results with probe 33.15 on the same cow DNA. Individual Lanes are marked:
1. Dam
2. Sire
3. Calf of 1 and 2
4. Angus bull
5. Fresian bull
[6. Human]

Probe 33.15 produces an intense and irresolvably-complex pattern of hybridising DNA bands in cow DNA digested with HinfI. In a BglII digest, this intense signal is mainly confined to very large DNA fragments, suggesting that this signal is derived from a clustered sequence or region—most likely, a conventional satellite DNA. Short autoradiographic exposure of the HinfI digest shows a "ladder" of bands towards the bottom of the gel, with a periodicity between "rungs" of 45–50 base pairs (data not shown). Thus the intense signal is most likely derived from a satellite with a repeat unit 45–50 base pairs long. The intense signal is largely destroyed in cow DNA digested with PvuII, DdeI or AluI, suggesting that the satellite DNA repeat unit contains one or more sites for each of these restriction endonucleases, but not for HinfI or BglII. These are precisely the properties of the 1.720 cow satellite (E. Poschl and R. E. Streek "Prototype sequence of bovine 1.720 satellite DNA". J. Mol. Biol. 143, 147–153; 1980) which consists of 100,000 tandem repeats of a 46 base pair repeat unit. Comparisons of the sequence of the 1.720 repeat unit with the core probe 33.6 repeat unit and 33.15 repeat unit are given below:

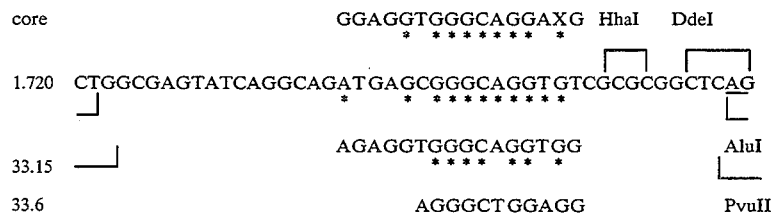

As can be seen, the 1.720 satellite repeat unit contains a near-perfect copy-of the 3' region of the core sequence (matches indicated by * above). This region in the 1.720 repeat gives an excellent match with the repeat unit of 33.15 but a less-perfect match with 33.6. This explains why. 1.720 satellite DNA is detected by probe 33.15 but not 33.6 (FIG. 20). (The 1.720 satellite repeat unit (like that of the myoglobin λ33 minisatellite) contains too many nucleotides on each side of the core (H+J in formula (1) >15) to act as a multi-locus probe in accordance with the invention).

In order to detect cow minisatellites which hybridize to probe 33.15, cow DNA was digested with AluI or DdeI, to reduce the 1.720 satellite to base pair monomers which will electrophorese off the bottom off this gel. FIG. 21 shows that clean DNA fingerprints were indeed obtained for each of these restriction enzymes from calf DNA (no. 3). However, almost all of these bands ape derived from variant blocks of 1.720 satellite DNA, embedded within normal 1.720 DNA, which have lost the AluI and DdeI sites in each repeat (perhaps by mutation off one on other of the underlined bases indicated above, which would destroy the overlapping AluI and DdeI sites). This would account for the following facts:

a. Virtually identical calf DNA fingerprints were obtained using AluI and DdeI.
b. The largest fragments consistently hybridize more intensely than the smaller ones (since they contain correspondingly more 1.720 satellite repeat units; the largest calf DNA fragment contains —440 of these units). In humans, band intensity does not increase continuously with size (FIG. 21).
c. Almost all off the calf DNA fingerprint fragments are eliminated by HhaI, which cuts once within the 1.720 repeat unit (see above, data not shown).
d. The sire (no.2) has almost no hybridizing fragments in an AluI digest. This suggests that the region of 1.720 satellite DNA containing these variant repeat blocks has been deleted in this animal.
e. The dam (no.1) and calf (no.3) DNA fingerprints are nearly identical. The dam is probably heterozygous for a deletion, equivalent to that seen in the sire, and has by chance transmitted the non-deleted chromosome (and therefore all bands) to the calf. Thus all of these bands are linked and are not transmitted independently into offspring, as occurs in humans.

Nevertheless, all five cattle costed show different "satellite" DNA fingerprint patterns and thus these unusual types of fingerprints may be of use in individual identification, though not for providing multi locus marker information.

Certain probes may successfully operate where n does not necessarily equal three in formula (1). In such probes at least one pair of repeats of (J.core.K) may be separated from at least two further repeats by a DNA sequence containing no core. Thus a sufficiently long probe may be constructed in which (J.core K) sequences are arranged in pairs separated by "non-core" DNA sequences.

What I claim:

1. A method of characterizing a test sample of genomic DNA by reference to a genetic variation by probing said DNA with a polynucleotide probe, which method comprises the steps of fragmenting said sample DNA with at least one restriction endonuclease, hybridizing said probe to corresponding DNA fragments, and detecting hybridized fragments of said DNA, wherein said probe consists essentially of:
  i) a detectable marker; and
  ii) a polynucleotide consisting of the general formula H.(J.core.K.)$_n$L  (i)

in which:
(a) (J.core.K.)$_n$ is a tandem repeating unit wherein:
  "n" is from 3 to 10,000;
  "core" represents a sequence having 6–16 consecutive nucleotides, selected from within any of the following sequences read 5'→3':

GGAGGTGGGCAGGAXG  (2)

AGAGGTGGGCAGGTGG  (3)

GGAGGYGGGCAGGAGG  (4)

T(C)$_m$GGAGGAXGG(G)$_p$C  (5A)

T(C)$_m$GGAGGA(A)$_q$GGGC  (5B)

in which X is A or G, Y is C or T, T is T or U, m is 0, 1 or 2, p is 0 or 1, q is 0 or 1; and
"J" and "K" together represent 0 to 15 additional nucleotides within the repeating unit;
provided that "core" and "J" and "K" do not necessarily have the same sequence or same length in each (J.core.K.) repeating unit;
(b) "H" and "L" each represent additional nucleotides flanking the tandem repeating unit; and
(c) core sequences in all n repeating units have 70–100% sequence similarity with the core sequence as defined with respect to formulae (2)–(5B) above;
or a polynucleotide of complementary sequence to the above;
said probe being capable of hybridizing with corresponding DNA fragments from more than one minisatellite region or hypervariable locus, thereby characterizing said genomic DNA by reference to the genetic variation at more than one such region or locus.

2. A method of characterizing a test sample of genomic DNA by reference to a genetic variation by probing said DNA with a polynucleotide probe, which method comprises the steps of fragmenting said sample DNA with at least one restriction endonuclease, hybridizing said probe to corresponding DNA fragments, and detecting hybridized fragments of said DNA, wherein said probe consists essentially of a detectable marker and from 3 to 10,000 tandem repeats of a repeat unit sequence consisting of one of:

A
GGAGGTGGGCAGGAGA (ii) (a)aGGGCtGGAGG
(iii) aGAGGTGGGCAGGtGG

C
gGGAGGTGGGCAGGAGG (v) TGGGCtGG
(vi) GTGGGCAGGAAG
(vii) TGGGCAG
(viii) GGTGGGCAGGtGG
(ix) aGGGCA
(x) AGGcaGGtAGGtGG or a sequence complementary thereto of identical length; said probe being capable of hybridizing with corresponding DNA fragments from more than one minisatellite region or hypervariable locus, thereby characterizing said genomic DNA by reference to the genetic variation at more than one such region or locus.

3. A method of characterizing a test sample of genomic DNA by reference to a genetic variation by probing said DNA with a polynucleotide probe, which method comprises the steps of fragmenting said sample DNA with at least one restriction endonuclease, hybridizing said probe to corresponding DNA fragments, and detecting hybridized fragments of said DNA, wherein said probe consists essentially of a detectable marker and from 3 to 10,000 tandem repeats of a repeat unit sequence consisting of one of:
(xi) TGGCA (xi) PGGGCWG (xiii) GPGGGCWGGWXG wherein P=not G, W=A or T or U, and X=A or G; or a sequence complementary thereto of identical length; said probe being capable of hybridizing with corresponding DNA fragments from more than one minisatellite region or hypervariable locus, thereby characterizing said genomic DNA by reference to the genetic variation at more than one such region or locus.

4. The method of claim 3 wherein the repeat unit sequence is selected from one of:

(ii) (a) aGGGCtGGAGG and (iii) aGAGGTGGGCAGGtGG.

5. A method of characterizing a test sample of genomic DNA by reference to a genetic variation by probing said DNA with a polynucleotide probe, which method comprises the steps of fragmenting said sample DNA with at least one restriction endonuclease, hybridizing said probe to corresponding DNA fragments, and detecting hybridized fragments of said DNA, wherein said probe consists essentially of a detectable marker and from 3 to 10,000 tandem repeats of a repeat unit sequence consisting of one of:

(xiv) (A)AGGGCTGGAGG (xv) AGAGGTGGGCAGGTGG or a sequence complementary thereto of identical length; said probe being capable of hybridizing with corresponding DNA fragments from more than one minisatellite region or hypervariable locus, thereby characterizing said genomic DNA by reference to the genetic variation at more than one such region or locus.

6. The method of any one of claims 1, 2, 3, 4 and 5 wherein the repeat unit is repeated up to 10 times.

* * * * *